US006187310B1

(12) United States Patent
Mann et al.

(10) Patent No.: US 6,187,310 B1
(45) Date of Patent: *Feb. 13, 2001

(54) **RECOMBINANT *ENTAMOEBA HISTOLYTICA* LECTIN SUBUNIT PEPTIDES AND REAGENTS SPECIFIC FOR MEMBERS OF THE 170 KDA SUBUNIT MULTIGENE FAMILY**

(75) Inventors: Barbara J. Mann; James M. Dodson; William A. Petri, Jr., all of Charlottesville, VA (US)

(73) Assignee: University of Virginia Patent Foundation, Charlottesville, VA (US)

( * ) Notice: Under 35 U.S.C. 154(b), the term of this patent shall be extended for 0 days.

This patent is subject to a terminal disclaimer.

(21) Appl. No.: 08/937,236

(22) Filed: Sep. 16, 1997

Related U.S. Application Data

(63) Continuation-in-part of application No. 08/569,214, filed as application No. PCT/US94/06890 on Jun. 17, 1994, which is a continuation of application No. 08/078,476, filed on Jun. 17, 1993, now abandoned, which is a continuation of application No. 08/130,735, filed on Oct. 1, 1993, now abandoned, which is a continuation-in-part of application No. 07/615,719, filed on Nov. 21, 1990, now Pat. No. 5,260,429, which is a continuation-in-part of application No. 08/075, 226, filed on Jun. 10, 1993, now Pat. No. 5,401,831, which is a division of application No. 07/479,691, filed on Feb. 13, 1990, now Pat. No. 5,272,058, and a continuation-in-part of application No. 07/456,579, filed on Dec. 29, 1989, now Pat. No. 5,004,608, which is a continuation of application No. 07/143,626, filed on Jan. 13, 1988, now abandoned.

(51) Int. Cl.[7] .......................... A61K 39/002; C07K 14/44

(52) U.S. Cl. .................... 424/185.1; 424/265.1; 424/269.1; 530/300; 530/350

(58) Field of Search ..................... 530/300, 350; 424/130.1, 185.1, 265.1, 269.1

(56) References Cited

U.S. PATENT DOCUMENTS 5,004,608  4/1991  Ravdin et al. .
5,260,429  11/1993  Petri et al. .
5,272,058  12/1993  Petri, Jr. et al. .

FOREIGN PATENT DOCUMENTS

WO 91/12529  8/1991  (WO) .

OTHER PUBLICATIONS

Petri, W.A. et al., *J. Biol. Chem.* (1989), vol. 264, pp. 3007–3012.
Petri, W.A. Jr., et al., *Am. Journal Med. Sci.* (1989), vol. 296, pp. 163–165.
Petri et al., *Infect. Immun.* (1987), vol. 55, pp. 2327–2331.
Petri et al., *J. Immunol.* (1990), vol. 144, pp. 4803–4809.
Schain et al., *Infect. Immun.* (1992), vol. 60, pp. 2143–2146.
Mann, B. et al., *Proc. Natl. Acad. Sci. USA* (1991), vol. 88, pp. 3248–3252.
Tannich, et al., *Proc. Natl. Acad. Sci. USA* (1991), vol. 88, pp. 1849–1853.
Mann, B. et al. *Parasit Today* (1991), vol. 7, pp. 173–176.
Mann, B.J. et al., *Infect. Immun.* (1993), vol. 61, pp. 1772–1778.
Meerovitch et al., Wiley Medical Publishing (1988) pp. 177–190; Amebiasis; Human Infection by Entamoeba Histolytical, In Vivo Models for Pathogenicity in Amebiasis.
Root, et al., *Arch. Invest. Med. (Mex)* (1978), vol. 9: Supplement 1:203.
Palacios et al., *Arch. Invest. Med (Mex)* (1978), vol. 9: Supplement 1:203.
Randall et al., *Trans. Roy Soc Trop. Med. Hygiene* (1984), vol. 78, pp. 593–595.
Grundy, *Trans. Roy. Soc. Trop. Med. Hygiene* (1982), vol. 76, p. 396.
Ungar, *Am. Journal Trop. Med. Hygiene* (1985), vol. 34, pp. 465–472.
*Amebiasis: Human Infection by Entamoeba Histolytica*, J. Ravdin, ed. (1988) Wiley Medical Publishing, pp. 635–649.
Krupp, I.M., *Am. J. Trop. Med. Hygiene*, (1970), vol. 19, pp. 57–62.
Lobel, H.O. et al., *Ann. Rev. Microbiol.* (1978), vol. 32, pp. 329–347.
Ravdin, J.I. et al., *J. Infectious Diseases* (1990), vol. 162, pp. 768–772.
Stanley, Jr. S.L. et al., *Proc. Natl. Acad. Sci. USA* (1990), vol. 87, pp. 4976–4980.
Stanley, Jr. S.L. et al., *JAMA* (1991), vol. 266, pp. 1984–1986.
Zhang, Y. et al., *J. Clin. Micro–Immunol.*, (1992), vol. 30, No. 11, pp. 2788–2792.
Plotkin et al., *Vaccines* (1988) W.B. Saunders Company, pp. 568–575.
Purdy et al., *Molecular and Biochemical Parasitol.*, (1993), vol. 62, No. 1, pp. 53–60.
Chung et al., (1992) Abstract, 1992 Meeting of the American Federation of Clinical Researchers (AFCR).
Buell et al., *JBC*, vol. 254, pp. 9277–9283, 1979.*

* cited by examiner

*Primary Examiner*—Gary L. Kunz
*Assistant Examiner*—Stephen Gucker
(74) *Attorney, Agent, or Firm*—Shmuel Livnat; Rader, Fishman & Grauer

(57) ABSTRACT

The 170 kDa adhesin subunit of the *Entamoeba histolytica* Gal/GalNAc adherence lectin is encoded by members of a gene family that includes hgl1, hgl2 and a newly discovered gene, hgl3. The DNA and encoded protein sequences of the hgl genes are disclosed. A number of proteins and peptide fragments of the adhesin as well as other functional derivatives, preferably produced by recombinant methods in prokaryotic cells are disclosed. A preferred peptide for a vaccine composition corresponds to amino acids 896–998 of the mature 170 kDa lectin and contains the galactose- and N-acetylgalactosamine-binding activity of the native lectin. These compositions are useful as immunogenic vaccine components and as diagnostic reagents. Methods are provided for a vaccine comprising one or more peptides of the lectin to immunize subjects at risk for infection by *E. histolytica*. Additionally, immunoassay methods are disclosed for measuring antibodies specific for an epitope of the lectin. These methods detect *E. histolytica*-specific antibodies, some of which are specific for epitopes characteristic of pathogenic strains, nonpathogenic strains, or both.

22 Claims, 19 Drawing Sheets

```
  1 ATG AAA TTA TTA TTA TTA AAT ATC TTA TTA TTA TGT TGT CTT   42
    M   K   L   L   L   L   N   I   L   L   L   C   C   L

43 GCA GAT AAA CTT GAT GAA TTT TCA GCA GAT AAT GAC TAT TAT   84
    A   D   K   L   D   E   F   S   A   D   N   D   Y   Y

85 GAC GGT GGT ATT ATG TCT CGT GGA AAG AAT GCA GGT TCA TGG  126
    D   G   G   I   M   S   R   G   K   N   A   G   S   W

127 TAT CAT TCT TAC ACT CAC CAA TAT GAT GTT TTC TAT TAT TTA  168
    Y   H   S   Y   T   H   Q   Y   D   V   F   Y   Y   L

169 GCT ATG CAA CCA TGG AGA CAT TTT GTA TGG ACT ACA TGC GAT  210
    A   M   Q   P   W   R   H   F   V   W   T   T   C   D

211 AAA AAT GAT AAT ACA GAA TGT TAT AAA TAT ACT ATC AAT GAA  252
    K   N   D   N   T   E   C   Y   K   Y   T   I   N   E

253 GAT CAT AAT GTA AAG GTT GAA GAT ATT AAT AAA ACA AAT ATT  294
    D   H   N   V   K   V   E   D   I   N   K   T   N   I

295 AAA CAA GAT TTT TGT CAA AAA GAA TAT GCA TAT CCA ATT GAA  336
    K   Q   D   F   C   Q   K   E   Y   A   Y   P   I   E

337 AAA TAT GAA GTT GAT TGG GAC AAT GTT CCA GTT GAT GAA CAA  378
    K   Y   E   V   D   W   D   N   V   P   V   D   E   Q

379 CGA ATT GAA AGT GTA GAT ATT AAT GGA AAA ACT TGT TTT AAA  420
    R   I   E   S   V   D   I   N   G   K   T   C   F   K

421 TAT GCA GCT AAA AGA CCA TTG GCT TAT GTT TAT TTA AAT ACA  462
    Y   A   A   K   R   P   L   A   Y   V   Y   L   N   T

463 AAA ATG ACA TAT GCA ACA AAA ACT GAA GCA TAT GAT GTT TGT  504
    K   M   T   Y   A   T   K   T   E   A   Y   D   V   C

505 AGA ATG GAT TTC ATT GGA GGA AGA TCA ATT ACA TTC AGA TCA  546
    R   M   D   F   I   G   G   R   S   I   T   F   R   S

547 TTT AAC ACA GAG AAT AAA GCA TTT ATT GAT CAA TAT AAT ACA  588
    F   N   T   E   N   K   A   F   I   D   Q   Y   N   T

589 AAC ACT ACA TCA AAA TGT CTT CTT AAT GTA TAT GAT AAT AAT  630
    N   T   T   S   K   C   L   L   N   V   Y   D   N   N

631 GTT AAT ACA CAT CTT GCA ATT ATC TTT GGT ATT ACT GAT TCT  672
    V   N   T   H   L   A   I   I   F   G   I   T   D   S

673 ACA GTC ATT AAA TCA CTT CAA GAG AAT TTA TCT CTT TTA AGT  714
    T   V   I   K   S   L   Q   E   N   L   S   L   L   S

715 CAA CTA AAA ACA GTC AAA GGA GTA ACA CTC TAC TAT CTT AAA  756
    Q   L   K   T   V   K   G   V   T   L   Y   Y   L   K

757 GAT GAT ACT TAT TTT ACA GTT AAT ATT ACT TTA GAT CAA TTA  798
```

FIG. IA

|     | D   | D   | T   | Y   | F   | T   | V   | N   | I   | T   | L   | D   | Q   | L   |      |
|-----|-----|-----|-----|-----|-----|-----|-----|-----|-----|-----|-----|-----|-----|-----|------|
| 799 | AAA | TAT | GAT | ACA | CTT | GTC | AAA | TAC | ACA | GCA | GGA | ACA | GGA | CAA | 840  |
|     | K   | Y   | D   | T   | L   | V   | K   | Y   | T   | A   | G   | T   | G   | Q   |      |
| 841 | GTT | GAT | CCA | CTT | ATT | AAT | ATT | GCT | AAG | AAT | GAT | TTA | GCT | ACT | 882  |
|     | V   | D   | P   | L   | I   | N   | I   | A   | K   | N   | D   | L   | A   | T   |      |
| 883 | AAA | GTT | GCA | GAT | AAA | AGT | AAA | GAT | AAA | AAT | GCA | AAT | GAT | AAA | 924  |
|     | K   | V   | A   | D   | K   | S   | K   | D   | K   | N   | A   | N   | D   | K   |      |
| 925 | ATC | AAA | AGA | GGA | ACT | ATG | ATT | GTG | TTA | ATG | GAT | ACT | GCA | CTT | 966  |
|     | I   | K   | R   | G   | T   | M   | I   | V   | L   | M   | D   | T   | A   | L   |      |
| 967 | GGA | TCA | GAA | TTT | AAT | GCA | GAA | ACA | GAA | TTT | GAT | AGA | AAG | AAT | 1008 |
|     | G   | S   | E   | F   | N   | A   | E   | T   | E   | F   | D   | R   | K   | N   |      |
| 1009| ATT | TCA | GTT | CAT | ACT | GTT | GTT | CTT | AAT | AGA | AAT | AAA | GAC | CCA | 1050 |
|     | I   | S   | V   | H   | T   | V   | V   | L   | N   | R   | N   | K   | D   | P   |      |
| 1051| AAG | ATT | ACA | CGT | AGT | GCA | TTG | AGA | CTT | GTT | TCA | CTT | GGA | CCA | 1092 |
|     | K   | I   | T   | R   | S   | A   | L   | R   | L   | V   | S   | L   | G   | P   |      |
| 1093| CAT | TAT | CAT | GAA | TTT | ACA | GGT | AAT | GAT | GAA | GTT | AAT | GCA | ACA | 1134 |
|     | H   | Y   | H   | E   | F   | T   | G   | N   | D   | E   | V   | N   | A   | T   |      |
| 1135| ATC | ACT | GCA | CTT | TTC | AAA | GGA | ATT | AGA | GCC | AAT | TTA | ACA | GAA | 1176 |
|     | I   | T   | A   | L   | F   | K   | G   | I   | R   | A   | N   | L   | T   | E   |      |
| 1177| AGA | TGT | GAT | AGA | GAT | AAA | TGT | TCA | GGA | TTT | TGT | GAT | GCA | ATG | 1218 |
|     | R   | C   | D   | R   | D   | K   | C   | S   | G   | F   | C   | D   | A   | M   |      |
| 1219| AAT | AGA | TGC | ACA | TGT | CCA | ATG | TGT | TGT | GAG | AAT | GAT | TGT | TTC | 1260 |
|     | N   | R   | C   | T   | C   | P   | M   | C   | C   | E   | N   | D   | C   | F   |      |
| 1261| TAT | ACA | TCC | TGT | GAT | GTA | GAA | ACA | GGA | TCA | TGT | ATT | CCA | TGG | 1302 |
|     | Y   | T   | S   | C   | D   | V   | E   | T   | G   | S   | C   | I   | P   | W   |      |
| 1303| CCT | AAA | GCT | AAA | CCA | AAA | GCA | AAG | AAA | GAA | TGT | CCA | GCA | ACA | 1344 |
|     | P   | K   | A   | K   | P   | K   | A   | K   | K   | E   | C   | P   | A   | T   |      |
| 1345| TGT | GTA | GGC | TCA | TAT | GAA | TGT | AGA | GAT | CTT | GAA | GGA | TGT | GTT | 1386 |
|     | C   | V   | G   | S   | Y   | E   | C   | R   | D   | L   | E   | G   | C   | V   |      |
| 1387| GTT | ACA | AAA | TAT | AAT | GAC | ACA | TGC | CAA | CCA | AAA | GTG | AAA | TGC | 1428 |
|     | V   | T   | K   | Y   | N   | D   | T   | C   | Q   | P   | K   | V   | K   | C   |      |
| 1429| ATG | GTA | CCA | TAT | TGT | GAT | AAT | GAT | AAG | AAT | CTA | ACT | GAA | GTA | 1470 |
|     | M   | V   | P   | Y   | C   | D   | N   | D   | K   | N   | L   | T   | E   | V   |      |
| 1471| TGT | AAA | CAA | AAA | GCT | AAT | TGT | GAA | GCA | GAT | CAA | AAA | CCA | AGT | 1512 |
|     | C   | K   | Q   | K   | A   | N   | C   | E   | A   | D   | Q   | K   | P   | S   |      |
| 1513| TCT | GAT | GGA | TAT | TGT | TGG | AGT | TAT | ACA | TGT | GAC | CAA | ACT | ACT | 1554 |
|     | S   | D   | G   | Y   | C   | W   | S   | Y   | T   | C   | D   | Q   | T   | T   |      |
| 1555| GGT | TTT | TGT | AAG | AAA | GAT | AAA | CGA | GGT | AAA | GAA | ATG | TGT | ACA | 1596 |

FIG. IA

```
              G    F    C    K    K    D    K    R    G    K    E    M    C    T
         1597 GGA  AAG  ACA  AAT  AAT  TGT  CAA  GAA  TAT  GTT  TGT  GAT  TCA  GAA  1638
              G    K    T    N    N    C    Q    E    Y    V    C    D    S    E

1639 CAA  AGA  TGT  AGT  GTT  AGA  GAT  AAA  GTA  TGT  GTA  AAA  ACA  TCA  1680
              Q    R    C    S    V    R    D    K    V    C    V    K    T    S

1681 CCA  TAC  ATT  GAA  ATG  TCA  TGT  TAT  GTA  GCC  AAG  TGT  AAT  CTC  1722
              P    Y    I    E    M    S    C    Y    V    A    K    C    N    L

1723 AAT  ACA  GGT  ATG  TGT  GAG  AAC  AGA  TTA  TCA  TGT  GAT  ACA  TAC  1764
              N    T    G    M    C    E    N    R    L    S    C    D    T    Y

1765 TCA  TCA  TGT  GGT  GGA  GAT  TCT  ACA  GGA  TCA  GTA  TGT  AAA  TGT  1806
              S    S    C    G    G    D    S    T    G    S    V    C    K    C

1807 GAT  TCT  ACA  ACT  GGT  AAT  AAA  TGT  CAA  TGT  AAT  AAA  GTA  AAA  1848
              D    S    T    T    G    N    K    C    Q    C    N    K    V    K

1849 AAT  GGT  AAT  TAT  TGT  AAT  TCT  AAA  AAC  CAT  GAA  ATT  TGT  GAT  1890
              N    G    N    Y    C    N    S    K    N    H    E    I    C    D

1891 TAT  ACA  GGA  ACA  ACA  CCA  CAA  TGT  AAA  GTG  TCT  AAT  TGT  ACA  1932
              Y    T    G    T    T    P    Q    C    K    V    S    N    C    T

1933 GAA  GAT  CTT  GTT  AGA  GAT  GGA  TGT  CTT  ATT  AAG  AGA  TGC  AAT  1974
              E    D    L    V    R    D    G    C    L    I    K    R    C    N

1975 GAA  ACA  AGT  AAA  ACA  ACA  TAT  TGG  GAG  AAT  GTT  GAT  TGT  TCA  2016
              E    T    S    K    T    T    Y    W    E    N    V    D    C    S

2017 AAC  ACT  AAG  ATT  GAA  TTT  GCT  AAA  GAT  GAT  AAA  TCT  GAA  ACT  2058
              N    T    K    I    E    F    A    K    D    D    K    S    E    T

2059 ATG  TGT  AAA  CAA  TAT  TAT  TCA  ACT  ACA  TGT  TTG  AAT  GGA  AAA  2100
              M    C    K    Q    Y    Y    S    T    T    C    L    N    G    K

2101 TGT  GTT  GTT  CAA  GCA  GTT  GGT  GAT  GTT  TCT  AAT  GTA  GGA  TGT  2142
              C    V    V    Q    A    V    G    D    V    S    N    V    G    C

2143 GGA  TAT  TGT  TCA  ATG  GGA  ACA  GAT  AAT  ATT  ATT  ACA  TAT  CAT  2184
              G    Y    C    S    M    G    T    D    N    I    I    T    Y    H
```

FIG. IA

```
2185 GAT GAT TGT AAT TCA CGT AAA TCA CAA TGT GGA AAC TTT AAT 2226
      D   D   C   N   S   R   K   S   Q   C   G   N   F   N

2227 GGT AAA TGT ATT AAA GGC AGT GAC AAT TCT TAT TCT TGT GTA 2268
      G   K   C   I   K   G   S   D   N   S   Y   S   C   V

2269 TTT GAA AAA GAT AAA ACT TCT TCT AAA TCA GAT AAT GAT ATT 2310
      F   E   K   D   K   T   S   S   K   S   D   N   D   I

2311 TGT GCT GAA TGT TCT AGT TTA ACA TGT CCA GCT GAT ACT ACA 2352
      C   A   E   C   S   S   L   T   C   P   A   D   T   T

2353 TAC AGA ACA TAT ACA TAT GAC TCA AAA ACA GGA ACA TGT AAA 2394
      Y   R   T   Y   T   Y   D   S   K   T   G   T   C   K

2395 GCA ACT GTT CAA CCA ACA CCA GCA TGT TCA GTA TGT GAA AGT 2436
      A   T   V   Q   P   T   P   A   C   S   V   C   E   S

2437 GGT AAA TTT GTA GAG AAA TGC AAA GAT CAA AAA TTA GAA CGT 2478
      G   K   F   V   E   K   C   K   D   Q   K   L   E   R

2479 AAA GTC ACT TTA GAA AAT GGA AAA GAA TAT AAA TAC ACC ATT 2520
      K   V   T   L   E   N   G   K   E   Y   K   Y   T   I

2521 CCA AAA GAT TGT GTC AAT GAA CAA TGC ATT CCA AGA ACA TAC 2562
      P   K   D   C   V   N   E   Q   C   I   P   R   T   Y

2563 ATA GAT TGT TTA GGT AAT GAT GAT AAC TTT AAA TCT ATT TAT 2604
      I   D   C   L   G   N   D   D   N   F   K   S   I   Y

2605 AAC TTC TAT TTA CCA TGT CAA GCA TAT GTT ACA GCT ACC TAT 2646
      N   F   Y   L   P   C   Q   A   Y   V   T   A   T   Y

2647 CAT TAC AGT TCA TTA TTC AAT TTA ACT AGT TAT AAA CTT CAC 2688
      H   Y   S   S   L   F   N   L   T   S   Y   K   L   H

2689 TTA CCA CAA AGT GAA GAA TTT ATG AAA GAG GCA GAC AAA GAA 2730
      L   P   Q   S   E   E   F   M   K   E   A   D   K   E

2731 GCA TAT TGT ACA TAC GAA ATA ACA ACA AGA GAA TGT AAA ACA 2772
      A   Y   C   T   Y   E   I   T   T   R   E   C   K   T

2773 TGT TCA TTA ATT GAA ACT AGA GAA AAA GTC CAA GAA GTT GAT 2814
      C   S   L   I   E   T   R   E   K   V   Q   E   V   D

2815 TTG TGT GCA GAA GAA ACT AAG AAT GGA GGA GTT CCA TTC AAA 2856
      L   C   A   E   E   T   K   N   G   G   V   P   F   K

2857 TGT AAG AAT AAC AAT TGC ATT ATT GAT CCT AAC TTT GAT TGT 2898
      C   K   N   N   N   C   I   I   D   P   N   F   D   C

2899 CAA CCT ATT GAA TGT AAG ATT CAA GAG ATT GTT ATT ACA GAA 2940
      Q   P   I   E   C   K   I   Q   E   I   V   I   T   E

2941 AAA GAT GGA ATA AAA ACA ACA ACA TGT AAA AAT ACT ACA AAA 2982
      K   D   G   I   K   T   T   T   C   K   N   T   T   K
```

FIG. 1A

```
2983  GCA ACA TGT GAC ACT AAC AAT AAG AGA ATA GAA GAT GCA CGT  3024
       A   T   C   D   T   N   N   K   R   I   E   D   A   R

3025  AAA GCA TTC ATT GAA GGA AAA GAA GGA ATT GAG CAA GTA GAA  3066
       K   A   F   I   E   G   K   E   G   I   E   Q   V   E

3067  TGT GCA AGT ACT GTT TGT CAA AAT GAT AAT AGT TGT CCA ATT  3108
       C   A   S   T   V   C   Q   N   D   N   S   C   P   I

3109  ATT ACT GAT GTA GAA AAA TGT AAT CAA AAC ACA GAA GTA GAT  3150
       I   T   D   V   E   K   C   N   Q   N   T   E   V   D

3151  TAT GGA TGT AAA GCA ATG ACA GGA GAA TGT GAT GGT ACT ACA  3192
       Y   G   C   K   A   M   T   G   E   C   D   G   T   T

3193  TAT CTT TGT AAA TTT GTA CAA CTT ACT GAT GAT CCA TCA TTA  3234
       Y   L   C   K   F   V   Q   L   T   D   D   P   S   L

3235  GAT AGT GAA CAT TTT AGA ACT AAA TCA GGA GTT GAA CTT AAC  3276
       D   S   E   H   F   R   T   K   S   G   V   E   L   N

3277  AAT GCA TGT TTG AAA TAT AAA TGT GTT GAG AGT AAA GGA AGT  3318
       N   A   C   L   K   Y   K   C   V   E   S   K   G   S

3319  GAT GGA AAA ATC ACA CAT AAA TGG GAA ATT GAT ACA GAA CGA  3360
       D   G   K   I   T   H   K   W   E   I   D   T   E   R

3361  TCA AAT GCT AAT CCA AAA CCA AGA AAT CCA TGC GAA ACC GCA  3402
       S   N   A   N   P   K   P   R   N   P   C   E   T   A

3403  ACA TGT AAT CAA ACA ACT GGA GAA ACT ATT TAC ACA AAG AAA  3444
       T   C   N   Q   T   T   G   E   T   I   Y   T   K   K

3445  ACA TGT ACT GTT TCA GAA TTC CCA ACA ATC ACA CCA AAT CAA  3486
       T   C   T   V   S   E   F   P   T   I   T   P   N   Q

3487  GGA AGA TGT TTC TAT TGT CAA TGT TCA TAT CTT GAC GGT TCA  3528
       G   R   C   F   Y   C   Q   C   S   Y   L   D   G   S

3529  TCA GTT CTT ACT ATG TAT GGA GAA ACA GAT AAA GAA TAT TAT  3570
       S   V   L   T   M   Y   G   E   T   D   K   E   Y   Y
```

FIG. 1A

```
3571 GAT CTT GAT GCA TGT GGT AAT TGT CGT GTT TGG AAT CAG ACA 3612
     D   L   D   A   C   G   N   C   R   V   W   N   Q   T

3613 GAT AGA ACA CAA CAA CTT AAT AAT CAC ACC GAG TGT ATT CTC 3654
     D   R   T   Q   Q   L   N   N   H   T   E   C   I   L

3655 GCA GGA GAA ATT AAT AAT GTT GGA GCT ATT GCA GCG GCA ACT 3696
     A   G   E   I   N   N   V   G   A   I   A   A   A   T

3697 ACT GTG GCT GCT GTT ATA GTT GCA GTT GTA GTT GCA TTA ATT 3738
     T   V   A   A   V   I   V   A   V   V   V   A   L   I

3739 GTT GTT TCT ATT GGA TTA TTT AAG ACT TAT CAA CTT GTT TCA 3780
     V   V   S   I   G   L   F   K   T   Y   Q   L   V   S

3781 TCA GCT ATG AAG AAT GCC ATT ACA ATA ACT AAT GAA AAT GCA 3822
     S   A   M   K   N   A   I   T   I   T   N   E   N   A

3823 GAA TAT GTT GGA GCA GAT AAT GAA GCA ACT AAT GCA GCA ACA 3864
     E   Y   V   G   A   D   N   E   A   T   N   A   A   T

3865 TTC AAT GGA TAA GAA CAA TAA TTA AGC C        3892
     F   N   G   Z   E   Q   Z   L   S
```

FIG. IA

```
  -15        MKLLL  LNILLLCCLA  DKLDEFSADN  DYYDGGIMSR  GKNAGSWYHS
   31   YTHQYDVFYY  LAMQPWRHFV  WTTCDKNDNT  ECYKYTINED  HNVKVEDINK
   81   TNIKQDFCQK  EYAYPIEKYE  VDWDNVPVDE  QRIESVDING  KTCFKYAAKR
  131   PLAYVYLNTK  MTYATKTEAY  DVCRMDFIGG  RSITFRSFNT  ENKAFIDQYN
  181   TNTTSKCLLN  VYDNNVNTHL  AIIFGITDST  VIKSLQENLS  LLSQLKTVKG
  231   VTLYYLKDDT  YFTVNITLDQ  LKYDTLVKYT  AGTGQVDPLI  NIAKNDLATK
  281   VADKSKDKNA  NDKIKRGTMI  VLMDTALGSE  FNAETEFDRK  NISVHTVVLN
  331   RNKDPKITRS  ALRLVSLGPH  YHEFTGNDEV  NATITALFKG  IRANLTERCD
  381   RDKCSGFCDA  MNRCTCPMCC  ENDCFYTSCD  VETGSCIPWP  KAKPKAKKEC
  431   PATCVGSYEC  RDLEGCVVTK  YNDTCQPKVK  CMVPYCDNDK  NLTEVCKQKA
  481   NCEADQKPSS  DGYCWSYTCD  QTTGFCKKDK  RGKEMCTGKT  NNCQEYVCDS
  531   EQRCSVRDKV  CVKTSPYIEM  SCYVAKCNLN  TGMCENRLSC  DTYSSCGGDS
  581   TGSVCKCDST  TGNKCQCNKV  KNGNYCNSKN  HEICDYTGTT  PQCKVSNCTE
  631   DLVRDGCLIK  RCNETSKTTY  WENVDCSNTK  IEFAKDDKSE  TMCKQYYSTT
  681   CLNGKCVVQA  VGDVSNVGCG  YCSMGTDNII  TYHDDCNSRK  SQCGNFNGKC
  731   IKGSDNSYSC  VFEKDKTSSK  SDNDICAECS  SLTCPADTTY  RTYTYDSKTG
  781   TCKATVQPTP  ACSVCESGKF  VEKCKDQKLE  RKVTLENGKE  YKYTIPKDCV
  831   NEQCIPRTYI  DCLGNDDNFK  SIYNFYLPCQ  AYVTATYHYS  SLFNLTSYKL
  881   HLPQSEEFMK  EADKEAYCTY  EITTRECKTC  SLIETREKVQ  EVDLCAEETK
  931   NGGVPFKCKN  NNCIIDPNFD  CQPIECKIQE  IVITEKDGIK  TTTCKNTTKA
  981   TCDTNNKRIE  DARKAFIEGK  EGIEQVECAS  TVCQNDNSCP  IITDVEKCNQ
 1031   NTEVDYGCKA  MTGECDGTTY  LCKFVQLTDD  PSLDSEHFRT  KSGVELNNAC
 1081   LKYKCVESKG  SDGKITHKWE  IDTERSNANP  KPRNPCETAT  CNQTTGETIY
 1131   TKKTCTVSEF  PTITPNQGRC  FYCQCSYLDG  SSVLTMYGET  DKEYYDLDAC
 1181   GNCRVWNQTD  RTQQLNNHTE  CILAGEINNV  GAIAAATTVA  AVIVAVVVAL
 1231   IVVSIGLFKT  YQLVSSAMKN  AITITNENAE  YVGADNEATN  AATFNG
```

FIG. 1B

```
  1 TTC TGT TAA ATA GGA AAG GCA AGT GAT TTA AAC AAG ACA ATG  42

43 AAC TAG AAA GAC AAA GAT ATG AAA TTA TTA TTA TTA AAT ATC  84
                                 M   K   L   L   L   L   N   I

85 TTA TTA TTA TGT TGT CTT GCA GAT AAA CTT AAT GAA TTT TCA 126
     L   L   L   C   C   L   A   D   K   L   N   E   F   S

127 GCA GAT ATT GAT TAT TAT GAC CTT GGT ATT ATG TCT CGT GGA 168
     A   D   I   D   Y   Y   D   L   G   I   M   S   R   G

169 AAG AAT GCA GGT TCA TGG TAT CAT TCT TAT GAA CAT CAA TAT 210
     K   N   A   G   S   W   Y   H   S   Y   E   H   Q   Y

211 GAT GTT TTC TAT TAT TTA GCT ATG CAA CCA TGG AGA CAT TTT 252
     D   V   F   Y   Y   L   A   M   Q   P   W   R   H   F

253 GTA TGG ACT ACT TGT ACA ACA ACT GAT GGC AAT AAA GAA TGT 294
     V   W   T   T   C   T   T   T   D   G   N   K   E   C

295 TAT AAA TAT ACT ATC AAT GAA GAT CAT AAT GTA AAG GTT GAA 336
     Y   K   Y   T   I   N   E   D   H   N   V   K   V   E

337 GAT ATT AAT AAA ACA GAT ATT AAA CAA GAT TTT TGT CAA AAA 378
     D   I   N   K   T   D   I   K   Q   D   F   C   Q   K

379 GAA TAT GCA TAT CCA ATT GAA AAA TAT GAA GTT GAT TGG GAC 420
     E   Y   A   Y   P   I   E   K   Y   E   V   D   W   D

421 AAT GTT CCA GTT GAT GAA CAA CGA ATT GAA AGT GTA GAT ATT 462
     N   V   P   V   D   E   Q   R   I   E   S   V   D   I

463 AAT GGA AAA ACT TGT TTT AAA TAT GCA GCT AAA AGA CCA TTG 504
     N   G   K   T   C   F   K   Y   A   A   K   R   P   L

505 GCT TAT GTT TAT TTA AAT ACA AAA ATG ACA TAT GCA ACA AAA 546
     A   Y   V   Y   L   N   T   K   M   T   Y   A   T   K

547 ACT GAA GCA TAT GAT GTT TGT AGA ATG GAT TTC ATT GGA GGA 588
     T   E   A   Y   D   V   C   R   M   D   F   I   G   G

589 AGA TCA ATT ACA TTC AGA TCA TTT AAC ACA GAG AAT AAA GCA 630
     R   S   I   T   F   R   S   F   N   T   E   N   K   A

631 TTT ATT GAT CAA TAT AAT ACA AAC ACT ACA TCA AAA TGT CTT 672
     F   I   D   Q   Y   N   T   N   T   T   S   K   C   L

673 CTT AAA GTA TAT GAT AAT AAT GTT AAT ACA CAT CTT GCA ATT 714
     L   K   V   Y   D   N   N   V   N   T   H   L   A   I

715 ATC TTT GGT ATT ACT GAT TCT ACA GTC ATT AAA TCA CTT CAA 756
     I   F   G   I   T   D   S   T   V   I   K   S   L   Q
```

FIG. 4A

```
757  GAG AAC TTA TCT CTT TTA AAT AAA TTA ACA ACA GTC AAA GGA  798
      E   N   L   S   L   L   N   K   L   T   T   V   K   G

799  GTA ACA CTC TAC TAT CTT AAA GAT GAT ACT TAT TTT ACA GTT  840
      V   T   L   Y   Y   L   K   D   D   T   Y   F   T   V

841  AAT ATT ACT TTA AAT GAT TTG AAA TAT GAG ACA CTT GTC CAA  882
      N   I   T   L   N   D   L   K   Y   E   T   L   V   Q

883  TAC ACA GCA GGA ACA GGA CAA GTT GAT CCA CTT ATT AAT ATT  924
      Y   T   A   G   T   G   Q   V   D   P   L   I   N   I

925  GCT AAG AAT GAC TTA ACT GCT AAA GTT GCA GAT AAA AGT AAA  966
      A   K   N   D   L   T   A   K   V   A   D   K   S   K

967  GAT AAA AAT GCA AAT GAT AAA ATC AAA AGA GGA ACT ATG ATT 1008
      D   K   N   A   N   D   K   I   K   R   G   T   M   I

1009 GTG TTA ATG GAT ACT GCA CTT GGA TCA GAA TTT AAT GCG GAA 1050
      V   L   M   D   T   A   L   G   S   E   F   N   A   E

1051 ACA GAA TTT GAT AGA AAG AAT ATT TCA GTT CAT ACT GTT GTT 1092
      T   E   F   D   R   K   N   I   S   V   H   T   V   V

1093 CTT AAT AGA AAT AAA GAC CCA AAG ATT ACA CGT AGT GCA TTG 1134
      L   N   R   N   K   D   P   K   I   T   R   S   A   L

1135 AGA CTT GTT TCA CTT GGA CCA CAT TAT CAT GAA TTT ACA GGT 1176
      R   L   V   S   L   G   P   H   Y   H   E   F   T   G

1177 AAT GAT GAA GTT AAT GCA ACA ATC ACT GCA CTT TTC AAA GGA 1218
      N   D   E   V   N   A   T   I   T   A   L   F   K   G

1219 ATT AGA GCC AAT TTA ACA GAA AGA TGT GAT AGA GAT AAA TGT 1260
      I   R   A   N   L   T   E   R   C   D   R   D   K   C

1261 TCA GGA TTT TGT GAT GCA ATG AAT AGA TGC ACA TGT CCA ATG 1302
      S   G   F   C   D   A   M   N   R   C   T   C   P   M

1303 TGT TGT GAG AAT GAT TGT TTC TAT ACA TCC TGT GAT GTA GAA 1344
      C   C   E   N   D   C   F   Y   T   S   C   D   V   E

1345 ACA GGA TCA TGT ATT CCA TGG CCT AAA GCT AAA CCA AAA GCA 1386
      T   G   S   C   I   P   W   P   K   A   K   P   K   A

1387 AAG AAA GAA TGT CCA GCA ACA TGT GTA GGC TCA TAT GAA TGT 1428
      K   K   E   C   P   A   T   C   V   G   S   Y   E   C

1429 AGA GAT CTT GAA GGA TGT GTT GTT AAA CAA TAT AAT ACA TCT 1470
      R   D   L   E   G   C   V   V   K   Q   Y   N   T   S

1471 TGT GAA CCA AAA GTG AAA TGC ATG GTA CCA TAT TGT GAT AAT 1512
      C   E   P   K   V   K   C   M   V   P   Y   C   D   N
```

FIG. 4B

```
1513 GAT AAG AAT CTA ACT GAA GTA TGT AAA CAA AAA GCT AAT TGT 1554
      D   K   N   L   T   E   V   C   K   Q   K   A   N   C

1555 GAA GCA GAT CAA AAA CCA AGT TCT GAT GGA TAT TGT TGG AGT 1596
      E   A   D   Q   K   P   S   S   D   G   Y   C   W   S

1597 TAT ACA TGT GAC CAA ACT ACT GGT TTT TGT AAG AAA GAT AAA 1638
      Y   T   C   D   Q   T   T   G   F   C   K   K   D   K

1639 CGT GGT GAA AAT ATG TGT ACA GGA AAG ACA AAT AAC TGT CAA 1680
      R   G   E   N   M   C   T   G   K   T   N   N   C   Q

1681 GAA TAT GTT TGT GAT GAA AAA CAA AGA TGT ACT GTT CAA GAA 1722
      E   Y   V   C   D   E   K   Q   R   C   T   V   Q   E

1723 AAG GTA TGT GTA AAA ACA TCA CCT TAT ATT GAA ATG TCA TGT 1764
      K   V   C   V   K   T   S   P   Y   I   E   M   S   C

1765 TAT GTA GCC AAG TGT AAT CTC AAT ACA GGT ATG TGT GAG AAC 1806
      Y   V   A   K   C   N   L   N   T   G   M   C   E   N

1807 AGA TTA TCA TGT GAT ACA TAC TCA TCA TGT GGT GGA GAT TCT 1848
      R   L   S   C   D   T   Y   S   S   C   G   G   D   S

1849 ACA GGA TCA GTA TGT AAA TGT GAT TCT ACA ACT AAT AAC CAA 1890
      T   G   S   V   C   K   C   D   S   T   T   N   N   Q

1891 TGT CAA TGT ACT CAA GTA AAA AAC GGT AAT TAT TGT GAT TCT 1932
      C   Q   C   T   Q   V   K   N   G   N   Y   C   D   S

1933 AAT AAA CAT CAA ATT TGT GAT TAT ACA GGA AAA ACA CCA CAA 1974
      N   K   H   Q   I   C   D   Y   T   G   K   T   P   Q

1975 TGT AAA GTG TCT AAT TGT ACA GAA GAT CTT GTT AGA GAT GGA 2016
      C   K   V   S   N   C   T   E   D   L   V   R   D   G

2017 TGT CTT ATT AAG AGA TGT AAT GAA ACA AGT AAA ACA ACA TAT 2058
      C   L   I   K   R   C   N   E   T   S   K   T   T   Y

2059 TGG GAG AAT GTT GAT TGT TCT AAA ACT GAA GTT AAA TTC GCT 2100
      W   E   N   V   D   C   S   K   T   E   V   K   F   A

2101 CAA GAT GGT AAA TCT GAA AAT ATG TGT AAA CAA TAT TAT TCA 2142
      Q   D   G   K   S   E   N   M   C   K   Q   Y   Y   S

2143 ACT ACA TGT TTG AAT GGA CAA TGT GTT GTT CAA GCA GTT GGT 2184
      T   T   C   L   N   G   Q   C   V   V   Q   A   V   G

2185 GAT GTT TCT AAT GTA GGA TGT GGA TAT TGT TCA ATG GGA ACA 2226
      D   V   S   N   V   G   C   G   Y   C   S   M   G   T

2227 GAT AAT ATT ATT ACA TAT CAT GAT GAT TGT AAT TCA CGT AAA 2268
      D   N   I   I   T   Y   H   D   D   C   N   S   R   K
```

FIG. 4C

```
2269 TCA CAA TGT GGA AAC TTT AAT GGT AAG TGT GTA GAA AAT AGT 2310
     S   Q   C   G   N   F   N   G   K   C   V   E   N   S

2311 GAC AAA TCA TAT TCT TGT GTA TTT AAT AAG GAT GTT TCT TCT 2352
     D   K   S   Y   S   C   V   F   N   K   D   V   S   S

2353 ACA TCA GAT AAT GAT ATT TGT GCA AAA TGT TCT AGT TTA ACA 2394
     T   S   D   N   D   I   C   A   K   C   S   S   L   T

2395 TGT CCA GCT GAT ACT ACA TAC AGA ACA TAT ACA TAT GAC TCA 2436
     C   P   A   D   T   T   Y   R   T   Y   T   Y   D   S

2437 AAA ACA GGA ACA TGT AAA GCA ACT GTT CAA CCA ACA CCA GCA 2478
     K   T   G   T   C   K   A   T   V   Q   P   T   P   A

2479 TGT TCA GTA TGT GAA AGT GGT AAA TTT GTA GAA AAA TGC AAA 2520
     C   S   V   C   E   S   G   K   F   V   E   K   C   K

2521 GAT CAA AAA TTA GAA CGT AAA GTT ACT TTA GAA AAT GGA AAA 2562
     D   Q   K   L   E   R   K   V   T   L   E   N   G   K

2563 GAA TAT AAA TAC ACC ATT CCA AAA GAT TGT GTC AAT GAA CAA 2604
     E   Y   K   Y   T   I   P   K   D   C   V   N   E   Q

2605 TGC ATT CCA AGA ACA TAC ATA GAT TGT TTA GGT AAT GAT GAT 2646
     C   I   P   R   T   Y   I   D   C   L   G   N   D   D

2647 AAC TTT AAA TCT ATT TAT AAC TTC TAT TTA CCA TGT CAA GCA 2688
     N   F   K   S   I   Y   N   F   Y   L   P   C   Q   A

2689 TAT GTT ACA GCT ACC TAT CAT TAC AGT TCA TTA TTC AAT TTA 2730
     Y   V   T   A   T   Y   H   Y   S   S   L   F   N   L

2731 ACT AGT TAT AAA CTT CAT TTA CCA CAA AGT GAA GAA TTT ATG 2772
     T   S   Y   K   L   H   L   P   Q   S   E   E   F   M

2773 AAA GAG GCA GAC AAA GAA GCA TAT TGT ACA TAC GAA ATA ACA 2814
     K   E   A   D   K   E   A   Y   C   T   Y   E   I   T

2815 ACA AGA GAA TGT AAA ACA TGT TCA TTA ATT GAA ACT AGA GAA 2856
     T   R   E   C   K   T   C   S   L   I   E   T   R   E

2857 AAA GTC CAA GAA GTT GAT TTG TGT GCA GAA GAG ACT AAG AAT 2898
     K   V   Q   E   V   D   L   C   A   E   E   T   K   N

2899 GGA GGA GTT CCA TTC AAA TGT AAG AAT AAC AAT TGC ATT ATT 2940
     G   G   V   P   F   K   C   K   N   N   N   C   I   I

2941 GAT CCT AAC TTT GAT TGT CAA CCT ATT GAA TGT AAG ATT CAA 2982
     D   P   N   F   D   C   Q   P   I   E   C   K   I   Q

2983 GAG ATT GTT ATT ACA GAA AAA GAT GGA ATA AAA ACA ACA ACA 3024
     E   I   V   I   T   E   K   D   G   I   K   T   T   T
```

FIG. 4D

```
3025 TGT AAA AAT ACC ACA AAA ACA ACA TGT GAC ACT AAC AAT AAG 3066
      C   K   N   T   T   K   T   T   C   D   T   N   N   K

3067 AGA ATA GAA GAT GCA CGT AAA GCA TTC ATT GAA GGA AAA GAA 3108
      R   I   E   D   A   R   K   A   F   I   E   G   K   E

3109 GGA ATT GAG CAA GTA GAA TGT GCA AGT ACT GTT TGT CAA AAT 3150
      G   I   E   Q   V   E   C   A   S   T   V   C   Q   N

3151 GAT AAT AGT TGT CCA ATT ATT ACT GAT GTA GAA AAA TGT AAT 3192
      D   N   S   C   P   I   I   T   D   V   E   K   C   N

3193 CAA AAC ACA GAA GTA GAT TAT GGA TGT AAA GCA ATG ACA GGA 3234
      Q   N   T   E   V   D   Y   G   C   K   A   M   T   G

3235 GAA TGT GAT GGT ACT ACA TAT CTT TGT AAA TTT GTA CAA CTT 3276
      E   C   D   G   T   T   Y   L   C   K   F   V   Q   L

3277 ACT GAT GAT CCA TCA TTA GAT AGT GAA CAT TTT AGA ACT AAA 3318
      T   D   D   P   S   L   D   S   E   H   F   R   T   K

3319 TCA GGA GTT GAA CTT AAC AAT GCA TGT TTG AAA TAT AAA TGT 3360
      S   G   V   E   L   N   N   A   C   L   K   Y   K   C

3361 GTT GAG AGT AAA GGA AGT GAT GGA AAA ATC ACA CAT AAA TGG 3402
      V   E   S   K   G   S   D   G   K   I   T   H   K   W

3403 GAA ATT GAT ACA GAA CGA TCA AAT GCT AAT CCA AAA CCA AGA 3444
      E   I   D   T   E   R   S   N   A   N   P   K   P   R

3445 AAT CCA TGC GAA ACC GCA ACA TGT AAT CAA ACA ACT GGA GAA 3486
      N   P   C   E   T   A   T   C   N   Q   T   T   G   E

3487 ACT ATT TAC ACA AAG AAA ACA TGT ACT GTT TCA GAA GAA TTC 3528
      T   I   Y   T   K   K   T   C   T   V   S   E   E   F

3529 CCA ACA ATC ACA CCA AAT CAA GGA AGA TGT TTC TAT TGT CAA 3570
      P   T   I   T   P   N   Q   G   R   C   F   Y   C   Q

3571 TGT TCA TAT CTT GAC GGT TCA TCA GTT CTT ACT ATG TAT GGA 3612
      C   S   Y   L   D   G   S   S   V   L   T   M   Y   G

3613 GAA ACA GAT AAA GAA TAT TAT GAT CTT GAT GCA TGT GGT AAT 3654
      E   T   D   K   E   Y   Y   D   L   D   A   C   G   N

3655 TGT CGT GTT TGG AAT CAG ACA GAT AGA ACA CAA CAA CTT AAT 3696
      C   R   V   W   N   Q   T   D   R   T   Q   Q   L   N

3697 AAT CAC ACC GAG TGT ATT CTC GCA GGA GAA ATT AAT AAT GTT 3738
      N   H   T   E   C   I   L   A   G   E   I   N   N   V

3739 GGA GCT ATT GCA GCG GCA ACT ACT GTG GCT GTA GTT GTA GTT 3780
      G   A   I   A   A   A   T   T   V   A   V   V   V   V
```

FIG. 4E

```
3781 GCA GTC GTA GTT GCA TTA ATT GTT GTT TCT ATT GGA TTA TTT 3822
     A   V   V   V   A   L   I   V   V   S   I   G   L   F

3823 AAG ACT TAT CAA CTT GTT TCA TCA GCT ATG AAG AAT GCC ATT 3864
     K   T   Y   Q   L   V   S   S   A   M   K   N   A   I

3865 ACA ATA ACT AAT GAA AAT GCA GAA TAT GTT GGA GCA GAT AAT 3906
     T   I   T   N   E   N   A   E   Y   V   G   A   D   N

3907 GAA GCA ACT AAT GCA GCA ACA TTC AAT GGA TAA GAA CAA TAA 3948
     E   A   T   N   A   A   T   F   N   G   Z

3949 TTA AGA GAA TTG AAT AAC ATT TTA TGT TTT TAG ATT AAA AAT 3990

3991 AAA AAG AAG AAT AAA TTG AGT GAT AAA CAA TGA ATA AAA TAA 4032

4033 ATA AAA ATA AAC AAG AAT AAA GTG AAC ATC ATT TTT ATT TTC 4074

4075 ATA TTT TAA CAA CAC T 4090
```

FIG. 4F

```
 -15  MKLLLNILL  LCCLADKLNE  FSADIDYYDL  GIMSRGKNAG  SWYHSYEHQY  DVFYYLAMQP  WRHFVWTTCT  TTDGNKECYK
  66  YTINEDHNVK  VEDINKTDIK  QDFCQKEYAY  PIEKYEVDWD  NVPVDEQRIE  SVDINGKTCF  KYAAKRPLAY  VYLNTKMTYA
 146  TKTEAYDVCR  MDFIGGRSIT  FRSFNTENKA  FIDQYNTNTT  SKCLLKVYDN  NVNTHLAIIF  GITDSTYIKS  LQENLSLLNK
 226  LTTVKGVTLY  YLKDDTYFTV  NITLNDLKYE  TLVQYTAGTG  QVDPLINIAK  NDLTAKVADK  SKDKNANDKI  KRGTMIVLMD
 306  TALGSEFNAE  TEFDRKNISV  HTVVLNRRKD  PKITRSALRL  VSLGPHYHEF  TGNDEVNATI  TALFKGIRAN  LTERCDRDKC
 386  SGFCDAMNRC  TCPMCCENDC  FYTSCDVETG  DQKPSSDGYC  KAKKECPATC  VGSYECRDLE  GCVVKQYNTS  CEPKVKCMVP
 466  YCDNDKNLTE  VCKQKANCEA  DQKPSSDGYC  WSYTCDQTTG  FCKKDKRGEN  MCTGKTNNCQ  EYVCDEKQRC  TVQEKVCVKT
 546  SPYIEMSCYV  AKCNLNTGMC  ENRLSCDTYS  SCGGDSTGSV  CKCDSTTNNQ  CQCTQVKNGN  YCDSNKHQIC  DYTGKTPQCK
 626  VSNCTEDLVR  LSCLIKRCNE  TSKTTYWENV  DCSKTEVKFA  QDGKSENMCK  QYYSTTCLNG  QCVVQAVGDV  SNVGGYCSM
 706  GTDNIITYHD  DCNSRKSQCG  NFNGKCVENS  DKSYSCVFNK  ENGKEYKYTI  PKDCVNEQCI  ECKTCSLIET  REKVQEVDLC
 786  VQPTPACSVC  ESGKFVEKCK  DQKLERKVTL  EEFMKEADKE  AYCTYEITTR  ECKTCSLIET  REKVQEVDLC  FKCKNNNCII
 866  TYHYSSLFNL  TSYKLHLPQS  EEFMKEADKE  AYCTYEITTR  NTTKTTCDTN  NKRIEDARKA  FIEGKEGIEQ  VECASTVCQN  DNSCPIITDV
 946  DPNFDCQPIE  CKIQEIVITE  KDGIKTTTCK  NTTKTTCDTN  NKRIEDARKA  FIEGKEGIEQ  VECASTVCQN  DNSCPIITDV
1026  EKCNQNTEVD  YGCKAMTGEC  DGTTYLCKFV  QLTDDPSLDS  EHFRTKSGVE  LNNACLKYKC  VESKGSDGKI  THKWEIDTER
1106  SNANPKPRNP  CETATCNQTT  GETIYTKKTC  TVSEEFPTIT  PNQGRCFYCQ  CSYLDGSSVL  TMYGETDKEY  YDLDACGNCR
1186  VWNQTDRTQQ  LNNHTECILA  GEINNVGAIA  AATTVAVVVV  AVVVALIVVS  IGLFKTYQLV  SSAMKNAITI  TNENAEYVGA
1266  DNEATNAATF  NG
```

FIG. 5

SEQUENCE LISTING (1) GENERAL INFORMATION:

(iii) NUMBER OF SEQUENCES: 12

(2) INFORMATION FOR SEQ ID NO:1:

(i) SEQUENCE CHARACTERISTICS:
      (A) LENGTH: 3892 base pairs
      (B) TYPE: nucleic acid
      (C) STRANDEDNESS: single
      (D) TOPOLOGY: linear (ix) FEATURE:
      (A) NAME/KEY: CDS
      (B) LOCATION: join(1..3873, 3877..3882, 3886..3891)

(xi) SEQUENCE DESCRIPTION: SEQ ID NO:1:

```
ATG AAA TTA TTA TTA TTA AAT ATC TTA TTA TTA TGT TGT CTT GCA GAT       48
Met Lys Leu Leu Leu Leu Asn Ile Leu Leu Leu Cys Cys Leu Ala Asp
 1               5                  10                  15

AAA CTT GAT GAA TTT TCA GCA GAT AAT GAC TAT TAT GAC GGT GGT ATT       96
Lys Leu Asp Glu Phe Ser Ala Asp Asn Asp Tyr Tyr Asp Gly Gly Ile
             20                  25                  30

ATG TCT CGT GGA AAG AAT GCA GGT TCA TGG TAT CAT TCT TAC ACT CAC      144
Met Ser Arg Gly Lys Asn Ala Gly Ser Trp Tyr His Ser Tyr Thr His
         35                  40                  45

CAA TAT GAT GTT TTC TAT TAT TTA GCT ATG CAA CCA TGG AGA CAT TTT      192
Gln Tyr Asp Val Phe Tyr Tyr Leu Ala Met Gln Pro Trp Arg His Phe
     50                  55                  60

GTA TGG ACT ACA TGC GAT AAA AAT GAT AAT ACA GAA TGT TAT AAA TAT      240
Val Trp Thr Thr Cys Asp Lys Asn Asp Asn Thr Glu Cys Tyr Lys Tyr
 65                  70                  75                  80

ACT ATC AAT GAA GAT CAT AAT GTA AAG GTT GAA GAT ATT AAT AAA ACA      288
Thr Ile Asn Glu Asp His Asn Val Lys Val Glu Asp Ile Asn Lys Thr
                 85                  90                  95

AAT ATT AAA CAA GAT TTT TGT CAA AAA GAA TAT GCA TAT CCA ATT GAA      336
Asn Ile Lys Gln Asp Phe Cys Gln Lys Glu Tyr Ala Tyr Pro Ile Glu
            100                 105                 110

AAA TAT GAA GTT GAT TGG GAC AAT GTT CCA GTT GAT GAA CAA CGA ATT      384
Lys Tyr Glu Val Asp Trp Asp Asn Val Pro Val Asp Glu Gln Arg Ile
        115                 120                 125

GAA AGT GTA GAT ATT AAT GGA AAA ACT TGT TTT AAA TAT GCA GCT AAA      432
Glu Ser Val Asp Ile Asn Gly Lys Thr Cys Phe Lys Tyr Ala Ala Lys
    130                 135                 140

AGA CCA TTG GCT TAT GTT TAT TTA AAT ACA AAA ATG ACA TAT GCA ACA      480
Arg Pro Leu Ala Tyr Val Tyr Leu Asn Thr Lys Met Thr Tyr Ala Thr
145                 150                 155                 160

AAA ACT GAA GCA TAT GAT GTT TGT AGA ATG GAT TTC ATT GGA GGA AGA      528
Lys Thr Glu Ala Tyr Asp Val Cys Arg Met Asp Phe Ile Gly Gly Arg
                165                 170                 175

TCA ATT ACA TTC AGA TCA TTT AAC ACA GAG AAT AAA GCA TTT ATT GAT      576
Ser Ile Thr Phe Arg Ser Phe Asn Thr Glu Asn Lys Ala Phe Ile Asp
            180                 185                 190

CAA TAT AAT ACA AAC ACT ACA TCA AAA TGT CTT CTT AAT GTA TAT GAT      624
Gln Tyr Asn Thr Asn Thr Thr Ser Lys Cys Leu Leu Asn Val Tyr Asp
        195                 200                 205

AAT AAT GTT AAT ACA CAT CTT GCA ATT ATC TTT GGT ATT ACT GAT TCT      672
Asn Asn Val Asn Thr His Leu Ala Ile Ile Phe Gly Ile Thr Asp Ser
    210                 215                 220

ACA GTC ATT AAA TCA CTT CAA GAG AAT TTA TCT CTT TTA AGT CAA CTA      720
```

```
Thr Val Ile Lys Ser Leu Gln Glu Asn Leu Ser Leu Leu Ser Gln Leu
225                 230                 235                 240

AAA ACA GTC AAA GGA GTA ACA CTC TAC TAT CTT AAA GAT GAT ACT TAT       768
Lys Thr Val Lys Gly Val Thr Leu Tyr Tyr Leu Lys Asp Asp Thr Tyr
                245                 250                 255

TTT ACA GTT AAT ATT ACT TTA GAT CAA TTA AAA TAT GAT ACA CTT GTC       816
Phe Thr Val Asn Ile Thr Leu Asp Gln Leu Lys Tyr Asp Thr Leu Val
            260                 265                 270

AAA TAC ACA GCA GGA ACA GGA CAA GTT GAT CCA CTT ATT AAT ATT GCT       864
Lys Tyr Thr Ala Gly Thr Gly Gln Val Asp Pro Leu Ile Asn Ile Ala
        275                 280                 285

AAG AAT GAT TTA GCT ACT AAA GTT GCA GAT AAA AGT AAA GAT AAA AAT       912
Lys Asn Asp Leu Ala Thr Lys Val Ala Asp Lys Ser Lys Asp Lys Asn
    290                 295                 300

GCA AAT GAT AAA ATC AAA AGA GGA ACT ATG ATT GTG TTA ATG GAT ACT       960
Ala Asn Asp Lys Ile Lys Arg Gly Thr Met Ile Val Leu Met Asp Thr
305                 310                 315                 320

GCA CTT GGA TCA GAA TTT AAT GCA GAA ACA GAA TTT GAT AGA AAG AAT      1008
Ala Leu Gly Ser Glu Phe Asn Ala Glu Thr Glu Phe Asp Arg Lys Asn
                325                 330                 335

ATT TCA GTT CAT ACT GTT GTT CTT AAT AGA AAT AAA GAC CCA AAG ATT      1056
Ile Ser Val His Thr Val Val Leu Asn Arg Asn Lys Asp Pro Lys Ile
            340                 345                 350

ACA CGT AGT GCA TTG AGA CTT GTT TCA CTT GGA CCA CAT TAT CAT GAA      1104
Thr Arg Ser Ala Leu Arg Leu Val Ser Leu Gly Pro His Tyr His Glu
        355                 360                 365

TTT ACA GGT AAT GAT GAA GTT AAT GCA ACA ATC ACT GCA CTT TTC AAA      1152
Phe Thr Gly Asn Asp Glu Val Asn Ala Thr Ile Thr Ala Leu Phe Lys
    370                 375                 380

GGA ATT AGA GCC AAT TTA ACA GAA AGA TGT GAT AGA GAT AAA TGT TCA      1200
Gly Ile Arg Ala Asn Leu Thr Glu Arg Cys Asp Arg Asp Lys Cys Ser
385                 390                 395                 400

GGA TTT TGT GAT GCA ATG AAT AGA TGC ACA TGT CCA ATG TGT TGT GAG      1248
Gly Phe Cys Asp Ala Met Asn Arg Cys Thr Cys Pro Met Cys Cys Glu
                405                 410                 415

AAT GAT TGT TTC TAT ACA TCC TGT GAT GTA GAA ACA GGA TCA TGT ATT      1296
Asn Asp Cys Phe Tyr Thr Ser Cys Asp Val Glu Thr Gly Ser Cys Ile
            420                 425                 430

CCA TGG CCT AAA GCT AAA CCA AAA GCA AAG AAA GAA TGT CCA GCA ACA      1344
Pro Trp Pro Lys Ala Lys Pro Lys Ala Lys Lys Glu Cys Pro Ala Thr
        435                 440                 445

TGT GTA GGC TCA TAT GAA TGT AGA GAT CTT GAA GGA TGT GTT GTT ACA      1392
Cys Val Gly Ser Tyr Glu Cys Arg Asp Leu Glu Gly Cys Val Val Thr
    450                 455                 460

AAA TAT AAT GAC ACA TGC CAA CCA AAA GTG AAA TGC ATG GTA CCA TAT      1440
Lys Tyr Asn Asp Thr Cys Gln Pro Lys Val Lys Cys Met Val Pro Tyr
465                 470                 475                 480

TGT GAT AAT GAT AAG AAT CTA ACT GAA GTA TGT AAA CAA AAA GCT AAT      1488
Cys Asp Asn Asp Lys Asn Leu Thr Glu Val Cys Lys Gln Lys Ala Asn
                485                 490                 495

TGT GAA GCA GAT CAA AAA CCA AGT TCT GAT GGA TAT TGT TGG AGT TAT      1536
Cys Glu Ala Asp Gln Lys Pro Ser Ser Asp Gly Tyr Cys Trp Ser Tyr
            500                 505                 510

ACA TGT GAC CAA ACT ACT GGT TTT TGT AAG AAA GAT AAA CGA GGT AAA      1584
Thr Cys Asp Gln Thr Thr Gly Phe Cys Lys Lys Asp Lys Arg Gly Lys
        515                 520                 525

GAA ATG TGT ACA GGA AAG ACA AAT AAT TGT CAA GAA TAT GTT TGT GAT      1632
Glu Met Cys Thr Gly Lys Thr Asn Asn Cys Gln Glu Tyr Val Cys Asp
    530                 535                 540
```

```
TCA GAA CAA AGA TGT AGT GTT AGA GAT AAA GTA TGT GTA AAA ACA TCA    1680
Ser Glu Gln Arg Cys Ser Val Arg Asp Lys Val Cys Val Lys Thr Ser
545                 550                 555                 560

CCA TAC ATT GAA ATG TCA TGT TAT GTA GCC AAG TGT AAT CTC AAT ACA    1728
Pro Tyr Ile Glu Met Ser Cys Tyr Val Ala Lys Cys Asn Leu Asn Thr
                565                 570                 575

GGT ATG TGT GAG AAC AGA TTA TCA TGT GAT ACA TAC TCA TCA TGT GGT    1776
Gly Met Cys Glu Asn Arg Leu Ser Cys Asp Thr Tyr Ser Ser Cys Gly
            580                 585                 590

GGA GAT TCT ACA GGA TCA GTA TGT AAA TGT GAT TCT ACA ACT GGT AAT    1824
Gly Asp Ser Thr Gly Ser Val Cys Lys Cys Asp Ser Thr Thr Gly Asn
        595                 600                 605

AAA TGT CAA TGT AAT AAA GTA AAA AAT GGT AAT TAT TGT AAT TCT AAA    1872
Lys Cys Gln Cys Asn Lys Val Lys Asn Gly Asn Tyr Cys Asn Ser Lys
    610                 615                 620

AAC CAT GAA ATT TGT GAT TAT ACA GGA ACA ACA CCA CAA TGT AAA GTG    1920
Asn His Glu Ile Cys Asp Tyr Thr Gly Thr Thr Pro Gln Cys Lys Val
625                 630                 635                 640

TCT AAT TGT ACA GAA GAT CTT GTT AGA GAT GGA TGT CTT ATT AAG AGA    1968
Ser Asn Cys Thr Glu Asp Leu Val Arg Asp Gly Cys Leu Ile Lys Arg
                645                 650                 655

TGC AAT GAA ACA AGT AAA ACA ACA TAT TGG GAG AAT GTT GAT TGT TCA    2016
Cys Asn Glu Thr Ser Lys Thr Thr Tyr Trp Glu Asn Val Asp Cys Ser
            660                 665                 670

AAC ACT AAG ATT GAA TTT GCT AAA GAT GAT AAA TCT GAA ACT ATG TGT    2064
Asn Thr Lys Ile Glu Phe Ala Lys Asp Asp Lys Ser Glu Thr Met Cys
        675                 680                 685

AAA CAA TAT TAT TCA ACT ACA TGT TTG AAT GGA AAA TGT GTT GTT CAA    2112
Lys Gln Tyr Tyr Ser Thr Thr Cys Leu Asn Gly Lys Cys Val Val Gln
    690                 695                 700

GCA GTT GGT GAT GTT TCT AAT GTA GGA TGT GGA TAT TGT TCA ATG GGA    2160
Ala Val Gly Asp Val Ser Asn Val Gly Cys Gly Tyr Cys Ser Met Gly
705                 710                 715                 720

ACA GAT AAT ATT ATT ACA TAT CAT GAT GAT TGT AAT TCA CGT AAA TCA    2208
Thr Asp Asn Ile Ile Thr Tyr His Asp Asp Cys Asn Ser Arg Lys Ser
                725                 730                 735

CAA TGT GGA AAC TTT AAT GGT AAA TGT ATT AAA GGC AGT GAC AAT TCT    2256
Gln Cys Gly Asn Phe Asn Gly Lys Cys Ile Lys Gly Ser Asp Asn Ser
            740                 745                 750

TAT TCT TGT GTA TTT GAA AAA GAT AAA ACT TCT TCT AAA TCA GAT AAT    2304
Tyr Ser Cys Val Phe Glu Lys Asp Lys Thr Ser Ser Lys Ser Asp Asn
        755                 760                 765

GAT ATT TGT GCT GAA TGT TCT AGT TTA ACA TGT CCA GCT GAT ACT ACA    2352
Asp Ile Cys Ala Glu Cys Ser Ser Leu Thr Cys Pro Ala Asp Thr Thr
    770                 775                 780

TAC AGA ACA TAT ACA TAT GAC TCA AAA ACA GGA ACA TGT AAA GCA ACT    2400
Tyr Arg Thr Tyr Thr Tyr Asp Ser Lys Thr Gly Thr Cys Lys Ala Thr
785                 790                 795                 800

GTT CAA CCA ACA CCA GCA TGT TCA GTA TGT GAA AGT GGT AAA TTT GTA    2448
Val Gln Pro Thr Pro Ala Cys Ser Val Cys Glu Ser Gly Lys Phe Val
                805                 810                 815

GAG AAA TGC AAA GAT CAA AAA TTA GAA CGT AAA GTC ACT TTA GAA AAT    2496
Glu Lys Cys Lys Asp Gln Lys Leu Glu Arg Lys Val Thr Leu Glu Asn
            820                 825                 830

GGA AAA GAA TAT AAA TAC ACC ATT CCA AAA GAT TGT GTC AAT GAA CAA    2544
Gly Lys Glu Tyr Lys Tyr Thr Ile Pro Lys Asp Cys Val Asn Glu Gln
        835                 840                 845

TGC ATT CCA AGA ACA TAC ATA GAT TGT TTA GGT AAT GAT GAT AAC TTT    2592
Cys Ile Pro Arg Thr Tyr Ile Asp Cys Leu Gly Asn Asp Asp Asn Phe
    850                 855                 860
```

```
AAA TCT ATT TAT AAC TTC TAT TTA CCA TGT CAA GCA TAT GTT ACA GCT        2640
Lys Ser Ile Tyr Asn Phe Tyr Leu Pro Cys Gln Ala Tyr Val Thr Ala
865             870             875             880

ACC TAT CAT TAC AGT TCA TTA TTC AAT TTA ACT AGT TAT AAA CTT CAC        2688
Thr Tyr His Tyr Ser Ser Leu Phe Asn Leu Thr Ser Tyr Lys Leu His
            885             890             895

TTA CCA CAA AGT GAA GAA TTT ATG AAA GAG GCA GAC AAA GAA GCA TAT        2736
Leu Pro Gln Ser Glu Glu Phe Met Lys Glu Ala Asp Lys Glu Ala Tyr
        900             905             910

TGT ACA TAC GAA ATA ACA ACA AGA GAA TGT AAA ACA TGT TCA TTA ATT        2784
Cys Thr Tyr Glu Ile Thr Thr Arg Glu Cys Lys Thr Cys Ser Leu Ile
            915             920             925

GAA ACT AGA GAA AAA GTC CAA GAA GTT GAT TTG TGT GCA GAA GAA ACT        2832
Glu Thr Arg Glu Lys Val Gln Glu Val Asp Leu Cys Ala Glu Glu Thr
        930             935             940

AAG AAT GGA GGA GTT CCA TTC AAA TGT AAG AAT AAC AAT TGC ATT ATT        2880
Lys Asn Gly Gly Val Pro Phe Lys Cys Lys Asn Asn Asn Cys Ile Ile
945             950             955             960

GAT CCT AAC TTT GAT TGT CAA CCT ATT GAA TGT AAG ATT CAA GAG ATT        2928
Asp Pro Asn Phe Asp Cys Gln Pro Ile Glu Cys Lys Ile Gln Glu Ile
            965             970             975

GTT ATT ACA GAA AAA GAT GGA ATA AAA ACA ACA ACA TGT AAA AAT ACT        2976
Val Ile Thr Glu Lys Asp Gly Ile Lys Thr Thr Thr Cys Lys Asn Thr
        980             985             990

ACA AAA GCA ACA TGT GAC ACT AAC AAT AAG AGA ATA GAA GAT GCA CGT        3024
Thr Lys Ala Thr Cys Asp Thr Asn Asn Lys Arg Ile Glu Asp Ala Arg
            995             1000            1005

AAA GCA TTC ATT GAA GGA AAA GAA GGA ATT GAG CAA GTA GAA TGT GCA        3072
Lys Ala Phe Ile Glu Gly Lys Glu Gly Ile Glu Gln Val Glu Cys Ala
        1010            1015            1020

AGT ACT GTT TGT CAA AAT GAT AAT AGT TGT CCA ATT ATT ACT GAT GTA        3120
Ser Thr Val Cys Gln Asn Asp Asn Ser Cys Pro Ile Ile Thr Asp Val
1025            1030            1035            1040

GAA AAA TGT AAT CAA AAC ACA GAA GTA GAT TAT GGA TGT AAA GCA ATG        3168
Glu Lys Cys Asn Gln Asn Thr Glu Val Asp Tyr Gly Cys Lys Ala Met
            1045            1050            1055

ACA GGA GAA TGT GAT GGT ACT ACA TAT CTT TGT AAA TTT GTA CAA CTT        3216
Thr Gly Glu Cys Asp Gly Thr Thr Tyr Leu Cys Lys Phe Val Gln Leu
        1060            1065            1070

ACT GAT GAT CCA TCA TTA GAT AGT GAA CAT TTT AGA ACT AAA TCA GGA        3264
Thr Asp Asp Pro Ser Leu Asp Ser Glu His Phe Arg Thr Lys Ser Gly
            1075            1080            1085

GTT GAA CTT AAC AAT GCA TGT TTG AAA TAT AAA TGT GTT GAG AGT AAA        3312
Val Glu Leu Asn Asn Ala Cys Leu Lys Tyr Lys Cys Val Glu Ser Lys
        1090            1095            1100

GGA AGT GAT GGA AAA ATC ACA CAT AAA TGG GAA ATT GAT ACA GAA CGA        3360
Gly Ser Asp Gly Lys Ile Thr His Lys Trp Glu Ile Asp Thr Glu Arg
1105            1110            1115            1120

TCA AAT GCT AAT CCA AAA CCA AGA AAT CCA TGC GAA ACC GCA ACA TGT        3408
Ser Asn Ala Asn Pro Lys Pro Arg Asn Pro Cys Glu Thr Ala Thr Cys
            1125            1130            1135

AAT CAA ACA ACT GGA GAA ACT ATT TAC ACA AAG AAA ACA TGT ACT GTT        3456
Asn Gln Thr Thr Gly Glu Thr Ile Tyr Thr Lys Lys Thr Cys Thr Val
        1140            1145            1150

TCA GAA TTC CCA ACA ATC ACA CCA AAT CAA GGA AGA TGT TTC TAT TGT        3504
Ser Glu Phe Pro Thr Ile Thr Pro Asn Gln Gly Arg Cys Phe Tyr Cys
            1155            1160            1165

CAA TGT TCA TAT CTT GAC GGT TCA TCA GTT CTT ACT ATG TAT GGA GAA        3552
Gln Cys Ser Tyr Leu Asp Gly Ser Ser Val Leu Thr Met Tyr Gly Glu
```

-continued

```
       1170                1175                1180
ACA GAT AAA GAA TAT TAT GAT CTT GAT GCA TGT GGT AAT TGT CGT GTT    3600
Thr Asp Lys Glu Tyr Tyr Asp Leu Asp Ala Cys Gly Asn Cys Arg Val
1185                1190                1195                1200

TGG AAT CAG ACA GAT AGA ACA CAA CAA CTT AAT AAT CAC ACC GAG TGT    3648
Trp Asn Gln Thr Asp Arg Thr Gln Gln Leu Asn Asn His Thr Glu Cys
                1205                1210                1215

ATT CTC GCA GGA GAA ATT AAT AAT GTT GGA GCT ATT GCA GCG GCA ACT    3696
Ile Leu Ala Gly Glu Ile Asn Asn Val Gly Ala Ile Ala Ala Ala Thr
            1220                1225                1230

ACT GTG GCT GCT GTT ATA GTT GCA GTT GTA GTT GCA TTA ATT GTT GTT    3744
Thr Val Ala Ala Val Ile Val Ala Val Val Val Ala Leu Ile Val Val
        1235                1240                1245

TCT ATT GGA TTA TTT AAG ACT TAT CAA CTT GTT TCA TCA GCT ATG AAG    3792
Ser Ile Gly Leu Phe Lys Thr Tyr Gln Leu Val Ser Ser Ala Met Lys
    1250                1255                1260

AAT GCC ATT ACA ATA ACT AAT GAA AAT GCA GAA TAT GTT GGA GCA GAT    3840
Asn Ala Ile Thr Ile Thr Asn Glu Asn Ala Glu Tyr Val Gly Ala Asp
1265                1270                1275                1280

AAT GAA GCA ACT AAT GCA GCA ACA TTC AAT GGA TAAGAACAAT AATTAAGCC   3892
Asn Glu Ala Thr Asn Ala Ala Thr Phe Asn Gly
                1285                1290
```

(2) INFORMATION FOR SEQ ID NO:2:

(i) SEQUENCE CHARACTERISTICS:
        (A) LENGTH: 1291 amino acids
        (B) TYPE: amino acid
        (D) TOPOLOGY: linear (ii) MOLECULE TYPE: protein (xi) SEQUENCE DESCRIPTION: SEQ ID NO:2:

```
Met Lys Leu Leu Leu Leu Asn Ile Leu Leu Leu Cys Cys Leu Ala Asp
 1               5                  10                  15

Lys Leu Asp Glu Phe Ser Ala Asp Asn Asp Tyr Tyr Asp Gly Gly Ile
             20                  25                  30

Met Ser Arg Gly Lys Asn Ala Gly Ser Trp Tyr His Ser Tyr Thr His
         35                  40                  45

Gln Tyr Asp Val Phe Tyr Tyr Leu Ala Met Gln Pro Trp Arg His Phe
     50                  55                  60

Val Trp Thr Thr Cys Asp Lys Asn Asp Asn Thr Glu Cys Tyr Lys Tyr
 65                  70                  75                  80

Thr Ile Asn Glu Asp His Asn Val Lys Val Glu Asp Ile Asn Lys Thr
                 85                  90                  95

Asn Ile Lys Gln Asp Phe Cys Gln Lys Glu Tyr Ala Tyr Pro Ile Glu
            100                 105                 110

Lys Tyr Glu Val Asp Trp Asp Asn Val Pro Val Asp Glu Gln Arg Ile
        115                 120                 125

Glu Ser Val Asp Ile Asn Gly Lys Thr Cys Phe Lys Tyr Ala Ala Lys
130                 135                 140

Arg Pro Leu Ala Tyr Val Tyr Leu Asn Thr Lys Met Thr Tyr Ala Thr
145                 150                 155                 160

Lys Thr Glu Ala Tyr Asp Val Cys Arg Met Asp Phe Ile Gly Gly Arg
                165                 170                 175

Ser Ile Thr Phe Arg Ser Phe Asn Thr Glu Asn Lys Ala Phe Ile Asp
            180                 185                 190

Gln Tyr Asn Thr Asn Thr Thr Ser Lys Cys Leu Leu Asn Val Tyr Asp
```

-continued

```
                195                 200                 205
Asn Asn Val Asn Thr His Leu Ala Ile Ile Phe Gly Ile Thr Asp Ser
            210                 215                 220
Thr Val Ile Lys Ser Leu Gln Glu Asn Leu Ser Leu Ser Gln Leu
225                 230                 235                 240
Lys Thr Val Lys Gly Val Thr Leu Tyr Tyr Leu Lys Asp Asp Thr Tyr
                245                 250                 255
Phe Thr Val Asn Ile Thr Leu Asp Gln Leu Lys Tyr Asp Thr Leu Val
            260                 265                 270
Lys Tyr Thr Ala Gly Thr Gly Gln Val Asp Pro Leu Ile Asn Ile Ala
            275                 280                 285
Lys Asn Asp Leu Ala Thr Lys Val Ala Asp Lys Ser Lys Asp Lys Asn
            290                 295                 300
Ala Asn Asp Lys Ile Lys Arg Gly Thr Met Ile Val Leu Met Asp Thr
305                 310                 315                 320
Ala Leu Gly Ser Glu Phe Asn Ala Glu Thr Glu Phe Asp Arg Lys Asn
                325                 330                 335
Ile Ser Val His Thr Val Val Leu Asn Arg Asn Lys Asp Pro Lys Ile
            340                 345                 350
Thr Arg Ser Ala Leu Arg Leu Val Ser Leu Gly Pro His Tyr His Glu
            355                 360                 365
Phe Thr Gly Asn Asp Glu Val Asn Ala Thr Ile Thr Ala Leu Phe Lys
            370                 375                 380
Gly Ile Arg Ala Asn Leu Thr Glu Arg Cys Asp Arg Asp Lys Cys Ser
385                 390                 395                 400
Gly Phe Cys Asp Ala Met Asn Arg Cys Thr Cys Pro Met Cys Cys Glu
                405                 410                 415
Asn Asp Cys Phe Tyr Thr Ser Cys Asp Val Glu Thr Gly Ser Cys Ile
                420                 425                 430
Pro Trp Pro Lys Ala Lys Pro Lys Ala Lys Glu Cys Pro Ala Thr
            435                 440                 445
Cys Val Gly Ser Tyr Glu Cys Arg Asp Leu Glu Gly Cys Val Val Thr
            450                 455                 460
Lys Tyr Asn Asp Thr Cys Gln Pro Lys Val Lys Cys Met Val Pro Tyr
465                 470                 475                 480
Cys Asp Asn Asp Lys Asn Leu Thr Glu Val Cys Lys Gln Lys Ala Asn
                485                 490                 495
Cys Glu Ala Asp Gln Lys Pro Ser Ser Asp Gly Tyr Cys Trp Ser Tyr
                500                 505                 510
Thr Cys Asp Gln Thr Thr Gly Phe Cys Lys Lys Asp Lys Arg Gly Lys
            515                 520                 525
Glu Met Cys Thr Gly Lys Thr Asn Asn Cys Gln Glu Tyr Val Cys Asp
            530                 535                 540
Ser Glu Gln Arg Cys Ser Val Arg Asp Lys Val Cys Val Lys Thr Ser
545                 550                 555                 560
Pro Tyr Ile Glu Met Ser Cys Tyr Val Ala Lys Cys Asn Leu Asn Thr
                565                 570                 575
Gly Met Cys Glu Asn Arg Leu Ser Cys Asp Thr Tyr Ser Ser Cys Gly
            580                 585                 590
Gly Asp Ser Thr Gly Ser Val Cys Lys Cys Asp Ser Thr Thr Gly Asn
            595                 600                 605
Lys Cys Gln Cys Asn Lys Val Lys Asn Gly Asn Tyr Cys Asn Ser Lys
            610                 615                 620
```

-continued

```
Asn His Glu Ile Cys Asp Tyr Thr Gly Thr Pro Gln Cys Lys Val
625                 630                 635                 640

Ser Asn Cys Thr Glu Asp Leu Val Arg Asp Gly Cys Leu Ile Lys Arg
            645                 650                 655

Cys Asn Glu Thr Ser Lys Thr Thr Tyr Trp Glu Asn Val Asp Cys Ser
                660                 665                 670

Asn Thr Lys Ile Glu Phe Ala Lys Asp Lys Ser Glu Thr Met Cys
            675                 680                 685

Lys Gln Tyr Tyr Ser Thr Thr Cys Leu Asn Gly Lys Cys Val Val Gln
690                 695                 700

Ala Val Gly Asp Val Ser Asn Val Gly Cys Gly Tyr Cys Ser Met Gly
705                 710                 715                 720

Thr Asp Asn Ile Ile Thr Tyr His Asp Asp Cys Asn Ser Arg Lys Ser
                725                 730                 735

Gln Cys Gly Asn Phe Asn Gly Lys Cys Ile Lys Gly Ser Asp Asn Ser
            740                 745                 750

Tyr Ser Cys Val Phe Glu Lys Asp Lys Thr Ser Ser Lys Ser Asp Asn
            755                 760                 765

Asp Ile Cys Ala Glu Cys Ser Ser Leu Thr Cys Pro Ala Asp Thr Thr
770                 775                 780

Tyr Arg Thr Tyr Thr Tyr Asp Ser Lys Thr Gly Thr Cys Lys Ala Thr
785                 790                 795                 800

Val Gln Pro Thr Pro Ala Cys Ser Val Cys Glu Ser Gly Lys Phe Val
                805                 810                 815

Glu Lys Cys Lys Asp Gln Lys Leu Glu Arg Lys Val Thr Leu Glu Asn
            820                 825                 830

Gly Lys Glu Tyr Lys Tyr Thr Ile Pro Lys Asp Cys Val Asn Glu Gln
            835                 840                 845

Cys Ile Pro Arg Thr Tyr Ile Asp Cys Leu Gly Asn Asp Asp Asn Phe
850                 855                 860

Lys Ser Ile Tyr Asn Phe Tyr Leu Pro Cys Gln Ala Tyr Val Thr Ala
865                 870                 875                 880

Thr Tyr His Tyr Ser Ser Leu Phe Asn Leu Thr Ser Tyr Lys Leu His
                885                 890                 895

Leu Pro Gln Ser Glu Glu Phe Met Lys Glu Ala Asp Lys Glu Ala Tyr
            900                 905                 910

Cys Thr Tyr Glu Ile Thr Thr Arg Glu Cys Lys Thr Cys Ser Leu Ile
            915                 920                 925

Glu Thr Arg Glu Lys Val Gln Glu Val Asp Leu Cys Ala Glu Glu Thr
930                 935                 940

Lys Asn Gly Gly Val Pro Phe Lys Cys Lys Asn Asn Cys Ile Ile
945                 950                 955                 960

Asp Pro Asn Phe Asp Cys Gln Pro Ile Glu Cys Lys Ile Gln Glu Ile
                965                 970                 975

Val Ile Thr Glu Lys Asp Gly Ile Lys Thr Thr Thr Cys Lys Asn Thr
            980                 985                 990

Thr Lys Ala Thr Cys Asp Thr Asn Asn Lys Arg Ile Glu Asp Ala Arg
            995                 1000                1005

Lys Ala Phe Ile Glu Gly Lys Glu Gly Ile Glu Gln Val Glu Cys Ala
        1010                1015                1020

Ser Thr Val Cys Gln Asn Asp Asn Ser Cys Pro Ile Ile Thr Asp Val
1025                1030                1035                1040
```

```
Glu Lys Cys Asn Gln Asn Thr Glu Val Asp Tyr Gly Cys Lys Ala Met
            1045                1050                1055

Thr Gly Glu Cys Asp Gly Thr Thr Tyr Leu Cys Lys Phe Val Gln Leu
            1060                1065                1070

Thr Asp Pro Ser Leu Asp Ser Glu His Phe Arg Thr Lys Ser Gly
            1075                1080                1085

Val Glu Leu Asn Asn Ala Cys Leu Lys Tyr Lys Cys Val Glu Ser Lys
            1090                1095                1100

Gly Ser Asp Gly Lys Ile Thr His Lys Trp Glu Ile Asp Thr Glu Arg
1105                1110                1115                1120

Ser Asn Ala Asn Pro Lys Pro Arg Asn Pro Cys Glu Thr Ala Thr Cys
            1125                1130                1135

Asn Gln Thr Thr Gly Glu Thr Ile Tyr Thr Lys Lys Thr Cys Thr Val
            1140                1145                1150

Ser Glu Phe Pro Thr Ile Thr Pro Asn Gln Gly Arg Cys Phe Tyr Cys
            1155                1160                1165

Gln Cys Ser Tyr Leu Asp Gly Ser Ser Val Leu Thr Met Tyr Gly Glu
            1170                1175                1180

Thr Asp Lys Glu Tyr Tyr Asp Leu Asp Ala Cys Gly Asn Cys Arg Val
1185                1190                1195                1200

Trp Asn Gln Thr Asp Arg Thr Gln Gln Leu Asn Asn His Thr Glu Cys
            1205                1210                1215

Ile Leu Ala Gly Glu Ile Asn Asn Val Gly Ala Ile Ala Ala Thr
            1220                1225                1230

Thr Val Ala Ala Val Ile Val Ala Val Val Ala Leu Ile Val Val
            1235                1240                1245

Ser Ile Gly Leu Phe Lys Thr Tyr Gln Leu Val Ser Ser Ala Met Lys
            1250                1255                1260

Asn Ala Ile Thr Ile Thr Asn Glu Asn Ala Glu Tyr Val Gly Ala Asp
1265                1270                1275                1280

Asn Glu Ala Thr Asn Ala Ala Thr Phe Asn Gly
            1285                1290

(2) INFORMATION FOR SEQ ID NO:3:

(i) SEQUENCE CHARACTERISTICS:
        (A) LENGTH: 1276 amino acids
        (B) TYPE: amino acid
        (C) STRANDEDNESS: single
        (D) TOPOLOGY: linear (xi) SEQUENCE DESCRIPTION: SEQ ID NO:3:

Asp Lys Leu Asp Glu Phe Ser Ala Asp Asn Asp Tyr Tyr Asp Gly Gly
1               5                   10                  15

Ile Met Ser Arg Gly Lys Asn Ala Gly Ser Trp Tyr His Ser Tyr Thr
            20                  25                  30

His Gln Tyr Asp Val Phe Tyr Tyr Leu Ala Met Gln Pro Trp Arg His
        35                  40                  45

Phe Val Trp Thr Thr Cys Asp Lys Asn Asp Asn Thr Glu Cys Tyr Lys
    50                  55                  60

Tyr Thr Ile Asn Glu Asp His Asn Val Lys Val Glu Asp Ile Asn Lys
65              70                  75                  80

Thr Asn Ile Lys Gln Asp Phe Cys Gln Lys Glu Tyr Ala Tyr Pro Ile
                85                  90                  95

Glu Lys Tyr Glu Val Asp Trp Asp Asn Val Pro Val Asp Glu Gln Arg
            100                 105                 110
```

-continued

```
Ile Glu Ser Val Asp Ile Asn Gly Lys Thr Cys Phe Lys Tyr Ala Ala
        115                 120                 125

Lys Arg Pro Leu Ala Tyr Val Tyr Leu Asn Thr Lys Met Thr Tyr Ala
        130                 135                 140

Thr Lys Thr Glu Ala Tyr Asp Val Cys Arg Met Asp Phe Ile Gly Gly
145                 150                 155                 160

Arg Ser Ile Thr Phe Arg Ser Phe Asn Thr Glu Asn Lys Ala Phe Ile
                165                 170                 175

Asp Gln Tyr Asn Thr Asn Thr Ser Lys Cys Leu Leu Asn Val Tyr
            180                 185                 190

Asp Asn Asn Val Asn Thr His Leu Ala Ile Ile Phe Gly Ile Thr Asp
            195                 200                 205

Ser Thr Val Ile Lys Ser Leu Gln Glu Asn Leu Ser Leu Leu Ser Gln
210                 215                 220

Leu Lys Thr Val Lys Gly Val Thr Leu Tyr Tyr Leu Lys Asp Asp Thr
225                 230                 235                 240

Tyr Phe Thr Val Asn Ile Thr Leu Asp Gln Leu Lys Tyr Asp Thr Leu
                245                 250                 255

Val Lys Tyr Thr Ala Gly Thr Gly Gln Val Asp Pro Leu Ile Asn Ile
            260                 265                 270

Ala Lys Asn Asp Leu Ala Thr Lys Val Ala Asp Lys Ser Lys Asp Lys
            275                 280                 285

Asn Ala Asn Asp Lys Ile Lys Arg Gly Thr Met Ile Val Leu Met Asp
            290                 295                 300

Thr Ala Leu Gly Ser Glu Phe Asn Ala Glu Thr Glu Phe Asp Arg Lys
305                 310                 315                 320

Asn Ile Ser Val His Thr Val Leu Asn Arg Asn Lys Asp Pro Lys
                325                 330                 335

Ile Thr Arg Ser Ala Leu Arg Leu Val Ser Leu Gly Pro His Tyr His
            340                 345                 350

Glu Phe Thr Gly Asn Asp Glu Val Asn Ala Thr Ile Thr Ala Leu Phe
        355                 360                 365

Lys Gly Ile Arg Ala Asn Leu Thr Glu Arg Cys Asp Arg Asp Lys Cys
        370                 375                 380

Ser Gly Phe Cys Asp Ala Met Asn Arg Cys Thr Cys Pro Met Cys Cys
385                 390                 395                 400

Glu Asn Asp Cys Phe Tyr Thr Ser Cys Asp Val Glu Thr Gly Ser Cys
                405                 410                 415

Ile Pro Trp Pro Lys Ala Lys Pro Lys Ala Lys Lys Glu Cys Pro Ala
            420                 425                 430

Thr Cys Val Gly Ser Tyr Glu Cys Arg Asp Leu Glu Gly Cys Val Val
        435                 440                 445

Thr Lys Tyr Asn Asp Thr Cys Gln Pro Lys Val Lys Cys Met Val Pro
        450                 455                 460

Tyr Cys Asp Asn Asp Lys Asn Leu Thr Glu Val Cys Lys Gln Lys Ala
465                 470                 475                 480

Asn Cys Glu Ala Asp Gln Lys Pro Ser Ser Asp Gly Tyr Cys Trp Ser
            485                 490                 495

Tyr Thr Cys Asp Gln Thr Thr Gly Phe Cys Lys Lys Asp Lys Arg Gly
                500                 505                 510

Lys Glu Met Cys Thr Gly Lys Thr Asn Asn Cys Gln Glu Tyr Val Cys
            515                 520                 525
```

-continued

```
Asp Ser Glu Gln Arg Cys Ser Val Arg Asp Lys Val Cys Val Lys Thr
        530                 535                 540
Ser Pro Tyr Ile Glu Met Ser Cys Tyr Val Ala Lys Cys Asn Leu Asn
545                 550                 555                 560
Thr Gly Met Cys Glu Asn Arg Leu Ser Cys Asp Thr Tyr Ser Ser Cys
                    565                 570                 575
Gly Gly Asp Ser Thr Gly Ser Val Cys Lys Cys Asp Ser Thr Thr Gly
                580                 585                 590
Asn Lys Cys Gln Cys Asn Lys Val Lys Asn Gly Asn Tyr Cys Asn Ser
            595                 600                 605
Lys Asn His Glu Ile Cys Asp Tyr Thr Gly Thr Thr Pro Gln Cys Lys
        610                 615                 620
Val Ser Asn Cys Thr Glu Asp Leu Val Arg Asp Gly Cys Leu Ile Lys
625                 630                 635                 640
Arg Cys Asn Glu Thr Ser Lys Thr Thr Tyr Trp Glu Asn Val Asp Cys
                    645                 650                 655
Ser Asn Thr Lys Ile Glu Phe Ala Lys Asp Asp Lys Ser Glu Thr Met
                660                 665                 670
Cys Lys Gln Tyr Tyr Ser Thr Thr Cys Leu Asn Gly Lys Cys Val Val
            675                 680                 685
Gln Ala Val Gly Asp Val Ser Asn Val Gly Cys Gly Tyr Cys Ser Met
        690                 695                 700
Gly Thr Asp Asn Ile Ile Thr Tyr His Asp Asp Cys Asn Ser Arg Lys
705                 710                 715                 720
Ser Gln Cys Gly Asn Phe Asn Gly Lys Cys Ile Lys Gly Ser Asp Asn
                    725                 730                 735
Ser Tyr Ser Cys Val Phe Glu Lys Asp Lys Thr Ser Ser Lys Ser Asp
                740                 745                 750
Asn Asp Ile Cys Ala Glu Cys Ser Ser Leu Thr Cys Pro Ala Asp Thr
            755                 760                 765
Thr Tyr Arg Thr Tyr Thr Tyr Asp Ser Lys Thr Gly Thr Cys Lys Ala
        770                 775                 780
Thr Val Gln Pro Thr Pro Ala Cys Ser Val Cys Glu Ser Gly Lys Phe
785                 790                 795                 800
Val Glu Lys Cys Lys Asp Gln Lys Leu Glu Arg Lys Val Thr Leu Glu
                    805                 810                 815
Asn Gly Lys Glu Tyr Lys Tyr Thr Ile Pro Lys Asp Cys Val Asn Glu
                820                 825                 830
Gln Cys Ile Pro Arg Thr Tyr Ile Asp Cys Leu Gly Asn Asp Asp Asn
            835                 840                 845
Phe Lys Ser Ile Tyr Asn Phe Tyr Leu Pro Cys Gln Ala Tyr Val Thr
        850                 855                 860
Ala Thr Tyr His Tyr Ser Ser Leu Phe Asn Leu Thr Ser Tyr Lys Leu
865                 870                 875                 880
His Leu Pro Gln Ser Glu Glu Phe Met Lys Glu Ala Asp Lys Glu Ala
                    885                 890                 895
Tyr Cys Thr Tyr Glu Ile Thr Thr Arg Glu Cys Lys Thr Cys Ser Leu
                900                 905                 910
Ile Glu Thr Arg Glu Lys Val Gln Glu Val Asp Leu Cys Ala Glu Glu
            915                 920                 925
Thr Lys Asn Gly Gly Val Pro Phe Lys Cys Lys Asn Asn Asn Cys Ile
        930                 935                 940
Ile Asp Pro Asn Phe Asp Cys Gln Pro Ile Glu Cys Lys Ile Gln Glu
```

```
                                         945              950              955              960

Ile Val Ile Thr Glu Lys Asp Gly Ile Lys Thr Thr Cys Lys Asn
                    965              970              975

Thr Thr Lys Ala Thr Cys Asp Thr Asn Asn Lys Arg Ile Glu Asp Ala
                980              985              990

Arg Lys Ala Phe Ile Glu Gly Lys Glu Gly Ile Glu Gln Val Glu Cys
            995             1000             1005

Ala Ser Thr Val Cys Gln Asn Asp Asn Ser Cys Pro Ile Ile Thr Asp
           1010             1015             1020

Val Glu Lys Cys Asn Gln Asn Thr Glu Val Asp Tyr Gly Cys Lys Ala
1025             1030             1035             1040

Met Thr Gly Glu Cys Asp Gly Thr Thr Tyr Leu Cys Lys Phe Val Gln
            1045             1050             1055

Leu Thr Asp Asp Pro Ser Leu Asp Ser Glu His Phe Arg Thr Lys Ser
            1060             1065             1070

Gly Val Glu Leu Asn Asn Ala Cys Leu Lys Tyr Lys Cys Val Glu Ser
            1075             1080             1085

Lys Gly Ser Asp Gly Lys Ile Thr His Lys Trp Glu Ile Asp Thr Glu
            1090             1095             1100

Arg Ser Asn Ala Asn Pro Lys Pro Arg Asn Pro Cys Glu Thr Ala Thr
1105             1110             1115             1120

Cys Asn Gln Thr Thr Gly Glu Thr Ile Tyr Thr Lys Lys Thr Cys Thr
            1125             1130             1135

Val Ser Glu Phe Pro Thr Ile Thr Pro Asn Gln Gly Arg Cys Phe Tyr
            1140             1145             1150

Cys Gln Cys Ser Tyr Leu Asp Gly Ser Ser Val Leu Thr Met Tyr Gly
            1155             1160             1165

Glu Thr Asp Lys Glu Tyr Tyr Asp Leu Asp Ala Cys Gly Asn Cys Arg
            1170             1175             1180

Val Trp Asn Gln Thr Asp Arg Thr Gln Gln Leu Asn Asn His Thr Glu
1185             1190             1195             1200

Cys Ile Leu Ala Gly Glu Ile Asn Asn Val Gly Ala Ile Ala Ala Ala
            1205             1210             1215

Thr Thr Val Ala Ala Val Ile Val Ala Val Val Ala Leu Ile Val
            1220             1225             1230

Val Ser Ile Gly Leu Phe Lys Thr Tyr Gln Leu Val Ser Ser Ala Met
            1235             1240             1245

Lys Asn Ala Ile Thr Ile Thr Asn Glu Asn Ala Glu Tyr Val Gly Ala
            1250             1255             1260

Asp Asn Glu Ala Thr Asn Ala Ala Thr Phe Asn Gly
1265             1270             1275

(2) INFORMATION FOR SEQ ID NO:4:

(i) SEQUENCE CHARACTERISTICS:
        (A) LENGTH: 4090 base pairs
        (B) TYPE: nucleic acid
        (C) STRANDEDNESS: single
        (D) TOPOLOGY: linear (ix) FEATURE:
        (A) NAME/KEY: CDS
        (B) LOCATION: 61..3936

(xi) SEQUENCE DESCRIPTION: SEQ ID NO:4:

TTCTGTTAAA TAGGAAAGGC AAGTGATTTA AACAAGACAA TGAACTAGAA AGACAAAGAT    60
```

```
ATG AAA TTA TTA TTA TTA AAT ATC TTA TTA TTA TGT TGT CTT GCA GAT          108
Met Lys Leu Leu Leu Leu Asn Ile Leu Leu Leu Cys Cys Leu Ala Asp
            1300                1305                1310

AAA CTT AAT GAA TTT TCA GCA GAT ATT GAT TAT TAT GAC CTT GGT ATT          156
Lys Leu Asn Glu Phe Ser Ala Asp Ile Asp Tyr Tyr Asp Leu Gly Ile
            1315                1320                1325

ATG TCT CGT GGA AAG AAT GCA GGT TCA TGG TAT CAT TCT TAT GAA CAT          204
Met Ser Arg Gly Lys Asn Ala Gly Ser Trp Tyr His Ser Tyr Glu His
            1330                1335                1340

CAA TAT GAT GTT TTC TAT TAT TTA GCT ATG CAA CCA TGG AGA CAT TTT          252
Gln Tyr Asp Val Phe Tyr Tyr Leu Ala Met Gln Pro Trp Arg His Phe
            1345                1350                1355

GTA TGG ACT ACT TGT ACA ACA ACT GAT GGC AAT AAA GAA TGT TAT AAA          300
Val Trp Thr Thr Cys Thr Thr Thr Asp Gly Asn Lys Glu Cys Tyr Lys
1360                1365                1370                1375

TAT ACT ATC AAT GAA GAT CAT AAT GTA AAG GTT GAA GAT ATT AAT AAA          348
Tyr Thr Ile Asn Glu Asp His Asn Val Lys Val Glu Asp Ile Asn Lys
            1380                1385                1390

ACA GAT ATT AAA CAA GAT TTT TGT CAA AAA GAA TAT GCA TAT CCA ATT          396
Thr Asp Ile Lys Gln Asp Phe Cys Gln Lys Glu Tyr Ala Tyr Pro Ile
            1395                1400                1405

GAA AAA TAT GAA GTT GAT TGG GAC AAT GTT CCA GTT GAT GAA CAA CGA          444
Glu Lys Tyr Glu Val Asp Trp Asp Asn Val Pro Val Asp Glu Gln Arg
            1410                1415                1420

ATT GAA AGT GTA GAT ATT AAT GGA AAA ACT TGT TTT AAA TAT GCA GCT          492
Ile Glu Ser Val Asp Ile Asn Gly Lys Thr Cys Phe Lys Tyr Ala Ala
            1425                1430                1435

AAA AGA CCA TTG GCT TAT GTT TAT TTA AAT ACA AAA ATG ACA TAT GCA          540
Lys Arg Pro Leu Ala Tyr Val Tyr Leu Asn Thr Lys Met Thr Tyr Ala
1440                1445                1450                1455

ACA AAA ACT GAA GCA TAT GAT GTT TGT AGA ATG GAT TTC ATT GGA GGA          588
Thr Lys Thr Glu Ala Tyr Asp Val Cys Arg Met Asp Phe Ile Gly Gly
            1460                1465                1470

AGA TCA ATT ACA TTC AGA TCA TTT AAC ACA GAG AAT AAA GCA TTT ATT          636
Arg Ser Ile Thr Phe Arg Ser Phe Asn Thr Glu Asn Lys Ala Phe Ile
            1475                1480                1485

GAT CAA TAT AAT ACA AAC ACT ACA TCA AAA TGT CTT CTT AAA GTA TAT          684
Asp Gln Tyr Asn Thr Asn Thr Thr Ser Lys Cys Leu Leu Lys Val Tyr
            1490                1495                1500

GAT AAT AAT GTT AAT ACA CAT CTT GCA ATT ATC TTT GGT ATT ACT GAT          732
Asp Asn Asn Val Asn Thr His Leu Ala Ile Ile Phe Gly Ile Thr Asp
1505                1510                1515

TCT ACA GTC ATT AAA TCA CTT CAA GAG AAC TTA TCT CTT TTA AAT AAA          780
Ser Thr Val Ile Lys Ser Leu Gln Glu Asn Leu Ser Leu Leu Asn Lys
1520                1525                1530                1535

TTA ACA ACA GTC AAA GGA GTA ACA CTC TAC TAT CTT AAA GAT GAT ACT          828
Leu Thr Thr Val Lys Gly Val Thr Leu Tyr Tyr Leu Lys Asp Asp Thr
            1540                1545                1550

TAT TTT ACA GTT AAT ATT ACT TTA AAT GAT TTG AAA TAT GAG ACA CTT          876
Tyr Phe Thr Val Asn Ile Thr Leu Asn Asp Leu Lys Tyr Glu Thr Leu
            1555                1560                1565

GTC CAA TAC ACA GCA GGA ACA GGA CAA GTT GAT CCA CTT ATT AAT ATT          924
Val Gln Tyr Thr Ala Gly Thr Gly Gln Val Asp Pro Leu Ile Asn Ile
            1570                1575                1580

GCT AAG AAT GAC TTA ACT GCT AAA GTT GCA GAT AAA AGT AAA GAT AAA          972
Ala Lys Asn Asp Leu Thr Ala Lys Val Ala Asp Lys Ser Lys Asp Lys
            1585                1590                1595

AAT GCA AAT GAT AAA ATC AAA AGA GGA ACT ATG ATT GTG TTA ATG GAT         1020
Asn Ala Asn Asp Lys Ile Lys Arg Gly Thr Met Ile Val Leu Met Asp
1600                1605                1610                1615
```

-continued

```
ACT GCA CTT GGA TCA GAA TTT AAT GCG GAA ACA GAA TTT GAT AGA AAG     1068
Thr Ala Leu Gly Ser Glu Phe Asn Ala Glu Thr Glu Phe Asp Arg Lys
            1620                1625                1630

AAT ATT TCA GTT CAT ACT GTT GTT CTT AAT AGA AAT AAA GAC CCA AAG     1116
Asn Ile Ser Val His Thr Val Val Leu Asn Arg Asn Lys Asp Pro Lys
        1635                1640                1645

ATT ACA CGT AGT GCA TTG AGA CTT GTT TCA CTT GGA CCA CAT TAT CAT     1164
Ile Thr Arg Ser Ala Leu Arg Leu Val Ser Leu Gly Pro His Tyr His
    1650                1655                1660

GAA TTT ACA GGT AAT GAT GAA GTT AAT GCA ACA ATC ACT GCA CTT TTC     1212
Glu Phe Thr Gly Asn Asp Glu Val Asn Ala Thr Ile Thr Ala Leu Phe
1665                1670                1675

AAA GGA ATT AGA GCC AAT TTA ACA GAA AGA TGT GAT AGA GAT AAA TGT     1260
Lys Gly Ile Arg Ala Asn Leu Thr Glu Arg Cys Asp Arg Asp Lys Cys
1680                1685                1690                1695

TCA GGA TTT TGT GAT GCA ATG AAT AGA TGC ACA TGT CCA ATG TGT TGT     1308
Ser Gly Phe Cys Asp Ala Met Asn Arg Cys Thr Cys Pro Met Cys Cys
                1700                1705                1710

GAG AAT GAT TGT TTC TAT ACA TCC TGT GAT GTA GAA ACA GGA TCA TGT     1356
Glu Asn Asp Cys Phe Tyr Thr Ser Cys Asp Val Glu Thr Gly Ser Cys
            1715                1720                1725

ATT CCA TGG CCT AAA GCT AAA CCA AAA GCA AAG AAA GAA TGT CCA GCA     1404
Ile Pro Trp Pro Lys Ala Lys Pro Lys Ala Lys Lys Glu Cys Pro Ala
        1730                1735                1740

ACA TGT GTA GGC TCA TAT GAA TGT AGA GAT CTT GAA GGA TGT GTT GTT     1452
Thr Cys Val Gly Ser Tyr Glu Cys Arg Asp Leu Glu Gly Cys Val Val
    1745                1750                1755

AAA CAA TAT AAT ACA TCT TGT GAA CCA AAA GTG AAA TGC ATG GTA CCA     1500
Lys Gln Tyr Asn Thr Ser Cys Glu Pro Lys Val Lys Cys Met Val Pro
1760                1765                1770                1775

TAT TGT GAT AAT GAT AAG AAT CTA ACT GAA GTA TGT AAA CAA AAA GCT     1548
Tyr Cys Asp Asn Asp Lys Asn Leu Thr Glu Val Cys Lys Gln Lys Ala
                1780                1785                1790

AAT TGT GAA GCA GAT CAA AAA CCA AGT TCT GAT GGA TAT TGT TGG AGT     1596
Asn Cys Glu Ala Asp Gln Lys Pro Ser Ser Asp Gly Tyr Cys Trp Ser
            1795                1800                1805

TAT ACA TGT GAC CAA ACT ACT GGT TTT TGT AAG AAA GAT AAA CGT GGT     1644
Tyr Thr Cys Asp Gln Thr Thr Gly Phe Cys Lys Lys Asp Lys Arg Gly
        1810                1815                1820

GAA AAT ATG TGT ACA GGA AAG ACA AAT AAC TGT CAA GAA TAT GTT TGT     1692
Glu Asn Met Cys Thr Gly Lys Thr Asn Asn Cys Gln Glu Tyr Val Cys
    1825                1830                1835

GAT GAA AAA CAA AGA TGT ACT GTT CAA GAA AAG GTA TGT GTA AAA ACA     1740
Asp Glu Lys Gln Arg Cys Thr Val Gln Glu Lys Val Cys Val Lys Thr
1840                1845                1850                1855

TCA CCT TAT ATT GAA ATG TCA TGT TAT GTA GCC AAG TGT AAT CTC AAT     1788
Ser Pro Tyr Ile Glu Met Ser Cys Tyr Val Ala Lys Cys Asn Leu Asn
                1860                1865                1870

ACA GGT ATG TGT GAG AAC AGA TTA TCA TGT GAT ACA TAC TCA TCA TGT     1836
Thr Gly Met Cys Glu Asn Arg Leu Ser Cys Asp Thr Tyr Ser Ser Cys
            1875                1880                1885

GGT GGA GAT TCT ACA GGA TCA GTA TGT AAA TGT GAT TCT ACA ACT AAT     1884
Gly Gly Asp Ser Thr Gly Ser Val Cys Lys Cys Asp Ser Thr Thr Asn
        1890                1895                1900

AAC CAA TGT CAA TGT ACT CAA GTA AAA AAC GGT AAT TAT TGT GAT TCT     1932
Asn Gln Cys Gln Cys Thr Gln Val Lys Asn Gly Asn Tyr Cys Asp Ser
    1905                1910                1915

AAT AAA CAT CAA ATT TGT GAT TAT ACA GGA AAA ACA CCA CAA TGT AAA     1980
Asn Lys His Gln Ile Cys Asp Tyr Thr Gly Lys Thr Pro Gln Cys Lys
```

```
1920                1925                1930                1935

GTG TCT AAT TGT ACA GAA GAT CTT GTT AGA GAT GGA TGT CTT ATT AAG        2028
Val Ser Asn Cys Thr Glu Asp Leu Val Arg Asp Gly Cys Leu Ile Lys
            1940                1945                1950

AGA TGT AAT GAA ACA AGT AAA ACA ACA TAT TGG GAG AAT GTT GAT TGT        2076
Arg Cys Asn Glu Thr Ser Lys Thr Thr Tyr Trp Glu Asn Val Asp Cys
            1955                1960                1965

TCT AAA ACT GAA GTT AAA TTC GCT CAA GAT GGT AAA TCT GAA AAT ATG        2124
Ser Lys Thr Glu Val Lys Phe Ala Gln Asp Gly Lys Ser Glu Asn Met
            1970                1975                1980

TGT AAA CAA TAT TAT TCA ACT ACA TGT TTG AAT GGA CAA TGT GTT GTT        2172
Cys Lys Gln Tyr Tyr Ser Thr Thr Cys Leu Asn Gly Gln Cys Val Val
            1985                1990                1995

CAA GCA GTT GGT GAT GTT TCT AAT GTA GGA TGT GGA TAT TGT TCA ATG        2220
Gln Ala Val Gly Asp Val Ser Asn Val Gly Cys Gly Tyr Cys Ser Met
2000                2005                2010                2015

GGA ACA GAT AAT ATT ATT ACA TAT CAT GAT GAT TGT AAT TCA CGT AAA        2268
Gly Thr Asp Asn Ile Ile Thr Tyr His Asp Asp Cys Asn Ser Arg Lys
            2020                2025                2030

TCA CAA TGT GGA AAC TTT AAT GGT AAG TGT GTA GAA AAT AGT GAC AAA        2316
Ser Gln Cys Gly Asn Phe Asn Gly Lys Cys Val Glu Asn Ser Asp Lys
            2035                2040                2045

TCA TAT TCT TGT GTA TTT AAT AAG GAT GTT TCT TCT ACA TCA GAT AAT        2364
Ser Tyr Ser Cys Val Phe Asn Lys Asp Val Ser Ser Thr Ser Asp Asn
            2050                2055                2060

GAT ATT TGT GCA AAA TGT TCT AGT TTA ACA TGT CCA GCT GAT ACT ACA        2412
Asp Ile Cys Ala Lys Cys Ser Ser Leu Thr Cys Pro Ala Asp Thr Thr
            2065                2070                2075

TAC AGA ACA TAT ACA TAT GAC TCA AAA ACA GGA ACA TGT AAA GCA ACT        2460
Tyr Arg Thr Tyr Thr Tyr Asp Ser Lys Thr Gly Thr Cys Lys Ala Thr
2080                2085                2090                2095

GTT CAA CCA ACA CCA GCA TGT TCA GTA TGT GAA AGT GGT AAA TTT GTA        2508
Val Gln Pro Thr Pro Ala Cys Ser Val Cys Glu Ser Gly Lys Phe Val
                2100                2105                2110

GAA AAA TGC AAA GAT CAA AAA TTA GAA CGT AAA GTT ACT TTA GAA AAT        2556
Glu Lys Cys Lys Asp Gln Lys Leu Glu Arg Lys Val Thr Leu Glu Asn
            2115                2120                2125

GGA AAA GAA TAT AAA TAC ACC ATT CCA AAA GAT TGT GTC AAT GAA CAA        2604
Gly Lys Glu Tyr Lys Tyr Thr Ile Pro Lys Asp Cys Val Asn Glu Gln
            2130                2135                2140

TGC ATT CCA AGA ACA TAC ATA GAT TGT TTA GGT AAT GAT GAT AAC TTT        2652
Cys Ile Pro Arg Thr Tyr Ile Asp Cys Leu Gly Asn Asp Asp Asn Phe
            2145                2150                2155

AAA TCT ATT TAT AAC TTC TAT TTA CCA TGT CAA GCA TAT GTT ACA GCT        2700
Lys Ser Ile Tyr Asn Phe Tyr Leu Pro Cys Gln Ala Tyr Val Thr Ala
2160                2165                2170                2175

ACC TAT CAT TAC AGT TCA TTA TTC AAT TTA ACT AGT TAT AAA CTT CAT        2748
Thr Tyr His Tyr Ser Ser Leu Phe Asn Leu Thr Ser Tyr Lys Leu His
            2180                2185                2190

TTA CCA CAA AGT GAA GAA TTT ATG AAA GAG GCA GAC AAA GAA GCA TAT        2796
Leu Pro Gln Ser Glu Glu Phe Met Lys Glu Ala Asp Lys Glu Ala Tyr
            2195                2200                2205

TGT ACA TAC GAA ATA ACA ACA AGA GAA TGT AAA ACA TGT TCA TTA ATT        2844
Cys Thr Tyr Glu Ile Thr Thr Arg Glu Cys Lys Thr Cys Ser Leu Ile
            2210                2215                2220

GAA ACT AGA GAA AAA GTC CAA GAA GTT GAT TTG TGT GCA GAA GAG ACT        2892
Glu Thr Arg Glu Lys Val Gln Glu Val Asp Leu Cys Ala Glu Glu Thr
            2225                2230                2235

AAG AAT GGA GGA GTT CCA TTC AAA TGT AAG AAT AAC AAT TGC ATT ATT        2940
Lys Asn Gly Gly Val Pro Phe Lys Cys Lys Asn Asn Asn Cys Ile Ile
```

```
Lys Asn Gly Gly Val Pro Phe Lys Cys Lys Asn Asn Cys Ile Ile
2240                2245                2250                2255

GAT CCT AAC TTT GAT TGT CAA CCT ATT GAA TGT AAG ATT CAA GAG ATT    2988
Asp Pro Asn Phe Asp Cys Gln Pro Ile Glu Cys Lys Ile Gln Glu Ile
                2260                2265                2270

GTT ATT ACA GAA AAA GAT GGA ATA AAA ACA ACA ACA TGT AAA AAT ACC    3036
Val Ile Thr Glu Lys Asp Gly Ile Lys Thr Thr Thr Cys Lys Asn Thr
            2275                2280                2285

ACA AAA ACA ACA TGT GAC ACT AAC AAT AAG AGA ATA GAA GAT GCA CGT    3084
Thr Lys Thr Thr Cys Asp Thr Asn Asn Lys Arg Ile Glu Asp Ala Arg
        2290                2295                2300

AAA GCA TTC ATT GAA GGA AAA GAA GGA ATT GAG CAA GTA GAA TGT GCA    3132
Lys Ala Phe Ile Glu Gly Lys Glu Gly Ile Glu Gln Val Glu Cys Ala
    2305                2310                2315

AGT ACT GTT TGT CAA AAT GAT AAT AGT TGT CCA ATT ATT ACT GAT GTA    3180
Ser Thr Val Cys Gln Asn Asp Asn Ser Cys Pro Ile Ile Thr Asp Val
2320                2325                2330                2335

GAA AAA TGT AAT CAA AAC ACA GAA GTA GAT TAT GGA TGT AAA GCA ATG    3228
Glu Lys Cys Asn Gln Asn Thr Glu Val Asp Tyr Gly Cys Lys Ala Met
                2340                2345                2350

ACA GGA GAA TGT GAT GGT ACT ACA TAT CTT TGT AAA TTT GTA CAA CTT    3276
Thr Gly Glu Cys Asp Gly Thr Thr Tyr Leu Cys Lys Phe Val Gln Leu
            2355                2360                2365

ACT GAT GAT CCA TCA TTA GAT AGT GAA CAT TTT AGA ACT AAA TCA GGA    3324
Thr Asp Asp Pro Ser Leu Asp Ser Glu His Phe Arg Thr Lys Ser Gly
        2370                2375                2380

GTT GAA CTT AAC AAT GCA TGT TTG AAA TAT AAA TGT GTT GAG AGT AAA    3372
Val Glu Leu Asn Asn Ala Cys Leu Lys Tyr Lys Cys Val Glu Ser Lys
    2385                2390                2395

GGA AGT GAT GGA AAA ATC ACA CAT AAA TGG GAA ATT GAT ACA GAA CGA    3420
Gly Ser Asp Gly Lys Ile Thr His Lys Trp Glu Ile Asp Thr Glu Arg
2400                2405                2410                2415

TCA AAT GCT AAT CCA AAA CCA AGA AAT CCA TGC GAA ACC GCA ACA TGT    3468
Ser Asn Ala Asn Pro Lys Pro Arg Asn Pro Cys Glu Thr Ala Thr Cys
                2420                2425                2430

AAT CAA ACA ACT GGA GAA ACT ATT TAC ACA AAG AAA ACA TGT ACT GTT    3516
Asn Gln Thr Thr Gly Glu Thr Ile Tyr Thr Lys Lys Thr Cys Thr Val
            2435                2440                2445

TCA GAA GAA TTC CCA ACA ATC ACA CCA AAT CAA GGA AGA TGT TTC TAT    3564
Ser Glu Glu Phe Pro Thr Ile Thr Pro Asn Gln Gly Arg Cys Phe Tyr
        2450                2455                2460

TGT CAA TGT TCA TAT CTT GAC GGT TCA TCA GTT CTT ACT ATG TAT GGA    3612
Cys Gln Cys Ser Tyr Leu Asp Gly Ser Ser Val Leu Thr Met Tyr Gly
    2465                2470                2475

GAA ACA GAT AAA GAA TAT TAT GAT CTT GAT GCA TGT GGT AAT TGT CGT    3660
Glu Thr Asp Lys Glu Tyr Tyr Asp Leu Asp Ala Cys Gly Asn Cys Arg
2480                2485                2490                2495

GTT TGG AAT CAG ACA GAT AGA ACA CAA CAA CTT AAT AAT CAC ACC GAG    3708
Val Trp Asn Gln Thr Asp Arg Thr Gln Gln Leu Asn Asn His Thr Glu
                2500                2505                2510

TGT ATT CTC GCA GGA GAA ATT AAT AAT GTT GGA GCT ATT GCA GCG GCA    3756
Cys Ile Leu Ala Gly Glu Ile Asn Asn Val Gly Ala Ile Ala Ala Ala
            2515                2520                2525

ACT ACT GTG GCT GTA GTT GTA GTT GCA GTC GTA GTT GCA TTA ATT GTT    3804
Thr Thr Val Ala Val Val Val Val Ala Val Val Ala Leu Ile Val
        2530                2535                2540

GTT TCT ATT GGA TTA TTT AAG ACT TAT CAA CTT GTT TCA TCA GCT ATG    3852
Val Ser Ile Gly Leu Phe Lys Thr Tyr Gln Leu Val Ser Ser Ala Met
    2545                2550                2555
```

-continued

```
AAG AAT GCC ATT ACA ATA ACT AAT GAA AAT GCA GAA TAT GTT GGA GCA    3900
Lys Asn Ala Ile Thr Ile Thr Asn Glu Asn Ala Glu Tyr Val Gly Ala
2560                2565                2570                2575

GAT AAT GAA GCA ACT AAT GCA GCA ACA TTC AAT GGA TAAGAACAAT         3946
Asp Asn Glu Ala Thr Asn Ala Ala Thr Phe Asn Gly
            2580                2585

AATTAAGAGA ATTGAATAAC ATTTTATGTT TTTAGATTAA AAATAAAAAG AAGAATAAAT  4006

TGAGTGATAA ACAATGAATA AAATAAATAA AAATAAACAA GAATAAAGTG AACATCATTT  4066

TTATTTTCAT ATTTTAACAA CACT                                        4090
```

(2) INFORMATION FOR SEQ ID NO:5:

(i) SEQUENCE CHARACTERISTICS:
        (A) LENGTH: 1292 amino acids
        (B) TYPE: amino acid
        (D) TOPOLOGY: linear (ii) MOLECULE TYPE: protein (xi) SEQUENCE DESCRIPTION: SEQ ID NO:5:

```
Met Lys Leu Leu Leu Asn Ile Leu Leu Cys Cys Leu Ala Asp
 1               5                  10                  15

Lys Leu Asn Glu Phe Ser Ala Asp Ile Asp Tyr Tyr Asp Leu Gly Ile
            20                  25                  30

Met Ser Arg Gly Lys Asn Ala Gly Ser Trp Tyr His Ser Tyr Glu His
        35                  40                  45

Gln Tyr Asp Val Phe Tyr Tyr Leu Ala Met Gln Pro Trp Arg His Phe
    50                  55                  60

Val Trp Thr Thr Cys Thr Thr Thr Asp Gly Asn Lys Glu Cys Tyr Lys
65                  70                  75                  80

Tyr Thr Ile Asn Glu Asp His Asn Val Lys Val Glu Asp Ile Asn Lys
                85                  90                  95

Thr Asp Ile Lys Gln Asp Phe Cys Gln Lys Glu Tyr Ala Tyr Pro Ile
            100                 105                 110

Glu Lys Tyr Glu Val Asp Trp Asp Asn Val Pro Val Asp Glu Gln Arg
        115                 120                 125

Ile Glu Ser Val Asp Ile Asn Gly Lys Thr Cys Phe Lys Tyr Ala Ala
    130                 135                 140

Lys Arg Pro Leu Ala Tyr Val Tyr Leu Asn Thr Lys Met Thr Tyr Ala
145                 150                 155                 160

Thr Lys Thr Glu Ala Tyr Asp Val Cys Arg Met Asp Phe Ile Gly Gly
                165                 170                 175

Arg Ser Ile Thr Phe Arg Ser Phe Asn Thr Glu Asn Lys Ala Phe Ile
            180                 185                 190

Asp Gln Tyr Asn Thr Asn Thr Thr Ser Lys Cys Leu Leu Lys Val Tyr
        195                 200                 205

Asp Asn Asn Val Asn Thr His Leu Ala Ile Ile Phe Gly Ile Thr Asp
    210                 215                 220

Ser Thr Val Ile Lys Ser Leu Gln Glu Asn Leu Ser Leu Leu Asn Lys
225                 230                 235                 240

Leu Thr Thr Val Lys Gly Val Thr Leu Tyr Tyr Leu Lys Asp Asp Thr
                245                 250                 255

Tyr Phe Thr Val Asn Ile Thr Leu Asn Asp Leu Lys Tyr Glu Thr Leu
            260                 265                 270

Val Gln Tyr Thr Ala Gly Thr Gly Gln Val Asp Pro Leu Ile Asn Ile
        275                 280                 285
```

```
Ala Lys Asn Asp Leu Thr Ala Lys Val Ala Asp Lys Ser Lys Asp Lys
    290                 295                 300
Asn Ala Asn Asp Lys Ile Lys Arg Gly Thr Met Ile Val Leu Met Asp
305                 310                 315                 320
Thr Ala Leu Gly Ser Glu Phe Asn Ala Glu Thr Glu Phe Asp Arg Lys
                325                 330                 335
Asn Ile Ser Val His Thr Val Leu Asn Arg Asn Lys Asp Pro Lys
                340                 345                 350
Ile Thr Arg Ser Ala Leu Arg Leu Val Ser Leu Gly Pro His Tyr His
            355                 360                 365
Glu Phe Thr Gly Asn Asp Glu Val Asn Ala Thr Ile Thr Ala Leu Phe
    370                 375                 380
Lys Gly Ile Arg Ala Asn Leu Thr Glu Arg Cys Asp Arg Asp Lys Cys
385                 390                 395                 400
Ser Gly Phe Cys Asp Ala Met Asn Arg Cys Thr Cys Pro Met Cys Cys
                405                 410                 415
Glu Asn Asp Cys Phe Tyr Thr Ser Cys Asp Val Glu Thr Gly Ser Cys
                420                 425                 430
Ile Pro Trp Pro Lys Ala Lys Pro Lys Ala Lys Lys Glu Cys Pro Ala
            435                 440                 445
Thr Cys Val Gly Ser Tyr Glu Cys Arg Asp Leu Glu Gly Cys Val Val
    450                 455                 460
Lys Gln Tyr Asn Thr Ser Cys Glu Pro Lys Val Lys Cys Met Val Pro
465                 470                 475                 480
Tyr Cys Asp Asn Asp Lys Asn Leu Thr Glu Val Cys Lys Gln Lys Ala
                485                 490                 495
Asn Cys Glu Ala Asp Gln Lys Pro Ser Ser Asp Gly Tyr Cys Trp Ser
                500                 505                 510
Tyr Thr Cys Asp Gln Thr Thr Gly Phe Cys Lys Lys Asp Lys Arg Gly
            515                 520                 525
Glu Asn Met Cys Thr Gly Lys Thr Asn Asn Cys Gln Glu Tyr Val Cys
    530                 535                 540
Asp Glu Lys Gln Arg Cys Thr Val Gln Glu Lys Val Cys Val Lys Thr
545                 550                 555                 560
Ser Pro Tyr Ile Glu Met Ser Cys Tyr Val Ala Lys Cys Asn Leu Asn
                565                 570                 575
Thr Gly Met Cys Glu Asn Arg Leu Ser Cys Asp Thr Tyr Ser Ser Cys
                580                 585                 590
Gly Gly Asp Ser Thr Gly Ser Val Cys Lys Cys Asp Ser Thr Thr Asn
            595                 600                 605
Asn Gln Cys Gln Cys Thr Gln Val Lys Asn Gly Asn Tyr Cys Asp Ser
    610                 615                 620
Asn Lys His Gln Ile Cys Asp Tyr Thr Gly Lys Thr Pro Gln Cys Lys
625                 630                 635                 640
Val Ser Asn Cys Thr Glu Asp Leu Val Arg Asp Gly Cys Leu Ile Lys
                645                 650                 655
Arg Cys Asn Glu Thr Ser Lys Thr Thr Tyr Trp Glu Asn Val Asp Cys
                660                 665                 670
Ser Lys Thr Glu Val Lys Phe Ala Gln Asp Gly Lys Ser Glu Asn Met
            675                 680                 685
Cys Lys Gln Tyr Tyr Ser Thr Ser Thr Cys Leu Asn Gly Gln Cys Val Val
    690                 695                 700
```

-continued

```
Gln Ala Val Gly Asp Val Ser Asn Val Gly Cys Gly Tyr Cys Ser Met
705                 710                 715                 720
Gly Thr Asp Asn Ile Ile Thr Tyr His Asp Asp Cys Asn Ser Arg Lys
                725                 730                 735
Ser Gln Cys Gly Asn Phe Asn Gly Lys Cys Val Glu Asn Ser Asp Lys
            740                 745                 750
Ser Tyr Ser Cys Val Phe Asn Lys Asp Val Ser Thr Ser Asp Asn
        755                 760                 765
Asp Ile Cys Ala Lys Cys Ser Ser Leu Thr Cys Pro Ala Asp Thr Thr
770                 775                 780
Tyr Arg Thr Tyr Thr Tyr Asp Ser Lys Thr Gly Thr Cys Lys Ala Thr
785                 790                 795                 800
Val Gln Pro Thr Pro Ala Cys Ser Val Cys Glu Ser Gly Lys Phe Val
                805                 810                 815
Glu Lys Cys Lys Asp Gln Lys Leu Glu Arg Lys Val Thr Leu Glu Asn
            820                 825                 830
Gly Lys Glu Tyr Lys Tyr Thr Ile Pro Lys Asp Cys Val Asn Glu Gln
        835                 840                 845
Cys Ile Pro Arg Thr Tyr Ile Asp Cys Leu Gly Asn Asp Asp Asn Phe
850                 855                 860
Lys Ser Ile Tyr Asn Phe Tyr Leu Pro Cys Gln Ala Tyr Val Thr Ala
865                 870                 875                 880
Thr Tyr His Tyr Ser Ser Leu Phe Asn Leu Thr Ser Tyr Lys Leu His
                885                 890                 895
Leu Pro Gln Ser Glu Glu Phe Met Lys Glu Ala Asp Lys Glu Ala Tyr
            900                 905                 910
Cys Thr Tyr Glu Ile Thr Thr Arg Glu Cys Lys Thr Cys Ser Leu Ile
        915                 920                 925
Glu Thr Arg Glu Lys Val Gln Glu Val Asp Leu Cys Ala Glu Thr
930                 935                 940
Lys Asn Gly Gly Val Pro Phe Lys Cys Lys Asn Asn Asn Cys Ile Ile
945                 950                 955                 960
Asp Pro Asn Phe Asp Cys Gln Pro Ile Glu Cys Lys Ile Gln Glu Ile
                965                 970                 975
Val Ile Thr Glu Lys Asp Gly Ile Lys Thr Thr Thr Cys Lys Asn Thr
            980                 985                 990
Thr Lys Thr Thr Cys Asp Thr Asn Asn Lys Arg Ile Glu Asp Ala Arg
        995                 1000                1005
Lys Ala Phe Ile Glu Gly Lys Glu Gly Ile Glu Gln Val Glu Cys Ala
    1010                1015                1020
Ser Thr Val Cys Gln Asn Asp Asn Ser Cys Pro Ile Ile Thr Asp Val
1025                1030                1035                1040
Glu Lys Cys Asn Gln Asn Thr Glu Val Asp Tyr Gly Cys Lys Ala Met
                1045                1050                1055
Thr Gly Glu Cys Asp Gly Thr Thr Tyr Leu Cys Lys Phe Val Gln Leu
            1060                1065                1070
Thr Asp Asp Pro Ser Leu Asp Ser Glu His Phe Arg Thr Lys Ser Gly
        1075                1080                1085
Val Glu Leu Asn Asn Ala Cys Leu Lys Tyr Lys Cys Val Glu Ser Lys
    1090                1095                1100
Gly Ser Asp Gly Lys Ile Thr His Lys Trp Glu Ile Asp Thr Glu Arg
1105                1110                1115                1120
Ser Asn Ala Asn Pro Lys Pro Arg Asn Pro Cys Glu Thr Ala Thr Cys
```

```
                       1125                1130               1135
Asn Gln Thr Thr Gly Glu Thr Ile Tyr Thr Lys Lys Thr Cys Thr Val
                1140               1145                1150

Ser Glu Glu Phe Pro Thr Ile Thr Pro Asn Gln Gly Arg Cys Phe Tyr
        1155                1160                1165

Cys Gln Cys Ser Tyr Leu Asp Gly Ser Ser Val Leu Thr Met Tyr Gly
        1170                1175                1180

Glu Thr Asp Lys Glu Tyr Tyr Asp Leu Asp Ala Cys Gly Asn Cys Arg
1185                1190                1195                1200

Val Trp Asn Gln Thr Asp Arg Thr Gln Gln Leu Asn Asn His Thr Glu
                1205                1210                1215

Cys Ile Leu Ala Gly Glu Ile Asn Asn Val Gly Ala Ile Ala Ala Ala
                1220                1225                1230

Thr Thr Val Ala Val Val Val Ala Val Val Ala Leu Ile Val
                1235                1240                1245

Val Ser Ile Gly Leu Phe Lys Thr Tyr Gln Leu Val Ser Ser Ala Met
        1250                1255                1260

Lys Asn Ala Ile Thr Ile Thr Asn Glu Asn Ala Glu Tyr Val Gly Ala
1265                1270                1275                1280

Asp Asn Glu Ala Thr Asn Ala Ala Thr Phe Asn Gly
                1285                1290

(2) INFORMATION FOR SEQ ID NO:6:

(i) SEQUENCE CHARACTERISTICS:
        (A) LENGTH: 1277 amino acids
        (B) TYPE: amino acid
        (C) STRANDEDNESS: single
        (D) TOPOLOGY: linear (xi) SEQUENCE DESCRIPTION: SEQ ID NO:6:

Asp Lys Leu Asn Glu Phe Ser Ala Asp Ile Asp Tyr Tyr Asp Leu Gly
1               5                   10                  15

Ile Met Ser Arg Gly Lys Asn Ala Gly Ser Trp Tyr His Ser Tyr Glu
                20                  25                  30

His Gln Tyr Asp Val Phe Tyr Tyr Leu Ala Met Gln Pro Trp Arg His
            35                  40                  45

Phe Val Trp Thr Thr Cys Thr Thr Asp Gly Asn Lys Glu Cys Tyr
    50                  55                  60

Lys Tyr Thr Ile Asn Glu Asp His Asn Val Lys Val Glu Asp Ile Asn
65                  70                  75                  80

Lys Thr Asp Ile Lys Gln Asp Phe Cys Gln Lys Glu Tyr Ala Tyr Pro
                85                  90                  95

Ile Glu Lys Tyr Glu Val Asp Trp Asp Asn Val Pro Val Asp Glu Gln
                100                 105                 110

Arg Ile Glu Ser Val Asp Ile Asn Gly Lys Thr Cys Phe Lys Tyr Ala
            115                 120                 125

Ala Lys Arg Pro Leu Ala Tyr Val Tyr Leu Asn Thr Lys Met Thr Tyr
130                 135                 140

Ala Thr Lys Thr Glu Ala Tyr Asp Val Cys Arg Met Asp Phe Ile Gly
145                 150                 155                 160

Gly Arg Ser Ile Thr Phe Arg Ser Phe Asn Thr Glu Asn Lys Ala Phe
                165                 170                 175

Ile Asp Gln Tyr Asn Thr Asn Thr Thr Ser Lys Cys Leu Leu Lys Val
                180                 185                 190
```

-continued

```
Tyr Asp Asn Asn Val Asn Thr His Leu Ala Ile Ile Phe Gly Ile Thr
            195                 200                 205
Asp Ser Thr Val Ile Lys Ser Leu Gln Glu Asn Leu Ser Leu Leu Asn
        210                 215                 220
Lys Leu Thr Thr Val Lys Gly Val Thr Leu Tyr Tyr Leu Lys Asp Asp
225                 230                 235                 240
Thr Tyr Phe Thr Val Asn Ile Thr Leu Asn Asp Leu Lys Tyr Glu Thr
                245                 250                 255
Leu Val Gln Tyr Thr Ala Gly Thr Gly Gln Val Asp Pro Leu Ile Asn
            260                 265                 270
Ile Ala Lys Asn Asp Leu Thr Ala Lys Val Ala Asp Lys Ser Lys Asp
        275                 280                 285
Lys Asn Ala Asn Asp Lys Ile Lys Arg Gly Thr Met Ile Val Leu Met
        290                 295                 300
Asp Thr Ala Leu Gly Ser Glu Phe Asn Ala Glu Thr Glu Phe Asp Arg
305                 310                 315                 320
Lys Asn Ile Ser Val His Thr Val Leu Asn Arg Asn Lys Asp Pro
                325                 330                 335
Lys Ile Thr Arg Ser Ala Leu Arg Leu Val Ser Leu Gly Pro His Tyr
            340                 345                 350
His Glu Phe Thr Gly Asn Asp Glu Val Asn Ala Thr Ile Thr Ala Leu
            355                 360                 365
Phe Lys Gly Ile Arg Ala Asn Leu Thr Glu Arg Cys Asp Arg Asp Lys
        370                 375                 380
Cys Ser Gly Phe Cys Asp Ala Met Asn Arg Cys Thr Cys Pro Met Cys
385                 390                 395                 400
Cys Glu Asn Asp Cys Phe Tyr Thr Ser Cys Asp Val Glu Thr Gly Ser
                405                 410                 415
Cys Ile Pro Trp Pro Lys Ala Lys Pro Lys Ala Lys Lys Glu Cys Pro
            420                 425                 430
Ala Thr Cys Val Gly Ser Tyr Glu Cys Arg Asp Leu Glu Gly Cys Val
        435                 440                 445
Val Lys Gln Tyr Asn Thr Ser Cys Glu Pro Lys Val Lys Cys Met Val
    450                 455                 460
Pro Tyr Cys Asp Asn Asp Lys Asn Leu Thr Glu Val Cys Lys Gln Lys
465                 470                 475                 480
Ala Asn Cys Glu Ala Asp Gln Lys Pro Ser Ser Asp Gly Tyr Cys Trp
                485                 490                 495
Ser Tyr Thr Cys Asp Gln Thr Thr Gly Phe Cys Lys Lys Asp Lys Arg
            500                 505                 510
Gly Glu Asn Met Cys Thr Gly Lys Thr Asn Asn Cys Gln Glu Tyr Val
            515                 520                 525
Cys Asp Glu Lys Gln Arg Cys Thr Val Gln Glu Lys Val Cys Val Lys
        530                 535                 540
Thr Ser Pro Tyr Ile Glu Met Ser Cys Tyr Val Ala Lys Cys Asn Leu
545                 550                 555                 560
Asn Thr Gly Met Cys Glu Asn Arg Leu Ser Cys Asp Thr Tyr Ser Ser
                565                 570                 575
Cys Gly Gly Asp Ser Thr Gly Ser Val Cys Lys Cys Asp Ser Thr Thr
            580                 585                 590
Asn Asn Gln Cys Gln Cys Thr Gln Val Lys Asn Gly Asn Tyr Cys Asp
        595                 600                 605
Ser Asn Lys His Gln Ile Cys Asp Tyr Thr Gly Lys Thr Pro Gln Cys
```

-continued

```
          610                 615                 620
Lys Val Ser Asn Cys Thr Glu Asp Leu Val Arg Asp Gly Cys Leu Ile
625                 630                 635                 640
Lys Arg Cys Asn Glu Thr Ser Lys Thr Thr Tyr Trp Glu Asn Val Asp
                645                 650                 655
Cys Ser Lys Thr Glu Val Lys Phe Ala Gln Asp Gly Lys Ser Glu Asn
                660                 665                 670
Met Cys Lys Gln Tyr Tyr Ser Thr Thr Cys Leu Asn Gly Gln Cys Val
            675                 680                 685
Val Gln Ala Val Gly Asp Val Ser Asn Val Gly Cys Gly Tyr Cys Ser
            690                 695                 700
Met Gly Thr Asp Asn Ile Ile Thr Tyr His Asp Asp Cys Asn Ser Arg
705                 710                 715                 720
Lys Ser Gln Cys Gly Asn Phe Asn Gly Lys Cys Val Glu Asn Ser Asp
                725                 730                 735
Lys Ser Tyr Ser Cys Val Phe Asn Lys Asp Val Ser Ser Thr Ser Asp
                740                 745                 750
Asn Asp Ile Cys Ala Lys Cys Ser Ser Leu Thr Cys Pro Ala Asp Thr
                755                 760                 765
Thr Tyr Arg Thr Tyr Thr Tyr Asp Ser Lys Thr Gly Thr Cys Lys Ala
770                 775                 780
Thr Val Gln Pro Thr Pro Ala Cys Ser Val Cys Glu Ser Gly Lys Phe
785                 790                 795                 800
Val Glu Lys Cys Lys Asp Gln Lys Leu Glu Arg Lys Val Thr Leu Glu
                805                 810                 815
Asn Gly Lys Glu Tyr Lys Tyr Thr Ile Pro Lys Asp Cys Val Asn Glu
                820                 825                 830
Gln Cys Ile Pro Arg Thr Tyr Ile Asp Cys Leu Gly Asn Asp Asp Asn
            835                 840                 845
Phe Lys Ser Ile Tyr Asn Phe Tyr Leu Pro Cys Gln Ala Tyr Val Thr
            850                 855                 860
Ala Thr Tyr His Tyr Ser Ser Leu Phe Asn Leu Thr Ser Tyr Lys Leu
865                 870                 875                 880
His Leu Pro Gln Ser Glu Glu Phe Met Lys Glu Ala Asp Lys Glu Ala
                885                 890                 895
Tyr Cys Thr Tyr Glu Ile Thr Thr Arg Glu Cys Lys Thr Cys Ser Leu
            900                 905                 910
Ile Glu Thr Arg Glu Lys Val Gln Glu Val Asp Leu Cys Ala Glu Glu
            915                 920                 925
Thr Lys Asn Gly Gly Val Pro Phe Lys Cys Lys Asn Asn Cys Ile
930                 935                 940
Ile Asp Pro Asn Phe Asp Cys Gln Pro Ile Glu Cys Lys Ile Gln Glu
945                 950                 955                 960
Ile Val Ile Thr Glu Lys Asp Gly Ile Lys Thr Thr Cys Lys Asn
                965                 970                 975
Thr Thr Lys Thr Thr Cys Asp Thr Asn Asn Lys Arg Ile Glu Asp Ala
            980                 985                 990
Arg Lys Ala Phe Ile Glu Gly Lys Glu Gly Ile Glu Gln Val Glu Cys
            995                1000                1005
Ala Ser Thr Val Cys Gln Asn Asp Asn Ser Cys Pro Ile Ile Thr Asp
        1010                1015                1020
Val Glu Lys Cys Asn Gln Asn Thr Glu Val Asp Tyr Gly Cys Lys Ala
1025                1030                1035                1040
```

Met Thr Gly Glu Cys Asp Gly Thr Thr Tyr Leu Cys Lys Phe Val Gln
            1045                1050                1055

Leu Thr Asp Asp Pro Ser Leu Asp Ser Glu His Phe Arg Thr Lys Ser
        1060                1065                1070

Gly Val Glu Leu Asn Asn Ala Cys Leu Lys Tyr Lys Cys Val Glu Ser
        1075                1080                1085

Lys Gly Ser Asp Gly Lys Ile Thr His Lys Trp Glu Ile Asp Thr Glu
        1090                1095                1100

Arg Ser Asn Ala Asn Pro Lys Pro Arg Asn Pro Cys Glu Thr Ala Thr
1105                1110                1115                1120

Cys Asn Gln Thr Thr Gly Glu Thr Ile Tyr Thr Lys Lys Thr Cys Thr
            1125                1130                1135

Val Ser Glu Glu Phe Pro Thr Ile Thr Pro Asn Gln Gly Arg Cys Phe
            1140                1145                1150

Tyr Cys Gln Cys Ser Tyr Leu Asp Gly Ser Ser Val Leu Thr Met Tyr
            1155                1160                1165

Gly Glu Thr Asp Lys Glu Tyr Tyr Asp Leu Asp Ala Cys Gly Asn Cys
        1170                1175                1180

Arg Val Trp Asn Gln Thr Asp Arg Thr Gln Gln Leu Asn Asn His Thr
1185                1190                1195                1200

Glu Cys Ile Leu Ala Gly Glu Ile Asn Asn Val Gly Ala Ile Ala Ala
            1205                1210                1215

Ala Thr Thr Val Ala Val Val Val Val Ala Val Val Ala Leu Ile
            1220                1225                1230

Val Val Ser Ile Gly Leu Phe Lys Thr Tyr Gln Leu Val Ser Ser Ala
            1235                1240                1245

Met Lys Asn Ala Ile Thr Ile Thr Asn Glu Asn Ala Glu Tyr Val Gly
        1250                1255                1260

Ala Asp Asn Glu Ala Thr Asn Ala Ala Thr Phe Asn Gly
1265                1270                1275                1280

(2) INFORMATION FOR SEQ ID NO:7:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO:7:

TTTGTCACTA TTTTCTAC                                                     18

(2) INFORMATION FOR SEQ ID NO:8:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:8:

TATCTCCATT TGGTTGA                                                      17

(2) INFORMATION FOR SEQ ID NO:9:

(i) SEQUENCE CHARACTERISTICS:
        (A) LENGTH: 18 base pairs
        (B) TYPE: nucleic acid
        (C) STRANDEDNESS: single -continued

```
        (D) TOPOLOGY: linear (xi) SEQUENCE DESCRIPTION: SEQ ID NO:9:

TTTGTCACTA TTTTCTAC                                             18

(2) INFORMATION FOR SEQ ID NO:10:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO:10:

CCCAAGCATA TTTGAATG                                             18

(2) INFORMATION FOR SEQ ID NO:11:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (xi) SEQUENCE DESCRIPTION: SEQ ID NO:11:

GGCGGCTGCA GAACGCAATT AATGTGAGT                                 29

(2) INFORMATION FOR SEQ ID NO:12:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (xi) SEQUENCE DESCRIPTION: SEQ ID NO:12:

GGCGGCTGCA GCTTACAGAC AAGCTGTGA                                 29
```

RECOMBINANT *ENTAMOEBA HISTOLYTICA* LECTIN SUBUNIT PEPTIDES AND REAGENTS SPECIFIC FOR MEMBERS OF THE 170 KDA SUBUNIT MULTIGENE FAMILY

CROSS-REFERENCE TO RELATED APPLICATIONS

This application is a continuation-in-part of U.S. Ser. No. 08/569,214, filed Apr. 29, 1996 which was a National Stage filing of PCT/US94/06890, filed Jun. 17, 1994, which is a continuation of U.S. applications: U.S. Ser. No. 08/078,476, filed Jun. 17, 1993 (now abandoned), which is a continuation-in-part, U.S. Ser. No. 08/130,735, filed Oct. 1, 1993 (now abandoned).

U.S. Ser. No. 08/078,476 was a continuation-in-part of two applications: U.S. Ser. No. 07/615,719, filed Nov. 21, 1990 (issued as U.S. Pat. No. 5,260,429) and U.S. Ser. No. 08/075,226, filed Jun. 10, 1993 (issued as U.S. Pat. No. 5,401,831). U.S. Ser. No. 08/075,226 and U.S. Ser. No. 07/615,719 both claimed priority (as a division and as a continuation-in-part, respectively) from U.S. Ser. No. 07/479,691, filed Feb. 13, 1990 (issued as U.S. Pat. No. 5,272,058), which was a continuation-in-part of U.S. Ser. No. 07/456,579, filed Dec. 29, 1989 (issued as U.S. Pat. No. 5,004,608), which was a continuation of U.S. Ser. No. 07/143,626, filed Jan. 13, 1988 (abandoned).

All the applications cited above are hereby incorporated by reference in their entireties.

STATEMENT OF RIGHTS TO INVENTIONS MADE UNDER FEDERALLY SPONSORED RESEARCH

This invention was funded in part by contracts (AI 18841 and AI 26649) from the National Institute of Allergy and Infectious Diseases, National Institutes of Health, which provides to the United States government certain rights in this invention.

BACKGROUND OF THE INVENTION

1. Field of the Invention

The invention in the field of infectious diseases and immunology concerns vaccine and diagnostic compositions and methods. The compositions comprise peptides and proteins which include epitope-bearing regions of the 170 kDa subunit (or adhesin) of the *Entamoeba histolytica* Gal/GalNAc adherence lectin. The compositions are produced recombinantly in prokaryotic hosts. These peptides are used to measure subunit-specific antibodies in a subject infected by *E. histolytica* or responding to these vaccines. This invention includes the discovery of a novel variant of the 170 kDa subunit and the gene (hgl3) which encodes it. Hgl3 is the third member of a multigene family each member of which encodes a 170 kDa subunit of the lectin.

2. Description of the Background Art

*Entamoeba histolytica* infection is extremely common and affects an estimated 480 million individuals annually. However, only about 10% of these persons develop symptoms such as colitis or liver abscess. The low incidence of symptoms is thought to be due to the existence of nonpathogenic as well as pathogenic strains of this ameba. As of 1988, it had been established that the subjects who eventually exhibit symptoms harbor pathogenic "zymodemes" classified on the basis of their distinctive hexokinase and phosphoglucomutase isoenzymes. The pathogenic forms are not conveniently distinguishable from the nonpathogenic counterparts using morphogenic criteria, but there is an almost perfect correlation between pathogenicity of the infecting zymodeme and development of symptoms.

It is known that *E. histolytica* infection is mediated at least in part by the "Gal/GalNAc" adherence lectin which was isolated from a pathogenic strain and purified 500 fold by Petri, W. A. et al., *J Biol Chem* (1989) 264:3007–3012. This nomenclature derives from the fact that adherence of the organism to target cells via this lectin is inhibited by the saccharides galactose and N-acetylgalactosamine. The purified lectin was shown to have a nonreduced molecular weight of 260 kDa on SDS-PAGE; reduction with β-mercaptoethanol yielded two subunits having molecular masses of 170 kDa and 35 kDa. The 170 kDa subunit is also referred to herein as the 170 kDa adhesin or the 170 kDa protein. Further studies showed that antibodies directed to the 170 kDa subunit were capable of blocking surface adhesion to test cells (Petri, et al., supra). Therefore, the 170 kDa subunit is believed to be of primary importance in mediating adhesion, hence is designation as the 170 kDa adhesin.

U.S. Pat. No. 5,004,608 (Apr. 2, 1991), describes the entire lectin as an effective vaccine to prevent *E. histolytica* infection.

Studies of serological cross-reactivity of sera from patients having symptoms, characteristic of pathogenic *E. histolytica* infection, including liver abscess and colitis, showed that the adherence lectin was recognized by all sera tested Petri, Jr., W. A. et al., *Am J Med Sci* (1989) 296:163–165). The 170 kDa subunit is recognized almost universally by immune sera and T-cells from patients with invasive amebiasis (Petri et al., *Infect Immun* (1987) 55:2327–2331; Schain et al, *Infect Immun* (1992) 60:2143–2146).

DNA molecules encoding both the heavy (170 kDa) and light (35 kDa) subunits have been cloned. The heavy and light subunits are encoded by distinct mRNAs (Mann, B. et al., *Proc Natl Acad Sci USA* (1991) 88:3248–3252), and these subunits have different amino acid compositions and N-terminal sequences. The sequence of cDNA encoding the 170 kDa subunit suggests that it is an integral membrane protein with a large cysteine-rich extracellular domain and a short cytoplasmic tail (Mann, B. et al., supra; Tannich et al., *Proc Natl Acad Sci USA* (1991) 88:1849–1853). The deduced amino acid sequence of the 170 kDa adhesin shows that the extracellular domain can be divided into three regions based on amino acid composition. The N-terminal amino acids 1–187 are relatively rich in cysteine (3.2%) and tryptophan (2.1%). The convention for amino acid numbering of the 170 kDa subunit is to start with the N-terminus of the mature (processed) protein as #1. The sequence from positions 188–378 lacks cysteine. In the stretch of residues from 379–1209, 10.8% are cysteine. Clones encoding the 170 kDa subunit are further described in U.S. Pat. No. 5,260,429 (Nov. 9, 1993), the disclosure of which is incorporated herein by reference. This patent describes methods for diagnosing the presence of *E. histolytica* using the polymerase chain reaction (PCR) and DNA probes.

The 170 kDa subunit is thought to be encoded by a multigene family (Mann, B. et al., *Parasit Today* (1991) 1:173–176). Two different 170 kDa subunit genes, hgl1 and hgl2, have been sequenced by separate laboratories. While hgl2 was isolated in its entirety from an HM-1:IMSS cDNA library (Tannich, E. et al. *Proc Natl Acad Sci USA* (1991) 88:1849–1853), hgl1 was isolated in part from an H-302:NIH cDNA library and in part by PCR amplification of the gene from the HM-1 :IMSS genome (Mann et al., supra). As the amino acid sequences of these two gene products have 87.6% identity (Mann, B. J. et al. *Parasit Today* (1991) 7:173–176), the differences could be explained by strain variation alone. The presence of multiple bands hybridizing to an hgl probe on Southern blots, however, is consistent with the existence of a gene family (Tannich, E. et al. *Proc Natl Acad Sci USA* (1991) 88:1849–1853).

U.S. Pat. No. 5,272,058 (Dec. 21, 1993; incorporated herein by reference in its entirety) discloses monoclonal antibodies (mAbs) immunoreactive with various epitopes of the 170 kDa subunit. This document also describes use of these antibodies to detect the 170 kDa protein and use of the protein to detect antibodies in serum or other biological samples. It is noteworthy that all the experimental work described in this document was limited to the native protein. These mAbs were further characterized by the present inventors' group (Mann, B. J. et al., *Infect Immun* (1993) 61:1772–1778; also incorporated by reference).

Various immunoassay techniques have been used to diagnose *E. histolytica* infection. *E. histolytica* antigens have been detected by ELISA of stool specimens and sera, though these tests do not seem to distinguish between the pathogenic and nonpathogenic strains. Root et al., *Arch Invest Med* (Mex) (1978) 9: *Supplement* 1:203, described ELISAs with rabbit polyclonal antiserum to detect amebic antigens in stool specimens, and various forms of this procedure have been adapted by others (Palacios et al., *Arch Invest Med* (Mex) (1978) 9 *Supplement* 1:203; Randall et al., *Trans Roy Soc Trop Med Hyg* (1984) 78:593; Grundy, *Trans Roy Soc Trop Med Hyg* (1982) 76:396; Ungar, *Am J Trop Med Hyg* (1985) 34:465). These studies on stool specimens and other biological fluids are summarized in *Amebiasis: Human Infection by Entamoeba histolytica* J. Ravdin, ed. (1988) Wiley Medical Publishing, pp. 646–648.

Serological analysis is also a critical tool in the diagnosis of invasive amebiasis. One approach utilizes conventional serologic tests, such as indirect hemagglutination. These tests are very sensitive, but seropositivity persists for years (Krupp, I. M., *Am J Trop Med Hyg* (1970) 19:5762; Lobel, H. O. et al., *Ann Rev Microbiol* (1978) 32:379–347). Thus, healthy subjects may give positive assay responses, creating an undesirably high background. Similar problems with false positives have been observed in immunoassays using a mAb and purified native 170 kDa protein (Ravdin, J. I. et al., *J Infect Dis* (1990) 162:768–772.)

Recombinant *E. histolytica* proteins other than the 170 kDa subunit have been used as the basis for serological tests. Western blotting using a recombinant form of the "52 kDa serine-rich protein" was highly specific for invasive disease and had a higher predictive value (92% vs. 65%) than an agar gel diffusion test for diagnosis of acute amebiasis (Stanley, Jr., S. L. et al., *Proc Natl Acad Sci USA* (1990) 87:4976–4980; Stanley, Jr., S. L. et al., *JAMA* (1991) 266:1984–1986). However, the overall sensitivity was lower than for the conventional agar gel test (82% vs. 90–100%).

Thus, there remains a need for serological tests which will provide optimal sensitivity while minimizing the number of false positives. The present invention provides such a test by utilizing, as antigen, epitope-bearing portions of the 170 kDa subunit of the adherence lectin produced recombinantly in prokaryotic systems.

It is particularly advantageous to use recombinantly produced, nonglycosylated peptides or proteins in this assay because of the ease of their preparation and standardization. Furthermore, since selected portions of the 170 kDa subunit can be generated, epitopes characteristic of the pathogenic or nonpathogenic forms of *E. histolytica* can be produced and used to distinguish these parasite forms. Subsequent to the making of this invention, Zhang, Y et al. (*J Clin Microimmunol* (1992) 2788–2792) reported on immunoreactivity of immune sera with recombinant 170 kDa protein.

Although it was known that the 170 kDa subunit may be used in a vaccine (U.S. Pat. No. 5,004,608, supra), the present invention, directed to recombinantly produced 170 kDa subunit fragments made in prokaryotic cells and lacking in glycosylation, offers significant advantages in (a) reproducibility of the product, (b) ease of preparation of potent "subunit" vaccines and (c) the biologic (carbohydrate-binding) activity is contained in recombinant product.

Citation of the above documents is not intended as an admission that any of the foregoing is pertinent prior art. All statements as to the date or representation as to the contents of these documents is based on the information available to the applicants and does not constitute any admission as to the correctness of the dates or contents of these documents.

SUMMARY OF THE INVENTION

The invention provides (1) vaccine compositions for prevention of *E. histolytica* infection and (2) diagnostic compositions and assays that permit assessment of subjects for the presence of invasive *E. histolytica* infection. The invention also provides a novel third variant protein of the 170 kDa subunit and a gene (designated hgl3) which encodes this novel protein. Accordingly, the vaccines and diagnostics of the invention are based on the sequences of all three variants of the 170 kDa subunit which are encoded by three different genes of this multigene family.

Pathogenic and nonpathogenic strains of *E. histolytica* can be distinguished by the present diagnostic methods. The tests use as antigen an epitope-bearing protein or peptide of 170 kDa subunit that is preferably recombinantly produced in a prokaryotic system. Despite the absence of glycosylation from such peptides, and despite the lack of post-translational modifications characteristic of the native protein or peptide, such recombinantly produced proteins or peptides are effective antigens in these assays.

Thus, the present invention is directed to a protein or peptide which comprises a 170 kDa subunit of *E. histolytica* adherence lectin or a functional derivative thereof, which protein, peptide or functional derivative:

(a) is nonglycosylated and
(b) bears at least one epitope that reacts with antibodies made in a subject infected with *E. histolytica* infection or immunized with the adherence lectin or a portion thereof.

The protein, or peptide fragment is preferably encoded by one, two or all of the hgl1 gene, the hgl2 gene and the hgl3 gene. The above protein, peptide or functional derivative is preferably produced recombinantly in prokaryotic cells.

The protein may be the full length 170 kDa subunit. Preferably, however, a peptide is a fragment of SEQ ID NO:3 or SEQ ID NO:6 selected from the group consisting of 482–1138, 596–1138, 895–998, 946–970, 976–1000, 991–1015, 1006–1030, 1036–1060, 1033–1082 and 1082–1138 or a functional derivative of any of the foregoing. The functional derivative may be a naturally occurring variant of the peptide fragment. Most preferred is a peptide which has the carbohydrate binding domain of the lectin, and preferably has the sequence of 895–998.

In another embodiment, this invention is directed to a vaccine composition for immunizing a subject against *E.* histolytica infection. The vaccine comprises one or more of the proteins, peptides or functional derivatives described above and a pharmaceutically acceptable vehicle or carrier. A preferred vaccine comprises a fusion protein which includes a peptide fragment as above. The vaccine composition may further comprise an adjuvant or other immune stimulating agent.

Also provided is a method for immunizing a subject against *Entamoeba histolytica* infection which method comprises administering to the subject an effective amount of a vaccine as described above, in particular fragment 895–998 which contains the carbohydrate-binding domain. Vaccination with 895–998 (also designated here as Δ3') will result in an immune response which blocks the carbohydrate-binding activity of the organism which is needed for both colonization and host cell killing.

In yet another embodiment, the invention is directed to an immunoassay method for detecting or quantitating *Entamoeba histolytica*-specific antibodies in a biological sample comprising (a) contacting the sample with an epitope-bearing protein, peptide or functional derivative as described above, under conditions wherein the protein, peptide or functional derivative binds to the specific antibodies immunoreactive to form a complex; and (b) determining the presence or amount of the complex, thereby detecting or quantitating the antibodies.

In the immunoassay method, the protein, peptide or functional derivative is preferably immobilized to a solid support.

A competitive immunoassay format further comprises, during step (a), adding a competing specific binding partner for the epitope, preferably an antibody or antigen binding fragment thereof, more preferably, a detectably labeled antibody. The binding partner competes with antibody in the sample for binding to the epitope.

In the above immunoassay the epitope of the protein, peptide or functional derivative is one which is characteristic of a pathogenic form of *E. histolytica*. Alternatively, the epitope is characteristic of a nonpathogenic form of *E. histolytica* In another embodiment, the epitope is characteristic of both a pathogenic and a nonpathogenic form of *E. histolytica*.

The invention also provides an article of manufacture useful in the above immunoassay method, comprising a solid support or matrix to which is immobilized an epitope-bearing protein, peptide or functional derivative as described above. Also provided is a kit for carrying out the immunoassay, the kit being adapted to receive therein one or more containers, the kit comprising:

(a) a first container containing an epitope-bearing protein, peptide or functional derivative as described above in soluble form, or preferably immobilized to a solid support;

(b) a second container or plurality of containers containing a reagent or reagents capable of detecting or quantitating the binding of the sample antibodies to the epitope-bearing protein, peptide or functional derivative.

In yet another aspect, the invention is directed to a purified and isolated DNA molecule consisting essentially of a DNA encoding the 170 kDa subunit of pathogenic *E. histolytica* adherence lectin. A preferred DNA molecule has the sequence SEQ ID NO:4, the sequence determined for the hgl3 gene. In further aspects, the invention is directed to both nucleic acid and immunological reagents which can be produced in view of the discovery of the hgl3 gene. These reagents are specific for each of the hgl1, hgl2 or hgl3 genes, as well as their RNA or protein products. For example, oligonucleotide probes specific for any one of these three genes or for a sequence common to all three genes may be identified by one of ordinary skill in the art, using conventional nucleic acid probe design principles, by comparisons of the three DNA sequences for these genes. See Example VI.

Detailed descriptions of methods for detecting pathogenic or nonpathogenic forms of *E. histolytica* and antibodies specifically immunoreactive with the Gal/GalNAc lectin derived from *E. histolytica*, as well as reagent kits suitable for the conduct of such methods, are disclosed in U.S. Pat. No. 5,272,058, the entire disclosure of which is incorporated herein by reference.

BRIEF DESCRIPTION OF THE DRAWINGS

FIG. 1A (sheets FIG. 1A-1 through FIG. 1A-6) shows the nucleotide sequence (SEQ ID NO: 1) and deduced amino acid sequence (SEQ ID NO:2) from the DNA encoding the 170 kDa subunit of the adherence lectin from pathogenic strain HM1:IMSS, designated hgl1.

FIG. 1B shows the deduced amino acid sequence (SEQ ID NO:2) of the hgl1 encoded protein (1291 residues) with the N-terminal amino acid of the mature protein numbered as residue 1. The mature protein has the sequence SEQ ID NO:3.

FIGS. 4A–4F shows the nucleotide sequence (SEQ ID NO:4) of DNA encoding the 170 kDa subunit of the adherence lectin from pathogenic strain HM1:IMSS, designated hgl3 and the deduced amino acid sequence (SEQ ID NO:5) encoded thereby.

FIG. 5 shows the deduced amino acid sequence (SEQ ID NO:5) encoded by hgl3 with the N--terminal amino acid of the mature protein numbered as residue 1. The putative signal sequence is overlined, and the putative transmembrane domain is underlined. Conserved cysteine residues (●) and potential sites of glycosylation (★) are indicated. The mature protein has the sequence SEQ ID NO:6.

DESCRIPTION OF THE PREFERRED EMBODIMENTS

Figure 2A:
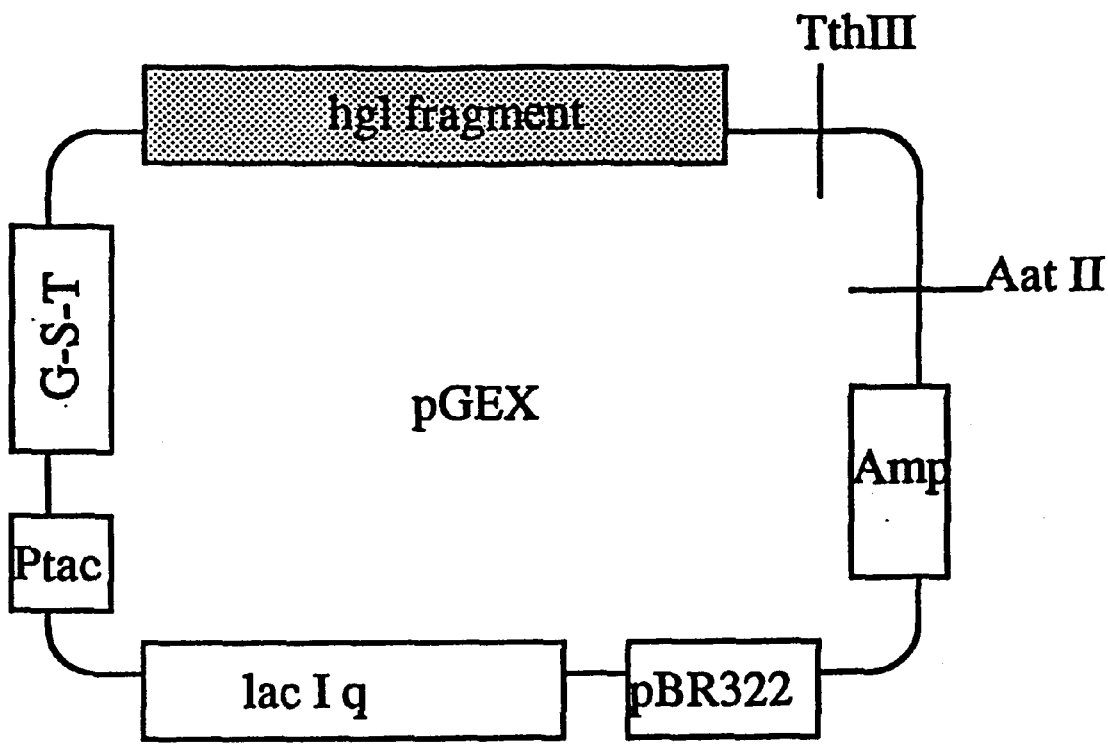
FIG. 2 is a diagram of the construction of expression vectors for recombinant production of specified portions of the 170 kDa subunit

This invention provides vaccine and diagnostic compositions and methods. Diagnostic methods detect antibodies specific for pathogenic and/or nonpathogenic forms of *E. histolytica* and are conducted on biological samples derived from subjects at risk for infection or suspected of being infected. The assays are also designed to distinguish pathogenic from nonpathogenic forms of the ameba. The vaccines compositions are administered to subjects at risk for *E. histolytica* infection.

The assays of the invention rely on the ability of an epitope-bearing fragment of the 170 kDa subunit, produced recombinantly in prokaryotic cells, to react immunologically with antibodies in biological samples from infected individuals. Even though the preferred peptide or protein is produced in a prokaryotic system, and is thus not glycosylated or processed after translation in the same way as the native protein, the epitope-bearing fragments are nevertheless useful as antigens in these immunoassays. "Biological samples" include (a) biological fluids such as blood, serum, urine or cerebrospinal fluid, (b) diluted or fractionated forms of such fluids, (c) cells, tissues or organs, or extracts or lysates thereof. These epitope-bearing peptides are also immunogenic or can be made immunogenic by coupling to an appropriate carrier, and are therefore used in vaccine preparation as well.

The advantages of the recombinant forms of the 170 kDa fragments as antigens include cost-effectiveness and reliable production of pure material, thereby assuring uniformity of vaccine or diagnostic assay compositions. Importantly, the Δ3' fragment (aa-895–998) has the GalNAc-binding activity of specificity identical to that of the native lectin. Recombinant production in bacteria is particularly efficient and preferred. It is surprising that successful antigens and immunogens can be made in such prokaryotic hosts, since the peptides are not processed in a manner analogous to the native protein. Recombinant methods also facilitate the preparation of single epitopes or selected combinations of epitopes, thereby providing a means for detecting antibodies specific for pathogenic or nonpathogenic forms of the organism. Such recombinant production allows preparation of subunit vaccines with the desired epitope or combination of epitopes.

Thus, the invention is directed chiefly to (1) recombinantly produced peptides and materials useful as vaccine compositions and as diagnostic reagents, (2) methods to immunize subjects at risk of infection with such vaccine compositions, and (3) methods to evaluate biological samples for the presence of antibodies or 170 kDa subunit antigens using these recombinantly produced diagnostic reagents.

Definitions

The diagnostic assays may be designed to distinguish antibodies raised against nonpathogenic or pathogenic forms of the ameba. "Pathogenic form" of *E. histolytica* refers to those forms which are invasive and result in symptoms in infected subjects. "Nonpathogenic form" refers to those forms which may be harbored asymptomatically by carriers of the infection.

The assays and vaccines of the invention utilize an epitope-bearing "portion," "fragment" or "peptide" of the 170 kDa subunit of the Gal/GalNAc lectin, a glycoprotein found on the surface of *E. histolytica* which mediates the adherence of the amebas to target cells, and which adherence is inhibited by the saccharides Gal or GalNAc. The "lectin," as the term is used herein, is the molecule isolated by Petri et al. (supra) from the pathogenic strain HMI-IMSS of *E. histolytica*, or is the corresponding or homologous glycoprotein found in other strains of *E. histolytica*.

The "170 kDa subunit" refers to the large subunit obtained upon reduction of the Gal/GalNAc lectin, such as that obtained by Petri et al. (supra), the amino acid sequence of which may be SEQ ID NO:3 or SEQ ID NO:6, as well as to its counterparts in other strains. See, also, FIGS. 1A (sheets 1A-1–1A-6), FIG. 1B, and FIGS. 4A–F and FIG. 5.

Diagnostic Assays

The complete 170 kDa subunit (antigen) or an epitope-bearing fragment thereof can be used in the present assays. The peptide, and therefore, the epitope(s) may be selected to configure an assay that detects pathogenic strains, nonpathogenic strains or both. This is accomplished by selecting strain-specific epitopes. To detect infection by either or both types of amebae in a single assay, either a combination of epitopes, or an epitope(s) common to both pathogenic and nonpathogenic strains, are used.

As shown below, the segments of the 170 kDa protein which contain epitopes reactive with all mAbs prepared thus far against the complete lectin subunit are found between amino acid positions 596 and 1138 (SEQ ID NO:3). An epitope characteristic of pathogens is found in peptide fragments 596–818, 1082–1138 and 1033–1082. Epitopes which are shared by pathogens and nonpathogens as well as epitopes characteristic of pathogens are found in peptide 896–998. Thus, an assay to detect antibodies against pathogens using a fragment of recombinantly produced 170 kDa protein preferably employs a peptide representing positions 596–818, 895–998, 1033–1082 or 1082–1138. Mixtures of the above peptides may also be used. Alternatively, longer forms of antigen can be used by selecting and combining the appropriate peptides depending on whether infections with pathogenic or nonpathogenic amebae are to be diagnosed.

As shown in Examples IV, V, VII and VIII, below, useful epitope-bearing fragments for serodiagnosis include peptides 2–482, 1082–1138, 1032–1082 and 895–998. Peptides 1082–1138 and 1032–1082 appear to be recognized by antibodies against pathogenic amebae. These epitope-bearing peptides may be used as single peptides, basically as they appear in the lectin, or as portions of chimeric or fusion proteins, as mixtures of peptides or of chimeric proteins, or as portions of a distinct protein construct bearing multiple epitopes not necessarily ordered relative to one another in the same order in which they exist in the native protein. Procedures for preparing recombinant peptides and proteins containing only a single epitopic fragment, as identified above, or containing multiples of such epitopic fragments (including tandem repeats) are routine in the art.

Fusion proteins between GST and epitopes of the present invention have been exemplified in several of the Examples herein. Other fusion proteins can be used to enhance antigenicity. Thus, heterologous oligopeptide epitopes of immunological interest have been inserted in-frame into bacterial flagellin (Newton, S. et al, (1989) *Science* 244:70–72; Jennings et al., (1989) *Protein Eng.* 2:365), influenza virus nucleoprotein (Chimini, G. et al. (1989) *J. Exp. Med.* 169:97–302), hepatitis B surface antigen (Rutgers et al., (1988) *Bio/Technology* 6:1065) and in the complementarity determining regions (CDR) of immunoglobulin (Ig) molecules (Billetta, R. et al., (1991) *Proc. Natl. Acad. Sci. USA* 88:4713–4717; Zanetti et al. (1992) *Nature,* 355:476; Zanetti et al. WO90/090804); Zaghouani, H. et al. (1993) *Science* 259:224–227; Zaghouani, H. et al., (1993) *Int. Rev. Immunol.* 10:265–278; Zaghouani, H. et al. (1995) *Proc. Natl. Acad. Sci. USA* 92: 631–635). Such a recombinant protein can induce an enhanced immune response to the heterologous oligopeptide. (See, also, Zauderer, M., *Nature Biotechnol.* (1996) 12:703–704, and the references cited therein)

Thus in the present invention, a peptide-immunoglobulin fusion protein is used to induce immunity following the approach described by Billetta et al., supra. There, a fusion Ig was made which expressed in the CDR3 of its $V_H$ region the repetitive tetrapeptide Asn-Ala-Asn-Pro (designated $(NANP)_n$) of the circumsporozoite protein of *Plasmodium falciparum*, an etiologic agent of malaria. Immunization of rabbits and mice with the engineered fusion Ig in adjuvant elicited antibodies to the $(NANP)_3$ synthetic peptide and to *P. falciparum* parasite. Such antibodies efficiently inhibited the invasion of cultured liver cells by *P. falciparum*. Thus, immunity to malaria was induced in the absence of the parasite using antibody V regions engineered to mimic the parasite's molecular structure. C. Bona et al., (1994) *Cell Mol. Biol.* 40 *Suppl* 1:21–30 expressed viral epitopes on Ig molecules by replacing the D segment of a $V_H$ gene with (a) a B cell epitope from the V3-loop of HIV-1 gpl20, (b) a cytotoxic T lymphocyte-epitope from influenza virus nucleoprotein or (c) a T helper epitope from influenza hemagglutinin. The T cell-targeted fusion Ig molecules (produced by cells transfected with chimeric genes) activated specific T cells. The authors suggested practical applications for Ig molecules bearing foreign epitopes for the development of prophylactic and immunotherapeutic reagents. In summary, it is known that recombinant fusion proteins, including fusion Ig proteins, may be useful immunogens to induce immune responses to a heterologous oligopeptide. Hence, an immunogenic fusion Ig is made with a desired epitope-bearing fragment of the 170 kDa subunit by conventional recombinant techniques. This protein can serve as a vaccine composition in accordance with this invention.

The present assays are designed to detect in biological samples antibodies which are "immunospecific for" or "immunoreactive with" the epitope-bearing fragment—i.e., having at least one epitope contained in this fragment. As used herein, an "immunospecific" or "immunoreactive" antibody binds to its target with significantly higher affinity or avidity compared to its binding to any other antigen, hapten or epitope. The degree of specificity required may vary with circumstances, but typically an antibody immunospecific for a designated target will bind to that target with an affinity which is at least one, preferably two, or more preferably greater than 2 orders or magnitude higher than its affinity for alternate targets for which is not "specific."

The present assays can be performed using a wide variety of protocols depending on the nature of the sample, the circumstances of performing the assays, and the particular design chosen by the practitioner. The biological sample is prepared in a conventional manner for immunoassays; such preparation may involve dilution or fractionation of the biological fluid or initial cell, tissue or organ extract. A "biological sample" refers to the sample actually used in the assay whether it is derived from a fluid, cells, tissue or an organ of a subject and prepared for use in the assay using any known technique. Normally, plasma or serum is the preferred source of the biological sample. For a detailed discussion of immunoassays, including ELISA, use of immobilized antigens and antibodies, conventional solid supports, and the like, see, for example Hartlow, E. et al., *Antibodies: A Laboratory Manual,* Cold Spring Harbor Laboratory Press, Cold Spring Harbor, N.Y., 1988); Monroe, D., *Anal. Chem.* 56: 920A–931A (1984); Voller, A et al. (eds)., *Immunoassays for the 1980's,* University Park Press, Baltimore, Md., 1981; Butt, W. R. (ed.) *Practical Immunoassay: The State of the Art,* Dekker, New York, 1984; Bizollon, C., ed., *Monoclonal Antibodies and New Trends in Immunoassays,* Elsevier, New York, 1984; Butler, J. E., The Behavior of Antigens and Antibodies Immobilized on a Solid Phase (Chapter 11) In: *Structure of Antigens,* Vol. 1 (Van Regenmortel, M., CRC Press, Boca Raton 1992, pp. 209–259; Butler, J. E., ELISA (Chapter 29), In: van Oss, C. J. et al., (eds), *Immunochemistry,* Marcel Dekker, Inc., New York, 1994, pp. 759–803; Butler, J. E. (ed.), *Immunochemistry of Solid-Phase Immunoassay,* CRC Press, Boca Raton, 1991; Maggio, E. (ed.), *Enzyme Immunoassay,* CRC Press, Boca Raton, 1980; Weintraub, B., *Principles of Radioimmunoassays,* Seventh Training Course on Radioligand Assay Techniques, The Endocrine Society, March, 1986; Work, T. S. et al., *Laboratory Techniques and Biochemistry in Molecular Biology,* North Holland Publishing Company, NY, (1978.)

The assays may be conducted in a competition format employing a specific binding partner for the epitope-bearing portion. As used herein, "specific binding partner" refers to a substance which is capable of binding specifically to a targeted substance, such as an epitope-bearing peptide of the 170 kDa subunit. Commonly, such a specific binding partner is an antibody, but any alternative substance capable of such specific binding, such as a receptor, enzyme or any other chemical compound with the requisite property may be used. In this context, "antibody" refers not only to an intact immunoglobulin (Ig) molecule with two heavy and two light chains, but also to Ig fragments which retain the antigen-binding specificity of the intact antibody molecule. Examples of such fragments are well known in the art, and include, for example, Fab, Fab', F(ab')$_2$ and Fv fragments. The term "antibody" includes not only native forms of Ig, but forms which have been modified, as techniques become available in the art, to confer desired properties without altering the specificity. For example, the chimeric antibodies derived from two different species, such as mouse and man, are becoming more practical (e.g., Cabilly et al., U.S. Pat. No. 4,816,567; Taniguchi et al., EP171496; Morrison et al., EP173494; Neuberger et al., WO8601533; Robinson et al., WO 8702671). Single chain antibodies are known (U.S. Pat. No. 4,946,778). In short, "antibody" refers to any component of, or derivative of an Ig molecule which retains the antigen binding specificity of the Ig.

A particularly useful type of antibody in the assay methods of the invention is a mAb. Three groups of mAbs have been prepared to the 170 kDa subunit. One group is immunospecific for epitopes "unique" to pathogenic forms. These mAbs therefore bind to a significant extent only to the pathogenic forms of the ameba or the 170 kDa subunit isolated from pathogenic forms. A second group is immunoreactive with epitopes "unique" to nonpathogenic forms. Thus, these mAbs bind to a substantial degree only to the nonpathogenic ameba or their lectins but not to the pathogenic forms. A third group of mAbs binds to epitopes shared among pathogenic and nonpathogenic strains and are thus capable of binding to an ameba, a subunit or a fragment, regardless of the organism's pathogenicity.

As shown in Table 1, below, seven different epitopes (designated by the numbers 1–7) of the 170 kDa subunit have been defined based on the reactivity patterns of seven different mAbs. The mAbs reactive with epitopes 1 and 2 of the subunit isolated from the pathogenic-strain react also with the corresponding epitopes on nonpathogens. On the other hand, those mAbs immunoreactive with epitopes 3–6 react only with the 170 kDa subunit of pathogenic strains. Techniques for isolating the subunit of pathogenic amebae is therefore used to isolate the 170 kDa subunit from nonpathogenic strains. This isolated material is then used to immunize animals and generate new mAbs immunoreactive with "counterpart" epitopes 3–6 of the 170 kDa subunit of nonpathogenic organisms.

Of course, antibodies found in a biological sample, in general, will be intact Ig molecules. However, pretreatment of the sample with an enzyme, for example, an enzyme which removes the Fc portion of the antibodies contained therein, does not destroy the sample's ability to react in the assay.

Assay Procedure

For the conduct of the present immunoassays, in general, the biological sample is contacted with an epitope-bearing peptide of the invention. The presence, absence or amount of the resulting immune complex formed between an antibody in the sample and the peptide is measured directly or in a competitive format.

As is well understood in the art, once the biological sample is prepared, a multiplicity of alternative protocols may be used to conduct the assay. In a preferred protocol, the epitope-bearing peptide is immobilized to a solid support, either by adsorption or by covalent linkage, and incubated with the biological sample. Any specific antibodies in the sample will bind to the peptide and become immobilized. Their presence on the solid support is then determined. This binding may be determined in by "direct" assay of the sample antibody bound to the support. In one particularly convenient format, the antigen is immobilized as a band on polyvinylidene difluoride (PVDF) (or other) membrane and contacted with the biological sample. Any antibody binding to the PVDF membrane is detected as described herein for Western blot procedures. This protocol is, in fact, a modified Western blot procedure without the electrophoretic step. Alternatively, microtiter plates or other suitable solid supports may be used.

The binding of antibody to the immobilized antigen is detected using conventional techniques. These generally involve a secondary labeling agent, for example, labeled a reagent comprising antibodies specific for the Ig species (e.g., human Ig for a human sample) or the Ig isotype or an Ig allotype. Detectable labels include radioisotopes, fluorescent tags, enzyme labels and the like, as is conventionally understood.

The assay may also be formatted as a competitive assay wherein the immobilized antigen (epitope-bearing fragment) is allowed to react with the biological sample in the presence of a competing specific binding partner for at least one epitope contained in the antigen. The competing binding partner is preferably an antibody. The competing antibody may be polyclonal or monoclonal and may itself be labeled or may be capable of being labeled in a secondary reaction. In a typical competitive assay, the competing binding partner is detectably labeled. Successful competition with antibodies in the biological sample is measured as a reduction in the amount of label bound in the resulting complex (or, alternatively as an increase in the amount of label remaining unbound in the supernatant. If mAbs are used, the assay can readily be adapted for antibodies reactive to pathogenic or nonpathogenic amebic strains by choosing competing antibodies of the appropriate specificity. Thus, if the assay is to be specific for antibodies against pathogenic *E. histolytica*, the competitor is a mAb specific for an epitope characteristic of pathogenic strains.

The assay may also be made specific for pathogenic vs. nonpathogenic strains by the choice of the epitope-bearing fragment. If antibodies specific to the pathogens are to be detected, the epitope-bearing peptide(s) chosen bears only an epitope(s) characteristic of pathogenic strains. Conversely, detection of antibodies specific for nonpathogens requires that the peptide(s) comprise an epitope(s) characteristic of nonpathogens. Where such distinction among antibodies is unnecessary, the antigen used in the assay may contain either or both types of epitopes.

In another embodiment, the antibody-containing biological sample is immobilized to a solid support, and the desired epitope-bearing peptide or protein, preferably having at least two epitopes, is added under conditions wherein the epitope) binds to the immobilized sample antibody. Addition of a detectably labeled second antibody specific for an epitope of the now bound antigen different from the epitope bound by the sample antibody) will result in binding of the label to the solid phase, thereby detecting the presence of antigen bound to the immobilized sample antibody.

In summary, the biological sample to be tested is contacted with the epitope-bearing fragment from a pathogenic or nonpathogenic strain of *E. histolytica* so that a complex is formed. The complex is then detected by suitable labeling, either of the *E. histolytica* antigen or of a secondary detection molecule which forms a ternary complex. The reaction is preferably conducted using a solid support to detect the formation of the complex attached to the support. Alternatively, the complex can be precipitated using conventional precipitating agents such as polyethylene glycol.

In a more complex, competitive assay, the biological sample, preferably serum or plasma, provides the unlabeled antibody which competes with a specific binding partner, preferably a labeled mAb specific for an epitope unique to the Gal/GalNAc lectin or its 170 kDa subunit. In this embodiment, the binding of the labeled specific mAb is conducted in the presence and absence of the biological sample, and the diminution of labeling of the resulting complex by the sample is a measure of the level of competing antibodies present in the sample.

Kits suitable for the conduct of the foregoing assays include the appropriate labeled antigen or antibody reagents and instructions for conducting the test. The kit may include the antigen coupled to solid support as well as additional reagents.

Vaccine Compositions

The recombinant 170 kDa subunit or an epitope-bearing peptide thereof is used as the active ingredient of a vaccine composition. A preferred region of the protein is from 482–1138 (of SEQ ID NO:2) which includes the cysteine-rich domain. This region is encoded by nucleotides 1492–3460 of SEQ ID NO: 1. More preferred "subregions" of the 482–1138 fragment are the following regions: 596–1138, 885–998, 1033–1082 and 1082–1138. One particularly preferred peptide is 895–998, which is advantageously prepared as a larger construct comprising multiple repeats of one or more of these epitopic regions.

Additional short peptide epitopes useful in vaccine compositions have been found (Lotter, H. et al., *J. Exp. Med.* (1997) 185:1793–1801) to react with antibodies from gerbils vaccinated with recombinant fragments corresponding to domains of the 170 kDa subunit which have been discovered by the present inventors to be efficacious vaccine preparations. Such peptides, corresponding to regions in the "C-Rich" domain (FIG. 3) include:

known in the art, and are described in the following references, hereby incorporated by reference: Merrifield, B., *J. Amer. Chem. Soc.* 85:2149–2154 (1963); Merrifield, B., *Science* 232:341–347 (1986); Wade, J. D. et al., *Biopolymers* 25:S21–S37 (1986); Fields, G. B., *Int. J. Peptide Prot. Res.* 35:161 (1990); MilliGen Report Nos. 2 and 2a, Millipore Corporation, Bedford, Mass., 1987). For example, the more classical method, "tBoc method," or the more recent improved "F-moc" technique may be used (Atherton, E. et al., *J. Chem. Soc. Perkin Trans.* 1:538–546 (1981)).

A preferred group of variants are peptides in which at least one amino acid residue and preferably, only one, has been removed and a different residue inserted in its place. For a detailed description of protein chemistry and structure, see Schulz, G. E. et al., *Principles of Protein Structure*,

| PEPTIDE | SEQ ID NO: | SEQUENCE |
|---|---|---|
| 946–970 | 3 or 6 | Asp Pro Asn Phe Asp Cys Gln Pro Ile Glu Cys Lys Ile Gln Glu Ile Val Ile Thr Glu Lys Asp Gly Ile Lys |
| 976–1000 | 3 | Asn Thr Thr Lys Ala Thr Cys Asp Thr Asn Asn Lys Arg Ile Glu Asp Ala Arg Lys Ala Phe Ile Glu Gly Lys |
|  | 6 | Asn Thr Thr Lys Thr Thr Cys Asp Thr Asn Asn Lys Arg Ile Glu Asp Ala Arg Lys Ala Phe Ile Glu Gly Lys |
| 991–1015 | 3 or 6 | Asp Ala Arg Lys Ala Phe Ile Glu Gly Lys Glu Gly Ile Glu Gln Val Glu Cys Ala Ser Thr Val Cys Gln Asn |
| 1006–1030 | 3 or 6 | Val Glu Cys Ala Ser Thr Val Cys Gln Asn Asp Asn Ser Cys Pro Ile Ile Thr Asp Val Glu Lys Cys Asn Gln |
| 1036–1060 | 3 or 6 | Tyr Gly Cys Lys Ala Met Thr Gly Glu Cys Asp Gly Thr Thr Tyr Leu Cys Lys Phe Val Gln Leu Thr Asp Asp |

For use in vaccines, the full 170 kDa subunit or an epitope-bearing peptide thereof is produced recombinantly, preferably in prokaryotic cells. The recombinant product is administered as a protein or peptide vaccine. In another embodiment, the vaccine is in the form of a strain of bacteria (preferably a known "vaccine strain") which has been genetically transformed to express the epitope-bearing peptide. Some known vaccine strains of Salmonella are described in Example VIII and in references cited therein. It may be practical to prepare the peptide by chemical synthesis if is sufficiently short, using methods described below.

Any functional derivative of the 170 kDa adhesin is intended within the scope of the invention. "Functional derivative" as used herein means a "fragment," a "variant," a "homologue," an "analogue," or a "chemical derivative" of the 170 kDa adhesin, which terms are defined below. A functional derivative retains at least a portion of the function of the 170 kDa adhesin which permits its utility in accordance with the present invention. Generally, this means that at least that portion of the sequence which is needed to retain the requisite biochemical and biological activity, in particular the antigenicity and immunogenicity.

A "fragment" of the 170 kDa adhesin refers to any subset of the molecule, that is, a shorter peptide, and is the preferred functional derivative.

A "variant" of the 170 kDa adhesin refers to a molecule substantially similar to either the entire protein or to a peptide fragment thereof. Variant peptides may be conveniently prepared by recombinant methods or by direct chemical synthesis on solid phase supports and their subsequent separation from the support. Such methods well- Springer-Verlag, New York, 1979, and Creighton, T. E., *Proteins: Structure and Molecular Principles*, W. H. Freeman & Co., San Francisco, 1984, which are hereby incorporated by reference. The types of substitutions which may be made in the peptide molecule of the present invention are conservative substitutions and are defined herein as exchanges within one of the following groups:

1. Small aliphatic, nonpolar or slightly polar residues: e.g., Ala, Ser, Thr, Gly;
2. Polar, negatively charged residues and their amides: e.g., Asp, Asn, Glu, Gln;
3. Polar, positively charged residues: e.g., His, Arg, Lys;
4. Large aliphatic, nonpolar residues: Met, Leu, Ble, Val (Cys); and
5. Large aromatic residues: Phe, Tyr, Trp.

Pro, because of its unusual geometry, tightly constrains the chain. Substantial changes in functional properties are made by selecting substitutions that are less conservative, such as between, rather than within, the above groups (or two other amino acid groups not shown above), which will differ more significantly in their effect on maintaining (a) the structure of the peptide backbone in the area of the substitution (b) the charge or hydrophobicity of the molecule at the target site, or (c) the bulk of the side chain. Most substitutions according to the present invention are those which do not produce radical changes in the characteristics of the peptide molecule. Even when it is difficult to predict the exact effect of a substitution in advance of doing so, one skilled in the art will appreciate that the effect can be evaluated by routine screening assays, preferably the immunoassays described herein. Modifications of peptide properties including redox or thermal stability, hydrophobicity, susceptibility to proteolytic degradation or the tendency to aggregate with carriers or into multimers are assayed by methods well known to the ordinarily skilled artisan.

The term "homologue" as used here in is well-defined in the art, and can be described (at the protein level) as the product any member of a set of genes or DNA sequences from different organisms whose nucleotide sequences show a high degree of one-to-one correspondence with the DNA encoding the 170 kDa subunit. (See, for example, Micklos, D. A. et al., DNA SCIENCE, Cold Spring Harbor Press, 1990, p. 468). In particular, the 170 kDa subunit protein (or DNA coding therefore) from phylogenetically related amebic species is considered to be a homologue of the protein (or DNA) may be used.

An "analogue" of the 170 kDa subunit refers to a non-natural molecule substantially similar to either the entire molecule or to a fragment thereof.

A "chemical derivative" of the 170 kDa subunit contains additional chemical moieties not normally a part of the peptide. Covalent modifications of the peptide are included within the scope of this invention. Such modifications may be introduced into the molecule by reacting targeted amino acid residues of the peptide with an organic derivatizing agent that is capable of reacting with selected side chains or terminal residues.

Production of Recombinant Epitope-Bearing Compositions

The epitope-bearing portions of the 170 kDa subunit can be conveniently prepared in a variety of prokaryotic systems using control sequences and hosts well known and readily available in the art. The epitope-containing peptides may be fusion proteins or mature proteins which are produced intracellularly or are secreted. Techniques for constructing appropriate expression systems are well known in the art. If the epitope-bearing peptide is secreted, the culture medium can be used directly as a source of antigen in the assays described above. The antigen can also be recovered from the medium and further purified if desired. If the protein is produced intracellularly, lysates of cultured cells may be used directly or after further purification. In the Examples below, the epitope-bearing fragment is provided as a fusion protein using the commercially available expression vector, pGEX. Alternative constructs and alternative hosts can also be used as is understood in the art.

Methods of Protecting a Subject from Infection

The present vaccine compositions are used primarily for prevention of E. histolytica infection in subjects at risk for such an infection. Full length subunit or large fragments of the 170 kDa protein can be used as immunogens. If a shorter epitope-bearing fragment, for example containing 20 amino acids or less, is the active ingredient of the vaccine, it is advantageous to couple the peptide to an immunogenic carrier to enhance its immunogenicity. Such coupling techniques are well known in the art, and include standard chemical coupling techniques using linker moieties such as those available from Pierce Chemical Company, Rockford, Ill. Suitable carriers are proteins such as keyhole limpet hemocyanin (KLH), E. coli pilin protein k99, BSA, or rotavirus VP6 protein.

Another embodiment is a fusion protein which comprise the epitope-bearing peptide region fused linearly to an additional amino acid sequence. Because of the ease with which recombinant materials can be manipulated, multiple copies a selected epitope-bearing region may be included in a single fusion protein molecule. Alternatively, several different epitope-bearing regions can be "mixed and matched" in a single fusion protein.

The active ingredient, or mixture of active ingredients, in the vaccine composition is formulated conventionally using methods well-known for formulation of protein or peptide vaccines. Vaccine compositions may include an immunostimulant or adjuvant such as complete or incomplete Freund's adjuvant, aluminum hydroxide, liposomes, beads such as latex or gold beads, ISCOMs, and the like. General methods to prepare vaccines are described in Remington's Pharmaceutical Science; Mack Publishing Company Easton, Pa. (latest edition). Liposomes are pharmaceutical compositions in which the active protein is contained either dispersed or variously present in corpuscles consisting of aqueous concentric layers adherent to lipidic layers. The active protein is preferably present in the aqueous layer and in the lipidic layer, inside or outside, or, in any event, in the non-homogeneous system generally known as a liposomic suspension. The hydrophobic layer, or lipidic layer, generally, but not exclusively, comprises phospholipids such as lecithin and sphingomyelin, steroids such as cholesterol, more or less ionic surface active substances such as dicetylphosphate, stearylamine or phosphatidic acid, and/or other materials of a hydrophobic nature. Adjuvants, including liposomes, are discussed in the following references, incorporated herein by reference: Gregoriades, G. et al., Immunological Adjuvants and Vaccines, Plenum Press, New York, 1989 Michalek, S. M. et al., "Liposomes as Oral Adjuvants," Curr. Top. Microbiol. Immunol. 146:51–58 (1989).

The vaccine compositions preferably contain (1) an effective amount of the active ingredient, that is, the peptide or peptides, together with (2) a suitable amount of a carrier vehicle, and, if desired, (3) preservatives, buffers, and the like. Descriptions of vaccine formulations are found in Voller, A. et al., New Trends and Developments in Vaccines, University Park Press, Baltimore, Md. (1978).

The vaccines are administered as is generally understood in the art. Ordinarily, systemic administration is by injection; however, other effective means of administration are known. With suitable formulation, peptide vaccines may be administered across the mucus membrane using penetrants such as bile salts or fusidic acids in combination, usually, with a surfactant. Transcutaneous administration of peptides is also known. Oral formulations can also be used. Dosage levels depend on the mode of administration, the nature of the subject, and the nature of carrier/adjuvant formulation. Preferably, an effective amount of the protein or peptide is between about 0.01 $\mu$g/kg–1 mg/kg body weight. In general, multiple administrations of the vaccine in a standard immunization protocol are used, as is standard in the art.

Induction of Immunological Tolerance to "Enhancing" Epitopes

Antibodies specific for certain epitopes in certain regions of the 170 kDa subunit, in particular the C-W domain (in the vicinity of residues 1–436) act to enhance amebic adherence, thereby promoting the infectivity and pathology. The present invention provides an additional approach to preventing infection by selectively inhibiting the generation of antibodies with such specificity. Thus, in conjunction with the vaccines are provided tolerogenic compositions capable of inducing and maintaining epitope-specific tolerance in a subject.

Immunological tolerance is known to be inducible by attaching an epitope to be tolerated to isologous or heterologous Ig molecules, primarily of the IgG isotype (Borel, Y. (1980) *Immunol. Rev.* 50:71; Scott, D. W. (1976) *Cell Immunol.* 22:311). Such molecules are termed "tolerogenic carriers" or "tolerogens" (Scott, D. W. (1979) *Immunol. Rev.*

43:241). These carriers owe their superior tolerogenicity to their persistence in vivo and the ability of an epitope chemically coupled to the IgG molecule to crosslink membrane IgM on the surface of B lymphocytes with surface Fc receptors. However, chemical coupling of epitopes to IgG carriers can be limited by the availability of free reactive amino groups, structural change of the epitope as a result of the coupling reaction, and the uncontrolled targeting of the added epitope to different (disadvantageous) sites of the IgG molecule. Protein engineering strategies are used to create molecules containing heterologous epitopes. This has been discussed above for the amplification of specific immune responses. Recently, however, strategies for fusing DNA encoding a desired epitope to an Ig H chain gene to create tolerogenic fusion Ig's have been described (Scott and Zambidis, WO95/21926; Zambidis, E. T. et al., (1996) *Proc. Natl. Acad. Sci. USA* 93:5019–5024; Zambidis, E. T. et al., *J. Immunol.* (1997) 158:2174–2182; Zambidis, E. T. et al., *Mol. Med.* (1997) 3:212–24)). By fusing an otherwise immunodominant epitope (termed 12–26) of the phage λcI repressor protein to the N-terminus of an Ig H chain, Scott, Zambidis and coauthors induced epitope-specific tolerance. Hematopoietic progenitor cells or B cells transfected using a retroviral vector expressed the fusion protein which could be used to induce tolerance by administration to a subject. More importantly, long lasting tolerance could be induced and maintained in an immunocompetent recipient by transfer of such hematopoietic progenitor cells or resting or activated B cells which had been transfected with the engineered fusion Ig to express this tolerogenic construct. Certain of these compositions could even overcome a state of pre-existing immunity.

Thus, according to the present invention, it is desired to induce tolerance to one or more peptides from the C-W domain of the 170 kDa subunit (or any other epitopes in other regions which are found to be associated with undesired "enhancing" antibodies that promote pathogenesis). A fusion Ig is made with the selected single epitope or combination of epitopes. The DNA encoding these epitopes is fused in-frame in the variable (V) region of a gene encoding an Ig chain (H or L), preferably the $V_H$ gene. An effective amount of this tolerogenic fusion protein, or of appropriate cells, preferably hematopoietic progenitors or B cells, expressing the fusion protein, are administered to a subject susceptible to infection with *E. histolytica*. This treatment can be given alone in conjunction with a vaccine directed to epitopes which are associated with protective immunity, such as the vaccine epitopes discussed herein.

An example of a preferred tolerogenic peptide is one corresponding to residues which are associated with an adherence-enhancing antibody response such as residues 436–624 of hgl2 (corresponding to 443–461 of hgl1) or the peptides recognized by the enhancing mAbs indicated in Table 1, below.

Treatment of a subject using the tolerogenic fusion Ig comprises parenterally administering a single or multiple doses of the fusion Ig to the subject, preferably a human. The fusion Ig is preferably an isologous Ig, that is, of the same species as the subject, most preferably human. Most preferred is a fusion IgG molecule. An effective tolerogenic dose is a function of the size and number of particular epitopes included in a particular fusion construct, the subject and his clinical status, and can vary from about 0.01 mg/kg body weight to about 1 g/kg body weight. A subject can be given this amount in a single dose or in multiple repeated doses. Doses of hematopoietic cells or B cells expressing the fusion Ig are preferably administered at a dose of between about $10^6$ and about $10^{10}$ cells on one or several occasions. The route of administration may include intravenous (iv), subcutaneous (sc), intramuscular, intrapulmonary, intraperitoneal or other known routes. The preferred route for administration of such proteins or cells for tolerogenesis is by iv injection.

Reagents and Assays for a Novel 170 kDa Lectin Subunit

To discover the existence and determine the complexity of the 170 kDa subunit gene family, hgl, an amebic genomic library in lambda phage was hybridized with DNA fragments from the 5' or 3' ends of hgl1. Termini from three distinct 170 kDa subunit genes were identified including hgl1, hgl2, and a third, previously unreported gene designated hgl3. The open reading frame of hgl3 was sequenced in its entirety (FIGS. 4A–F; SEQ ID NO:4). Nonstringent hybridization of a genomic Southern blot with 170 kDa subunit-specific DNA labeled only those bands predicted by hgl1–3. The amino acid sequence encoded by hgl3 FIGS. 4A–F; SEQ ID NO:5) was 95.2% identical to that encoded by hgl1 and 89.4% identical to that encoded by hgl2. All 97 cysteine residues in the 170 kDa subunit were conserved in hgl1–3. Nucleotide sequences for two additional members of this gene family, hgl4 and hgl5 are disclosed in a paper by the present inventors' laboratory (Ramakrishnan, G. et al., *Mol. Microbiol.*, 1996, 19:91–100; hereby incorporated by reference). Analysis of amebic RNA showed that all three 170 kDa subunit genes were expressed in the amebae and that the abundance of the hgl message dropped as the amebae entered a stationary growth phase.

Accordingly, the present invention provides both nucleic acid and immunological reagents specific for 170 kDa subunits encoded by each of the hgl1, hgl2 or hgl3 genes. Also included are reagents which detect regions common to all three hgl genes and the nucleic acid and protein products of these regions. For example, oligonucleotide probes specific for any one of these three genes are readily identified by one of ordinary skill in the art, using conventional nucleic acid probe design principles, by comparisons of the three DNA sequences which are disclosed in FIG. 1A as the hgl1 gene (SEQ ID NO: 1), in FIGS. 4A–4F as the hgl3gene (SEQ ID NO:4), and, in Tannich, E. et al., (supra) (the hgl2 gene). Example VI illustrates the use of oligonucleotide probes specific for each of the three hgl genes, for determining the level of RNA expression from each gene by Northern analysis. Other methods of using hgl-specific nucleic acids diagnostically, for pathogenic and/or non-pathogenic forms of *E. histolytica*, are described in U.S. Pat. No. 5,260,429.

Having now generally described the invention, the same will be more readily understood through reference to the following examples which are provided by way of illustration, and are not intended to be limiting of the present invention, unless specified.

EXAMPLE I

Construction of Expression Vectors

The 170 kDa subunit of the galactose lectin is encoded by at least five genes. The DNA used for all of the constructions described herein encodes the 170 kDa lectin designated hgl1 (FIG. 1A, sheets 1–6)). The nucleotide position designations refer to the numbering in FIG. 1A. The DNA sequence encoding hgl1 was expressed in three portions (see FIG. 2B):

(1) fragment C (nucleotides 46–1833 of SEQ ID NO: 1) included (a) the cysteine- and tryptophan-rich region, (b) the cysteine-free region, and (c) 277 amino acids of the cysteine-rich domain, (residues 2–596 of SEQ ID NO:3);

(2) fragment A (nucleotides 1492–3460 of SEQ ID NO:1) encoded the majority of the cysteine-rich domain, (residues 482–1138 of SEQ ID NO:3);

(3) fragment B (nucleotides 3461–3892 of SEQ ID NO:1) included 70 amino acids of the cysteine-rich domain, the putative membrane-spanning region, and the cytoplasmic tail (residues 1139–1276 of SEQ ID NO:3).

Figure 2B:
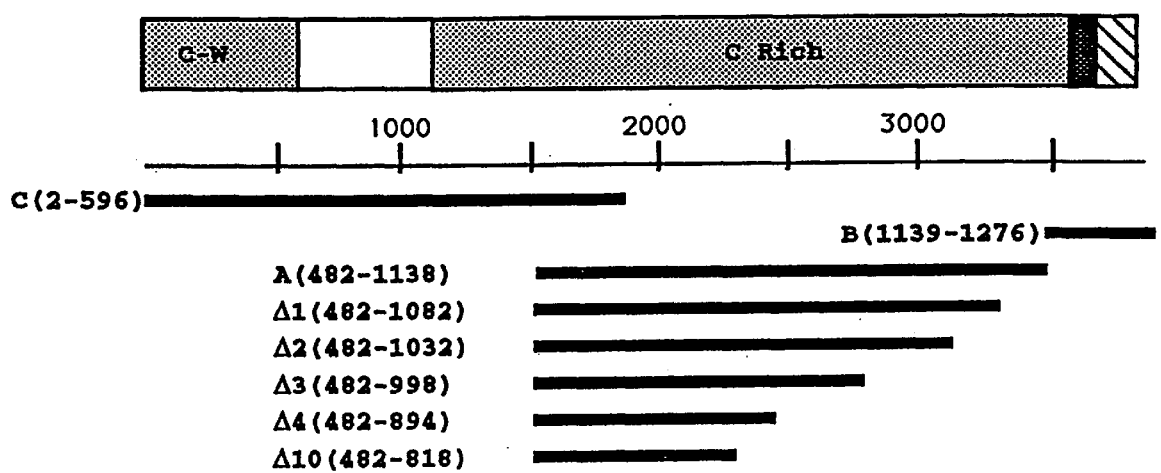

Each of these three fragments was inserted in-frame by ligation into pGEX2T or pGEX3X to obtain these proteins as GST fusions. A schematic diagram of the vectors is shown in FIG. 2.

Fragment C was produced by PCR amplification. Primers were designed so that a BamHI site was added to the 5' end and an EcoRI site was added to the 3' end during the PCR process. The PCR product, fragment C, was then digested with restriction enzymes BamHi and EcoRI, purified, and ligated into similarly digested pGEX3X. Fragments A and B were produced by digestion with EcoRI from plasmid clones (Mann, B J et al. *Proc Natl Acad Sci USA* (1991) supra) and ligated into pGEX2T that had been digested with EcoRI. In the pGEX expression system a recombinant protein is expressed as a fusion protein with glutathione S-transferase (GST) from *Schistosoma japonicum* and is under the control of the tac promoter. The tac promoter is inducible by IPTG. The construction of the vectors and subsequent expression is further described in Mann, B J et al. *Infec. Immun* (1993) supra.

Expression of all constructs in the correct reading frame was verified by sequencing and by Western immunoblot analysis using anti-adhesion antisera. Expression of the hgl1 fusion proteins was inducible by IPTG. The GST protein produced from the original pGEX2T (molecular mass of 27.5 kDa) did not react with the anti-adhesion sera.

EXAMPLE II

Production of Recombinant Protein

The four vectors described above, as well as the host vector were transfected into competent *E. coli* hosts. IPTG was used to induce expression of the genes encoding the fusion proteins. Production of the fusion proteins was determined by Western blot SDS-PAGE analysis of the lysates.

EXAMPLE III

Reactivity of Recombinant 170 kDa Subunit Fusion Proteins with mAbs

Figure 3:
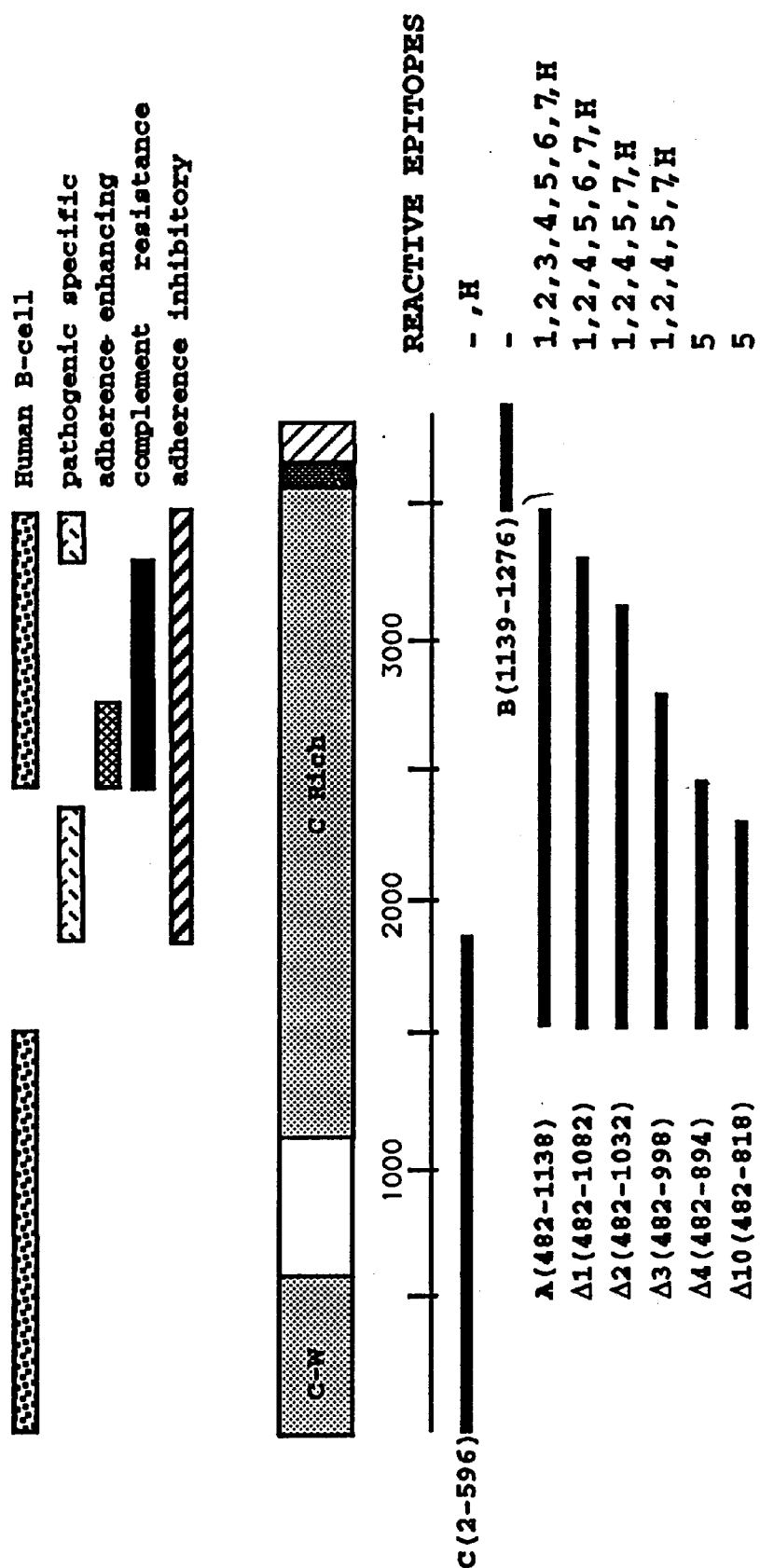
FIG. 3 is a diagram of the location of various epitopes on the 170 kDa subunit. In particular, the location of epitopes recognized by mAbs specific for the 170 kDa subunit are shown below the rectangular box which is the domain diagram. The epitopes were mapped by measuring reactivity of the mAbs with deletion constructs of the subunit. The domains of the 170 kDa subunit are labeled left to right as follows: "C-W" is the N-terminal region rich in cysteine and tryptophan; "CF" is the cysteine-free domain; "C-Rich" is the cysteine-rich domain; the transmembrane (TM) domain is shown as a dark box; CD is the cytosolic domain. (See: Mann, B. J. et al. *Parasit Today* (1991) 7:173–176). The amino acids included in the recombinant deletion variants of the subunit are shown in parentheses beside the deletion designation and are indicated by black bars below the domain diagram. The mAbs which recognized each deletion derivative are listed by number to the right of the horizontal bars (see also Table 1). Also shown above the domain diagram are maps of epitopes in terms of their reactivity human B cells, pathogen specificity and the effects of the antibodies on biological activity (adherence, complement resistance).

Induced cultures of bacterial strains expressing hgl1 fragment A, B, or C were harvested, lysed in sample buffer, and the lysate was applied to an SDS-polyacrylamide gel. After electrophoresis, the proteins were transferred to Immobilon and incubated with seven different anti-170-kDa mAbs, each specific for a different epitope. Characteristics of the individual mAbs are shown in Table 1. It will be noted that all the known epitopes are in the region of amino acids 596–1138 of SEQ ID NO:3).

Fusion proteins B and C failed to react with any of the seven mAbs. Fusion protein A, representing positions 482–1132, reacted with all seven mAbs but not with a negative control mAb, MOPC21. The mAbs were used at 10 μg/ml and polyclonal antisera at 1:1000 dilution. These results indicated that all seven epitopes were contained within the 542 amino acids of the cysteine-rich extracellular domain of the 170 kDa subunit.

TABLE 1

Characteristics of mAbs directed against the galactose adhesion 170 kDa subunit

| Epitope # | Designation | Isotype[1] | Adherence[1] | Cytotoxicity[2] | C5b9 Resistance[3] | P[4] | NP[4] | Location[5] |
|---|---|---|---|---|---|---|---|---|
| 1 | 3F4 | $IgG_1$ | Increases | Decreases | No effect | + | + | 895-998 |
| 2 | 8A3 | $IgG_1$ | Increases | No effect | Decreases | + | + | 895-998 |
| 3 | 7F4 | $IgG_{2b}$ | No effect | No effect | Decreases | + | – | 1082-1138 |
| 4 | 8C12 | $IgG_1$ | Inhibits | Inhibits | Decreases | + | – | 895-998 |
| 5 | 1G7 | $IgG_{2b}$ | Inhibits | Inhibits | Decreases | + | – | 596-818 |
| 6 | H85 | $IgG_{2b}$ | Inhibits[6] | Inhibits | Blocks | + | – | 1033-1082 |
| 7 | 3D12 | $IgG_1$ | No effect | Not tested | Blocks | + | | 895-998 |

[1]Adherence was assayed by the binding of Chinese hamster ovary (CHO) cells to *E. histolytica* trophozoites and by binding of $^{125}$I labeled purified colonic mucins to trophozoites. Petri, W. A. Jr. et al., J Immunol (1990) 144:4803–4809.
[2]The assay for cytotoxicity was CHO cell killing by *E. histolytica* trophozoites as measured by $^{51}$Cr release from labeled CHO cells. Saffer, L. D. et al. Infect Immun (1991) 59:4681–4683
[3]C5b9 resistance was assayed by the addition of purified complement components to *E. histolytica* trophozoites. The percent of amebic lysis was determined microscopically. Braga, L. L. et al. J Clin Invest (1992) 90:1131–1137.
[4]P and NP refer to reactivity of the mAb with pathogenic (P) and nonpathogenic (NP) species of *E. histolytica* as determined in an Elisa assay. Petri, W. A. Jr. et al., Infect Immun (1991) 58:1802–1806.
[5]Location of antibody binding site by amino acid number in SEQ ID NO:3.
[6]Inhibits adherence to CHO cells but not human colonic mucin glycoproteins. Petri et al., 1990, supra The generation of 3' deletions by controlled ExoIII digestion of fragment A of the 170 kDa subunit is outlined in FIG. 3. Deletion Δ1 contains amino acid residues 482–1082; Deletion Δ2 contains amino acid residues 482–1032; deletion Δ3 contains amino acid residues 482–998. The positions refer to SEQ ID NO:3 but may be replaced by corresponding stretches from SEQ ID NO:5 or from the gene products of hgl2, hgl4 or hgl5. The reactivities of the fusion proteins that include fragment A or either of two C-terminal deletions (Δ3 and Δ4) with the seven mAbs (Table 1) were determined. Deletion Δ3 reacted with mAbs against epitopes 1, 2, 4, 5 and 7 but failed to react with mAbs recognizing epitopes 3 and 6; Deletion Δ4 (residues 498–894) reacted only with the mAb specific for epitope 5.

The five deletion derivatives of fusion protein A shown in FIG. 3, ranging in estimated size from 35 to 68 kDa, were tested for reactivity with each mAb as is summary in FIG. 3. The endpoints of the various deletions were determined by DNA sequencing with primers specific for the remaining hgl1 sequence. mAbs recognizing epitopes 1 and 2, which increase amebic adherence to target cells (“enhancing antibodies"), failed to react with recombinant fusion proteins lacking amino acids 895 to 998. Similarly, mAbs recognizing epitope 4, an inhibitory epitope, and epitope 7, which has the effect of abrogating amebic lysis by complement, failed to react with deletion mutants lacking 895–998. The mAb specific for epitope 6, which has inhibitory effects on amebic adherence and abrogates lysis of amebae by complement, did not react with a recombinant protein missing amino acids 1033 to 1082. Recombinant proteins lacking amino acids 1082 to 1138 did not react with the mAb specific for the neutral epitope 3. Finally, a construct containing amino acids 482 to 818 was recognized only by the mAb to epitope 5 (an adherence-inhibitory epitope). The predicted locations of the epitopes recognized by the 7 mAbs are listed in the right-most column of Table 1 above and are shown in FIG. 3.

EXAMPLE IV

Reactivity of 170 kDa Fusion Proteins with Human Immune Sera

Since the galactose adhesin is a major target of the humoral immune response in the majority of immune individuals, the mapping of human B-cell epitopes of the 170 kDa subunit was undertaken. The recombinant fusion proteins and ExoIII-generated deletion constructs were tested for reactivity with pooled human immune sera in the same manner as described above for mAb reactivity. Non-immune sera was used as a control. Fusion proteins A and C reacted with immune sera, whereas fusion protein B did not. Human immune sera also reacted with deletion constructs Δ1, Δ2, and Δ3 but not with Δ4 or Δ10. Reactivity of immune sera with the different deletions localized major human B-cell epitopes to two primary sites: (a) within the first 482 amino acids and (b) between amino acids 895 and 1138 (FIG. 3). This second region is the site of six of the mAb epitopes. These results are consistent with a report by Zhang et al., supra, who found that sera from immune individuals reacted primarily with recombinant adhesion constructs containing amino acids 1 to 373 and 649 to 1202.

Thus, for assays to detect human antibodies against *E. histolytica*, the useful epitope-bearing portions are those shown in Table 2.

TABLE 2

| Positions | Epitope # | P/NP |
|---|---|---|
| 2–482 | ? | ? |
| 1082–1138 | 3 | P |
| 1033–1082 | 6 | P |
| 895–998 | 1,2,4,7 | both |

The epitope-bearing fragments indicated can be used alone as fragments or as parts of a chimeric or a fusion protein, or any combination of the above peptide fragments can be used.

EXAMPLE V

Immunization Using Recombinant Subunit Protein

A GST fusion protein with fragment A was prepared in *E. coli* as described in Example I. This peptide contains an upstream GST-derived peptide sequence followed by, and fused to, amino acids 432–1138 encoded by nucleotides 1492–3460 of SEQ ID NO: 1. The protein was produced intracellularly. The cells were harvested and lysed and the lysates subjected to standard purification techniques to obtain the purified fusion protein.

Gerbils were immunized by an intraperitoneal injection of 30 μg of purified fusion protein in complete Freund's adjuvant and then boosted at 2–4 weeks with 30 μg of the fusion protein in incomplete Freund's adjuvant. The gerbils were challenged at 6 weeks by intrahepatic injection of $5 \times 10^5$ amebic trophozoites and were sacrificed 8 weeks later. The presence and size of amebic liver abscesses was determined.

The results of these two experiments are shown in Table 3, below. In experiment 1, six animals were used as controls and nine were administered the fusion protein; in experiment 2, seven animals were used as controls and seven were immunized with the fusion protein. The administration of the fusion protein resulted in a statistically significant reduction in the size of abscesses.

TABLE 3

| | Experiment 1 | | | Experiment 2 | | |
|---|---|---|---|---|---|---|
| | n | Abscess Weight | % with Abscess | n | Abscess Weight | % with Abscess |
| Control | 6 | 1.44 ± 1.64 | 71 | 7 | 4.76 ± 1.78 | 100 |
| GST-(482–1138) | 9 | 0.81 ± 0.10* | 100 | 7 | 2.35 ± 1.99 | 100 |

•*p < 0.03 compared to control.

EXAMPLE VI

Analysis of the Gene Family Encoding the 170 kDa Subunit of *E. histolytica* Gal/GalNAc Adherence Lectin This Example shows that the adhesin 170 kDa subunit of *E. histolytica* HM-1 :IMSS strain is encoded by a gene family that includes hgl1, hgl2 and a previously undescribed third gene, herein designated hgl3. Since hgl1 and hgl2 were originally sequenced, in part, from different cDNA libraries, it was possible that they represented strain differences of a single gene. However, in this report both 5' and 3' termini of hgl1, hgl2, and hgl3 were isolated and sequenced from the same lambda genomic library demonstrating unambiguously that hgl is a gene family.

Comparison of the amino acid sequences of the three 170 kDa subunit genes showed that the products of hgl1 and hgl2 are 89.2% identical, hgl1 and hgl3 are 95.2% identical, and hgl2 and hgl3 are 89.4% identical. Sequence variation within the gene family, however, appears to be nonrandomly distributed within the coding sequence. The majority of the nonconservative amino acid substitutions as well as insertions and deletions occur in the C-terminal one-third of the molecule. Comparison of the amino acid sequences of the products of hgl2 and hgl3 revealed that 11 of the 19 nonconservative amino acid substitutions and 11 of the 13 residues inserted or deleted reside within the N-terminal 400 residues. A similar pattern of variation is present when hgl1- and hgl2-encoded proteins are compared. While the proteins of hgl1 and hgl3 contain only two nonconservative substitutions, both are found within the first 400 residues although the 57 conservative substitutions appear to be more randomly distributed throughout the coding sequence. The high degree of sequence conservation between hgl3 and hgl1 suggest that they may have arisen from a recent gene duplication event.

All 97 cysteine residues were conserved in the three genes. The hgl2 gene was originally reported to lack a single cysteine codon present in both hgl1 and hgl3. However, this discrepancy has since been recognized as a sequencing error (Dr. E. Tannich, Bernhard Nocht Institute, Hamburg, Germany). The cysteine residues are nonrandomly distributed throughout the protein (FIG. 4) with the highest concentration in the cysteine-rich domain between residues 379–1210. All seven mAb-identified epitopes map to this region (Mann, B. J. et al. *Infect Immun* (1993) 61:1772–1778). As these mAbs can block target cell adhesion, target cell lysis (Saffer, L. D. et al. *Infect Immun* (1991) 59:4681–4683), and/or resistance to host complement-mediated lysis (Braga, L. L. et al. *J Clin Invest* (1992) 90:1131–1137), the conservation of cysteine residues may play an important role in maintaining the conformation of this important region of hgl.

The Northern hybridization results indicated that all three genes were expressed in the amebae. As the messages of hgl1–3 are predicted to comigrate at 4.0 kb, differential hybridization was required to ascertain expression of individual genes. Due to the high degree of sequence similarity between hgl1–3, relatively short oligonucleotides (17–21 bases) specific for regions where the three genes diverge were synthesized. Each probe was compared by computer analysis to the other hgl genes to be certain that they were sufficiently divergent to prevent cross hybridization. Hybridization and wash conditions were highly stringent for such A/T rich probes and were done at temperatures 50° C. or less below the predicted Tm based upon nearest neighbor analysis. These precautions make unlikely the possibility of cross hybridization with other hgl gene members.

The Northern blots also indicated that mRNA from all three genes fell in abundance as the amebae progressed from logarithmic to stationary growth. This finding correlates with the observation that late logarithmic and stationary-phase amebae have decreased ability to adhere to, lyse, and phagocytose target cells (Orozco, E. et al. (1988) In: *Amebiasis: Human infection by Entamoeba histolytica* (Ravdin J. I., ed), pp. 326–338. John Wiley & Sons, Inc., New York.

Details of the experimental methods and results of the characterization of the hgl multigene family are presented below.

Library Screen. A lambda Zap® II library containing randomly sheared 4–5 kb fragments of genomic DNA from HM-1:IMSS strain *E. histolytica* was provided by Dr. J. Samuelson at Harvard University (Kumar, A. et al. *Proc Natl Acad Sci USA* (1992) 89:10188–10192). Over 80,000 plaques from the library were screened on a lawn of XL-1 Blue *E. histolytica* (Stratagene, La Jolla, Calif.). Duplicate plaque lifts, using Hybond-N membranes (Amersham, Arlington Heights, Ill.), were placed in a prehybridization solution consisting of 6× SSC (0.89 M sodium chloride and 90 mM sodium citrate), 5× Denhardt's solution, 0.5% SDS, 50 mM NaPO$_4$ (pH 6.7), and 100 μg/ml salmon sperm DNA for a minimum of 4 hours at 55° C. A 5'- and 3'-DNA fragment of hgl1 (nucleotides 106–1946 and 3522–3940 respectively) were labeled with [$^{32}$P]dCTP (Amersham) using the Random Primed® DNA labeling kit according to the manufacturer's instructions (Boehringer Mannheim, Mannheim, Germany) and were hybridized separately to the membranes overnight at 55° C. in prehybridization solution. Membranes were rinsed once and washed once for 15 minutes at room temperature in 2× SSC, 0.1% SDS, then washed once for 15 minutes at room temperature, and twice at 55° C. for 20 minutes in 0.1× SSC, 0.1% SDS. Plaques that hybridized with the 5'- or the 3'-radiolabeled probe on both duplicate filters were isolated and purified.

Northern blots and hybridization. Total RNA was harvested from amebae using the guanidinium isothiocyanate method (RNagen®, Promega, Madison, Wis.). Polyadenylated RNA was purified from total RNA using PolyATract System 1000® (Promega). RNA was electrophoresed through a formaldehyde gel and transferred to a nylon Zetabind® membrane (Cuno) using 25 mM phosphate buffer (pH 7.5) as described (Sambrook, J. et al. (1989) *Molecular Cloning: A Laboratory Manual*, Cold Spring Harbor Laboratory Press, Cold Spring Harbor, N.Y.). The membrane was incubated in prehybridization solution and incubated at 37° C. for at least two hours. Oligonucleotides (18–22 nucleotides long) were end-labeled using polynucleotide kinase and [γ-$^{32}$P]ATP (Sambrook, J. et al., supra), were added to the hybridization mixture and the membrane, and were incubated at 37° C. overnight. The membrane was then washed once at room temperature for 10 minutes, once at 37° C. for 10 minutes; and twice at 40–44° C. for 15 minutes each in 2× SSC, 0.1% SDS. The following radiolabeled probes were used (Plaimauer, B. et al. *DNA Cell Biol* (1993) 12:89–96):

| | | |
|---|---|---|
| 5'-TTTGTCACTATTTTCTAC-3' | hgl1 | (SEQ ID NO:7); |
| 5'-TATCTCCATTTGGTTGA-3' | hgl2 | (SEQ ID NO:8); |
| 5'-TTTGTCACTATTTTCTAC-3' | hgl3 | (SEQ ID NO:9); and |
| 5'-CCCAAGCATATTTGAATG-3' | EF-1I | (SEQ ID NO:10). |

Characterization of the hgl3 gene. The hgl3 open reading frame was 3876 bases (SEQ ID NO:4) with a predicted translation product of 1292 amino acids (SEQ ID NO:5) as shown in FIGS. 4A–4F. The predicted translation products of hgl1 and hgl2 are 1291 and 1285 amino acids long, respectively. A putative signal sequence and a transmembrane domain were identified in the amino acid sequence of hgl3 similar to hgl1 and hgl2. The N-terminal amino acid sequence of the mature hgl3 protein, determined by Edman degradation (Mann, B. J. et al. *Proc Natl Acad Sci USA* (1991)88:3248–3252), was assigned residue number 1. Previous analysis of hgl1 and hgl2 identified a large, conserved, extracellular region which was 11% cysteine, designated the "cysteine-rich domain" (Mann, B. J. et al. *Parasit Today* (1991) 7:173–176) (See FIGS. 3 an 6). Sequence analysis of hgl3 revealed that all 97 cysteine residues present within this region were also conserved in both of the previously reported 170 kDa subunit genes.

Figure 6:
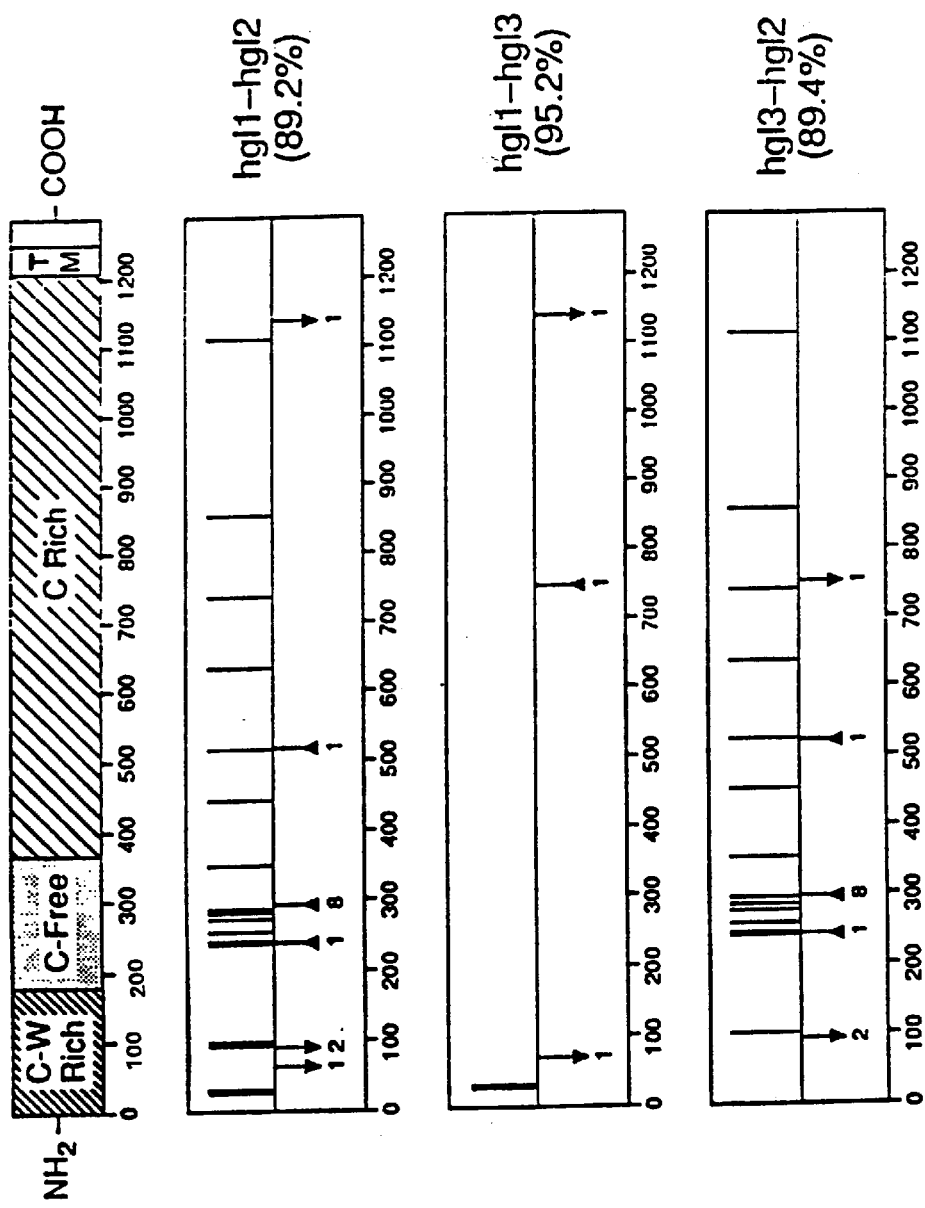
FIG. 6 is a schematic representation of the protein product of the 170 kDa subunit gene (top panel) and a pairwise comparison of the amino acid sequences of the products of three known members of this gene family, hgl1, hgl2 and hgl3. The protein structure is as in FIG. 3, above. Amino acid sequence comparisons of the protein products of hgl1, hgl2 and hgl3 are shown in the lower three panels. Upright lines indicate nonconservative amino acid substitutions in the second protein of the comparison (listed at right). Downward arrows indicate a deletion while downward lines ending in upward-pointing arrowheads indicate insertions. The number of inserted or deleted residues are given below the arrowheads. The % amino acid sequence identity is indicated at right.

A schematic comparison (FIG. 6) of 170 kDa subunit gene sequences at the protein level revealed a high degree of sequence identity. However, seven sites, ranging from 3–24 nucleotides, were identified as resulting from an insertion or deletion, and which maintained the same open reading frame, in one subunit relative to another. Both hgl1 and hgl3 contained a large number of nonconservative amino acid substitutions when compared to hgl2, making them 89.2% and 89.4% identical to hgl2 respectively. The comparison of hgl1 and hgl3 revealed two nonconservative substitutions, 57 conservative amino acid substitutions and 3 single residue insertion/deletions, making them 95.2% identical.

All 16 potential sites of glycosylation present in hgl1 were conserved in hgl3. A sequence analysis of hgl2 indicated that it shared only 9 of these sites. Glycosylation appears to account for approximately 6% of the apparent molecular mass of the 170 kDa subunit Mann, B. J. et al. *Proc Natl Acad Sci USA* (1991) 88:3248–3252).

All three 170 kDa subunits are expressed. Since hgl3 was isolated from a genomic library, it was unknown if this gene was transcribed. Polyadenylated RNA was harvested from amebae in both log and stationary phase growth. Probes specific for hgl1, hgl2, or hgl3 were hybridized to a Northern blot and identified an RNA band of the predicted size of 4.0 kb.

As the mRNAs of hgl1, hgl2 and hgl3 were predicted to comigrate at 4.0 kb, differential hybridization was required to ascertain expression of individual genes by Northern analysis. Due to the high degree of identity between the three hgl1 genes, relatively short oligonucleotides (17–21 bases) were synthesized specific for regions where the three genes diverge. Each probe was compared by computer analysis to the other hgl genes to be certain that it was sufficiently divergent to prevent cross hybridization. Hybridization and washing conditions were highly stringent for such A/T rich probes, and hybridization was done at temperatures $\leq 5°$ C. below the predicted Tm based upon nearest neighbor analysis. While it is impossible to rule out cross hybridization with other hgl gene family members, these precautions significantly lowered the likelihood of such an event.

The abundance of message decreased significantly as the amebic trophozoites passed from logarithmic phase growth (lane A) to stationary growth (lane B) while expression of the control gene, EF-II, remained constant or increased slightly. This finding correlates with results indicating that late logarithmic and stationary phase amebae have a decreased ability to adhere to, lyse and phagocytose target cells (Orozco et al., supra).

Estimation of the number of 170 kDa subunit genes. The observations herein confirm that the adhesin 170 kDa subunit of HM-1 :IMSS strain E. histolytica is encoded by a gene family that includes hgl1, hgl2 and a previously undescribed third gene which is designated hgl3. Since hgl1 and hgl2 were originally sequenced, in part, from different cDNA libraries, it was possible that they represented polymorphs of a single gene. However, in the present work both 5' and 3' termini of hgl1, hgl2, and hgl3 were isolated and sequenced from the same lambda genomic library, demonstrating unambiguously that hgl is a gene family.

As stated above, Southern blot analyses and library screening data best support the conclusion of a gene family of three members. For Southern blots, two restriction enzymes, DdeI and HindIII, cut genomic DNA to completion and yielded analyzable restriction fragments. As the membrane was hybridized with a fragment of hgl1 corresponding to nucleotides 1556 to 3522, two bands of >976 and 1965 nucleotides should have been present from hgl3. This central hgl1 radioprobe would hybridize with three bands of 1158, 810 and >1080 nucleotides from hgl1 (SEQ ID NO: 1) and would hybridize with five bands of 819, 312, 55, 755, and >1080 nucleotides from hgl2. The Southern blot showed 7 bands for genomic DNA digested with DdeI, at sizes of 4200, 3700, 2100, 1800, 1300, 840, and 760 nucleotides. As the 819 and 810 nucleotide bands would be expected to comigrate, all the bands observed with DdeI digestion are explained by the restriction maps of hgl1–3.

Because no HindIII restriction sites are within the coding region in hgl1, hgl2 and hgl3, each gene should be represented by a single band greater than 4.0 kb. The Southern blot showed three bands of 17500, 5600, and 4200 nucleotides. Should an additional 170 kDa subunit gene exist, its DdeI and HindIII fragments would need to comigrate with hgl1, hgl2 and hgl3 bands, and be so divergent that they would fail to hybridize with the hgl1 probe under very low stringency, or be too large to be resolved and transferred.

The genomic library was screened separately with a 5' and a 3' hgl specific probe, such that additional 170 kDa subunit genes would be isolated even if they contained only partial identity with the gene family at only one end or even if one termini of an additional gene had been lost during library amplification. The library screen looked at more than 3.2× $10^8$ bases of genomic DNA in an organism with an estimated genome size of $10^{7.5}$ bases (Gelderman, A. H. et al. *J Parasitol* (1971) 57:906–911). Thus, a full genomic equivalent was screened at low stringency for genes containing identity at either end. Of seven clones identified with the 5' 170 kDa subunit-specific probe, four contained inserts that matched the reported sequence for hgl1, two matched the sequence of hgl2, and one clone represented hgl3. Of eight clones obtained using the 3' radiolabeled fragment, one matched the sequence for hgl1, five matched the sequence of hgl2, and two represented hgl3. These studies did not reveal any termini that did not match the sequence of hgl1, hgl2 or hgl3.

EXAMPLE VII

Oral Immunization with Salmonella Expressing the Gal/GalNAc Inhibitable Lectin of *E. histolytica*

An effective vaccine must be able to protect against both mucosal and systemic disease. In this study, an attenuated Salmonella strain that expressed a portion of the *E. histolytica* Gal/GalNAc lectin 170 kDa subunit was used to orally immunize gerbils. Animals were challenged by intrahepatic injection of amebic trophozoites. A significant decrease in size of amebic liver abscesses was observed in orally immunized animals. Oral immunization with a Salmonella-based vaccine was as effective as systemic immunization for protection against systemic challenge.

MATERIALS AND METHODS

Bacterial Strains, Plasmids, and Media

*Salmonella dublin* live vaccine strain SL5928 aroA148 fliC(i)::Tn10 and *S. typhimurium* LB5000 hsdSB121 leu-3121, were donated by B. Stocker, Stanford University (Newton S. M. et al., *Science* 1989, 244: 70. The host strain for pGEX vectors (Pharmacia Biotech, Uppsala, Sweden) was *Escherichia coli* MC1061. JM109 was the host strain used to express proteins generated from pRSET vectors (Invitrogen, San Diego, Calif.). All bacterial strains were grown in Luria Broth (LB). The concentration of antibiotic, when added, was 50 µg/ml for ampicillin, or 40 µg/ml for spectinomycin. Plasmid pADE171, which encodes spectinomycin resistance (Hone D. et al., *Microbial. Path.* 1988, 5, 407 kindly supplied by Eric Elsinghorst, Naval Medical Research Institute.

Expression and Purification of Recombinant Proteins

Recombinant lectin proteins encoded by pGEX plasmids were induced and expressed according to the procedure described by D. B. Smith and K. S. Johnson (*Gene* 1988, 67, 31). Induction and expression recombinant proteins encoded by pRSET plasmids was carried out according to manufacturers instructions.

Recombinant proteins from induced bacterial cultures were separated by electrophoresis on 10% SDS polyacrylamide gel electrophoresis (PAGE) overnight at 40° C. Gels were briefly stained with 0.5% Coomassie Blue in acetic acid:isopropanol:water (1:3:6) and the recombinant protein band excised. The protein was eluted and concentrated from the gel using an Amicon centrilutor (Beverly, Mass.). Protein concentration was determined using BCA Protein Assay system (Pierce, Rockford, Ill.). The eluted protein was incubated with anti-lectin antibodies on immunoblots to confirm identity.

Immunoblotting

Proteins, separated by electrophoresis on 10% SDS-PAGE, were electrophoretically transferred to a PVDF Immobilon-P® membrane (Millipore Corp., Bedford, Mass.) at 40° C. for 2 h at 0.5 mA in 20% methanol-25 mM Tris base-192 mM glycine. After transfer, the membranes were blocked in 3% bovine serum albumin in blot wash buffer (BWB) (50 mM Tris base, 200 mM NaCl, 0.1% Tween 20) at 40° C. overnight. Membranes were incubated with pooled protein A-purified gerbil sera (50 µg/ml) or rabbit anti-lectin polyclonal antibody for 1 h at room temperature, washed, then incubated with protein A conjugated with horse radish peroxidase (HRP) for 1 h at room temperature. Bound protein A-HRP was visualized using chemiluminescent detection as recommended by the manufacturer (LumiGLO®, Kirkegaard & Perry Laboratories, Inc, Gaithersburg, Md.).

Construction of a Salmonella Strain Expressing Fragment A

A pADE171-based plasmid encoding fragment A, pADE-A, was constructed as follows: A DNA fragment containing the ptac promoter and fragment A of the hgl1 gene was first amplified by PCR using pGEX-A as a template (Mann B. J. et al., *Infec. Immun.,* 1993, supra). The sequence of the two primers used corresponded to pGEX2T sequences located upstream of the ptac promoter or downstream of the 3' end of fragment A, and included extra sequences that specified a Pst 1 site. The sequence of the sense primer was

```
5'-GGCGGCTGCAGAACGCAATTAATGTGAGT-3'  (SEQ ID NO:11)
``` and the sequence of the anti-sense primer was

```
5'-GGCGGCTGCAGCTTACAGACAAGCTGTGA-3'  (SEQ ID NO:12).
```

PCR was performed using the conditions recommended by the manufacturer Perkin Elmer Cetus, Norwalk Conn.) and incubated for 30 cycles at 94° C. for 1 min, 48° C. for 1 min, 72° C. for 3 min. The reaction was preceded by a 5 min incubation at 94° C. and terminated with an incubation at 72° C. for 15 min. The PCR fragment was digested with Pst1 and ligated to Pst-digested pADE171. The recombinant plasmid was first selected in *E. coli* strain MC1061. The purified plasmid was then introduced into *S. typhimurium* strain LB5000 so that the plasmid DNA would be properly modified for introduction into Salmonella strains. Plasmid DNA isolated from LB5000 was introduced into *S. dublin* strain SL5928 by electroporation. Expression of the lectin fragment encoded by pADE-A in SL5928 was verified by Western blots of bacterial lysates and anti-170 kDa lectin subunit antibody.

Immunization and Challenge Protocol

For i.p. immunizations animals were injected with 30 μg of electro-eluted fragments of the 170 kDa subunit or glutathione S-transferase (GST) in complete Freund's adjuvant. Four weeks later animals received booster immunizations with 30 μg of antigen in incomplete Freund's.

For oral immunization animals were fed $10^8$–$10^{10}$ bacteria on days 1, 5 and 7 by oral gavage. Six weeks after the first immunization the animals were challenged by direct intrahepatic injection with $5\times10^5$ amebic trophozoites (Chadee, K. et al., *Am. J. Pathol.,* 1984, 117:71; Chadee, K., et al., *Am. J. Trop. Med. Hyg.,* 1985, 34:283. Fourteen days post-challenge the gerbils were sacrificed and any liver abscess was dissected away from the remaining liver tissue and weighed. Each abscess was cultured for *E. histolytica* in TYI medium[25]. Results were analyzed using Student's t test.

RESULTS

Intraperitoneal Immunization with Purified 170 kDa Polypeptides

To test the ability of different regions of the 170 kDa subunit to elicit protection against amebic liver abscess formation portions of the 170 kDa subunit, fragment A (containing amino acids 482–1138 of the cysteine-rich region) and fragment C (amino acid s 2–596) were expressed in *E. coli* and purified as described herein. Gerbils were immunized by i.p. injection with the purified recombinant lectin polypeptides, then challenged by intrahepatic injection of amebic trophozoites and analyzed for the presence and size of an amebic liver abscess 14 days later. The results of three independent trials are presented in Table 4, below.

In Experiment 3, animals were immunized with a polyhistidine fusion version of fragment A that was encoded by an pRSET vector containing fragment A. In Experiment 2, animals were immunized with a combination of fragments A and C; however there was no significant additional decrease in liver abscess size compared to animals immunized with fragment A alone. Since the addition of fragment C did not enhance protection, further studies with Salmonella expression were confined to fragment A.

TABLE 4

Vaccine Trials: I.P. Immunization with Purified Lectin Peptides

| Immunogen | Abscess Weight (g)[a] | n | % animals with abscesses | p value[b] |
|---|---|---|---|---|
| Experiment 1 | | | | |
| Control (GST) | 4.76 ± 4.71 | 7 | 100 | |
| Fragment A | 2.35 ± 1.99 | 7 | 100 | 0.11 |
| Experiment 2 | | | | |
| Control (GST) | 1.44 ± 1.64 | 7 | 71 | |
| Fragment A | 0.18 ± 0.10 | 9 | 100 | 0.030 |
| Fragment A/C | 0.29 ± 0.29 | 9 | 100 | 0.048 |
| Experiment 3 | | | | |
| Control | 1.92 ± 2.82 | 10 | 100 | |
| Fragment His-A | 0.029 ± 0.83 | 9 | 55 | 0.062 |
| Total | | | | |
| Control | 2.73 ± 3.47 | 24 | 95.6 | |
| Fragment | 0.78 ± 1.44 | 25 | 80 | 0.011 |

[a]Mean ± Standard Deviation
[b]P values were calculated to the difference in liver abscess size of lectin-immunized vs. control animals

Construction of Salmonella Expressing the Gal/GalNAc Lectin

The first step in testing the effectiveness of an oral anti-amebic Salmonella vaccine was to create a stable recombinant strain expressing fragment A of the 170 kDa subunit. Initially a pGEX plasmid containing DNA encoding fragment A was introduced into Salmonella strains, however the stability of this plasmid was very low. To try to improve stability of expression, the DNA encoding fragment A was inserted into plasmid vector pADE171 (Hone et al., supra), creating pADE-A. This plasmid was introduced into *S. dublin* strain SL5928 creating strain SL5928-A. The expression of fragment A in SL5928-A was verified by Western blots of bacterial lysates using anti-170 kDa subunit antibody. A strain carrying the parent plasmid, pADE171, was also created and designated SL5928–171.

To test the stability of the fragment A expression in SL5928-A in vitro, an overnight culture grown in the presence of antibiotic was diluted 1:500 in LB without antibiotic and grown for an additional 24 hours. This dilution procedure was repeated for 5 consecutive days using the previous day's culture. The percentage of spectinomycin-resistant bacteria was determined by plating the bacteria on LB and LB plus spectinomycin plates each day. The percentage of spectinomycin resistant bacteria dropped to 60% on day two and by day six it had dropped to 23%. Fragment A protein was detectable by immunoblotting in cultures grown up to four days without antibiotic.

In vivo stability of the expression of fragment A in 5928-A was tested by examining the bacteria isolated from the livers and spleens of gerbils that had been fed bacteria. Gerbils were fed $10^{10}$ bacteria on days 1 and 5. On day 8, the gerbils were sacrificed and the spleens and livers harvested. The organs were homogenized in LB and spun at low speed to pellet cellular debris. The supernatants were plated on LB plus spectinomycin. Six out of six spectinomycin resistant bacteria tested expressed fragment A as measured on Westerns blots of total bacterial protein. The estimated titer of spectinomycin resistant bacteria isolated from the livers and spleens of immunized animals in this experiment was $3\times10^2$/ml.

Oral Immunization with Recombinant Salmonella Expressing the A Fragment

The ability of recombinant Salmonella expressing fragment A of the 170 kDa subunit to protection against amebic liver abscess formation by oral immunization was examined. Gerbils were immunized by oral gavage with the various strains of attenuated Salmonella. Animals were given 3 doses of bacteria on days 1, 5 and 7. Six weeks after the final dose animals were challenged with amebic trophozoites by intrahepatic injection and sacrificed 2 weeks later. In two independent experiments animals orally immunized with Salmonella expressing fragment A had a decrease in the size of liver abscess compared to animals immunized with the bacteria carrying the plasmid vector (Table 5).

Presence of Antibody in Immunized Animals

To determine if the oral immunization protocols used above induced anti-GalNAc lectin antibodies, serum samples were collected both before and after intrahepatic challenge with amebic trophozoites. Pooled protein A purified antisera from Experiment 5 were incubated with purified denatured Gal/GalNAc lectin immobilized to a PVDF membrane. Bound antibody was visualized with protein A labeled with horseradish peroxidase and a chemiluminescent substrate. No anti-lectin antibody could be detected in pre-challenge sera from animals orally immunized with SL5928-A. In addition no anti-lectin antibody could be detected in pre-challenge sera from SL5928-A immunized animals by ELISA. Anti-lectin antibody reactivity was observed in post-challenge sera from both SL5928–171 and SL5928-A immunized animals. It should be noted that pre-challenge sera from SL5928-A immunized animals did recognize total Salmonella proteins on Western blots whereas pre-immune gerbil sera did not.

TABLE 5

Vaccine Trials: Oral immunization with attenuated Salmonella expressing fragment A

| Immunogen | Abscess Weight (g)[a] | n | % animals with abscesses | p value[b] |
|---|---|---|---|---|
| Experiment 4 | | | | |
| 5928-171 | 0.56 ± 0.32 | 5 | 80 | |
| 5928-A | 0.086 ± 0.132 | 5 | 60 | 0.016 |
| Experiment 5 | | | | |
| 5928-171 | 0.50 ± 0.62 | 8 | 87.5 | |
| 5928-A | 0.045 ± 0.088 | 8 | 62.5 | 0.059 |
| TOTAL | | | | |
| 5928-171 | 0.52 ± 0.51 | 13 | 84.6 | |
| 5928-A | 0.061 ± 0.10 | 13 | 69.3 | 0.059 |

[a]Mean ± Standard Deviation
[b]P values were calculated to compare the differences in liver abscess size of animals fed lectin-expressing bacteria vs. those fed control bacteria

DISCUSSION

This study demonstrated that oral administration of attenuated Salmonella, expressing a portion of the GalNAc lectin, can provide protection against amebic liver abscess formation in the gerbil model of amebiasis. A *S. dublin* strain of bacteria was created that expressed a portion of the cysteine-rich region of the Gal/GalNAc lectin, designated fragment A. Protection against amebic liver abscess formation was observed in animals that had been orally immunized with fragment A-expressing bacteria. An oral vaccine for amebiasis has the potential to be more effective than a systemic vaccine since the primary site of protection against infection with *E. histolytica* is at the intestinal mucosal surface. Even though the mucosal immune response was not measured in this study, vaccination via the mucosal route was effective in preventing systemic disease.

Previous vaccine trials demonstrated that systemic immunization with this lectin conferred protection in the gerbil model of amebiasis. Petri and Ravdin first identified the Gal/GalNAc lectin as a protective antigen by i.p. immunization with native heterodimeric protein that had been purified using monoclonal antibody affinity chromatography (Petri W. A. Jr. and Ravdin J. I., *Infect. Immun.* 1991, 59:97). Protection was observed in 67% of immunized animals. Zhang et al., *Infect. Immun.* 1994, 62:2605, reported that i.p. immunization with a portion of the cysteine-rich region of the 170 kDa subunit conferred protection against liver abscess formation in gerbils with a vaccine efficacy of 81%. In a similar study Soong et al. (*J. Inf. Dis.* 1995, 171:645) observed a significant number of gerbils protected against liver abscess formation with i.p. immunization with the cysteine-rich region. Their vaccine efficacy was 71% but there were no significant difference in abscess size in immunized unprotected animals when compared to controls. The cysteine-rich region used by Zhang et al. corresponds to amino acids 649–1201. Soong et al. used amino acids 767–1138, while amino acids 483–1138 of the cysteine-rich region were used in the present example. The lack of complete protection observed in these experiments and the inability to detect antibody may be due to the low level of infectivity of the bacteria in the spleen and liver and/or instability of the plasmid. The plasmid appeared to be somewhat unstable in culture and the number of spectinomycin resistant bacteria recovered from the liver and spleen was low. However, all of the spectinomycin resistant bacteria isolated from the spleen and liver that were tested still expressed fragment A, indicating that the plasmid was not substantially rearranged.

The cysteine-rich region of the 170 kDa subunit has been shown to be the immunologically reactive portion of the protein. Six different mAbs that recognize functionally distinct epitopes located within a portion of the cysteine-rich region containing amino acids 597–1138 were shown to neutralize t he virulence traits of adherence, contact-dependent cytolysis, and amebic resistance to lysis by complement components C5b-9 (see above and Mann B. J. et al., 1993, supra. This region has also been implicated in stimulating cell mediated immune responses. The lectin has been shown to stimulate TNF-α in naive macrophages and to stimulate nitric oxide production and amebicidal activity by activated macrophages in vitro (Seguin R. et al., *Proc. Natl. Acad. Sci. USA* 1996, 92:12175). This stimulatory activity was blocked by some of the mAbs that recognize amino acids 597–1138 of the cysteine-rich region. The cysteine-rich region and peptides derived from this region have also been shown to cause proliferation of lymphocytes from patients recovered from amebic disease (C. Velasquez et al., *J. Euk. Microbiol.*, 1995, 42:636).

Anti-lectin antibodies were not detected by Western blots of reduced lectin in pre-challenge immune sera from gerbils orally immunized with Salmonella expressing fragment A. The lack of an antibody response to antigens introduced by oral immunization with recombinant strains of Salmonella has been observed for several other antigens (Sadoff, J. C. et al., *Science,* 1988, 240:336; Fouts, R. R. et al., *Vaccine,* 1995, 17:1697. These results suggest that a humoral response was not primarily responsible for protection in this model system. Previous vaccine trials have found no correlation between pre-challenge antibody titer and protection (Petri & Ravdin, supra; Soong et al., supra). However the inability to detect anti-lectin antibody could have been due to the protein A purification of the gerbil sera. Protein A purification was found to be necessary in order to reduce the background and visualize a specific signal. Protein A preferentially binds to specific antibody isotypes and isotype binding can also vary depending upon the animal species. If the response was primarily of antibody isotype that did not bind well to protein A these antibodies would have been lost during purification and therefore go undetected. Improved methods for detecting gerbil antibodies should alleviate this problem. The nature of the protective immune response in the gerbil model still requires further resolution.

The foregoing study therefore demonstrated that oral immunization with Salmonella expressing an immunogenic fragment of the Gal/GalNAc lectin of *E. histolytica* may be the basis of a protective vaccine strategy.

EXAMPLE VIII

Identification of an Adherence and Cytotoxicity Inhibitory Epitope of the *E. histolytica* Adhesin that Bears the Sugar Binding Specificity In order to identify a region of the lectin which binds only adherence inhibitory antibodies, the present inventors expressed a 312 bp region of the 170 kDa subunit DNA encoding amino acids 896–998 as a recombinant GST fusion protein in *E. coli*. This region has been designated Δ3'. The 895–998 domain was tested with anti-adhesin mAbs. On Western blots, only mAb 8C12 which is directed against amino acids 895–998 recognized Δ3'. This mAb was previously shown to inhibit both adherence and cytotoxicity.

Serodiagnostic studies were conducted using sera from patients with current or past amebic infection and compared to control sera. Using ELISA with immobilized Δ3' protein, 11 of 13 patients with current amebiasis had increased levels of anti-Δ3' antibodies. On Western blots, similar results were seen with 7 of 10 sera from patients with current infection reacting and with Δ3', whereas sera from past infections and negative control sera did not react with Δ3'.

The specificity of sugar binding of purified lectin (intact 170 kDa) and the Δ3' fragment were tested by allowing these substances to bind to $^{125}$I-GalNAc$_{20}$BSA in the presence of competing monosaccharides. In this experiment, PVDF membranes were spotted with purified lectin or fragment. The strips were blocked with 10 mg/ml BSA in PBS for 1 hr and then incubated in 1 mg/ml BSA/PBS containing $10^6$ cpm of the radioiodinated GalNAc-BSA and either glucose or galactose as inhibitor. After 1 hr, strips were washed three times for 5 minutes each in 1 mg/ml BSA/PBS. All incubations and washes were at room temperature. Air dried strips were exposed to a phosphorimager screen for 48 hrs.

Figure 7:
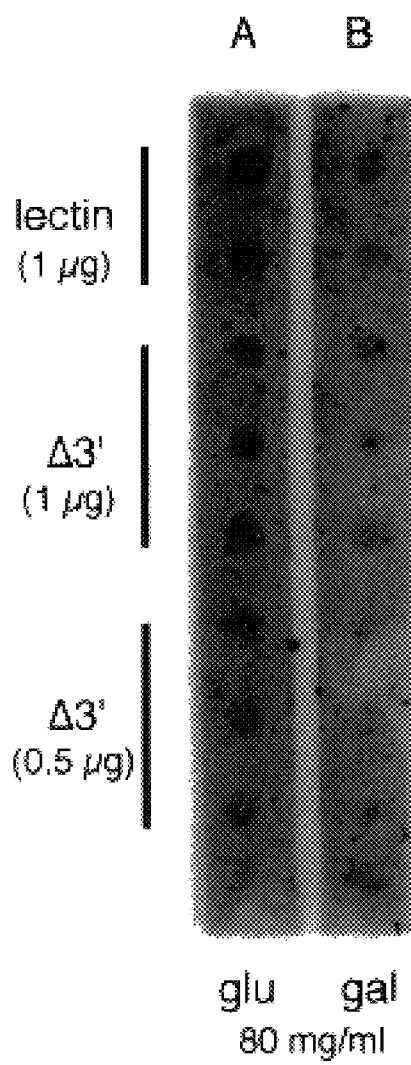
FIG. 7 is a dot blot showing the specific binding of GalNAc by purified 170 kDa lectin and by two concentrations of the fragment Δ3'. Purified lectin or fragment was spotted onto a PVDF membrane using a dot blot apparatus. Inhibition of binding to $^{125}$I-GalNAc$_{20}$BSA is shown by either glucose (strip A) or galactose, is shown.

The results in FIG. 7 show that both the fill length lectin and the specific fragment share Gal/GalNAc-binding activity which was specific (not inhibited by glucose). Thus, the binding specificity of the lectin is possessed by this short fragment.

In summary, then the Δ3' domain of the *E. histolytica* lectin contains an adherence and cytotoxicity inhibitory epitope as well as the sugar-binding specificity of the lectin. Furthermore, Δ3' is a marker for current invasive amebiasis. This peptide would therefore be particularly useful in a vaccine composition as described herein.

The references cited above are all incorporated by reference herein, whether specifically incorporated or not.

Having now fully described this invention, it will be appreciated by those skilled in the art that the same can be performed within a wide range of equivalent parameters, concentrations, and conditions without departing from the spirit and scope of the invention and without undue experimentation.

While this invention has been described in connection with specific embodiments thereof, it will be understood that it is capable of further modifications. This application is intended to cover any variations, uses, or adaptations of the invention following, in general, the principles of the invention and including such departures from the present disclosure as come within known or customary practice within the art to which the invention pertains and as may be applied to the essential features hereinbefore set forth as follows in the scope of the appended claims.

What is claimed is:

1. A recombinant, nonglycosylated, epitope-bearing peptide of the 170 kDa subunit of *E. histolytica* Gal/GalNac adherence lectin, which peptide bears at least one epitope that reacts with antibodies made in a subject infected with *E. histolytica* infection or immunized with said adherence lectin or an epitope-bearing portion thereof, with the proviso that said peptide is not
   (i) the full length 170 kDa subunit, or
   (ii) amino acid sequence residues 480–1138 of SEQ ID NO:3.

2. A peptide according to claim 1 produced in prokaryotic cells.

3. A peptide according to claim 1 which binds to Gal or GalNAc.

4. A peptide according to claim 1 encoded by one, two or all of the hgl1 gene, the hgl2 gene and the hgl3 gene.

5. A vaccine composition for immunizing a subject against *E. histolytica* infection comprising one or more peptides according to claim 1 and a pharmaceutically acceptable vehicle or carrier.

6. A vaccine composition for immunizing a subject against *E. histolytica* infection comprising one or more peptides according to claim 2 and a pharmaceutically acceptable vehicle or carrier.

7. A vaccine composition for immunizing a subject against *E. histolytica* infection comprising a pharmaceutically acceptable vehicle or carrier and one or more peptides having an amino acid sequence of SEQ ID NO:2 or SEQ ID NO:5, said peptide being selected from the group consisting of:

(a) residues 895–998 or a corresponding peptide of a naturally occurring variant of the 170 kD subunit of *E. histolytica* Gal/GalNac adherence lectin encoded by an hgl gene of any strain of *E. histolytica;*

(b) residues 946–970, or a corresponding peptide of a naturally occurring variant of the 170 kD subunit of *E. histolytica* Gal/GalNac adherence lectin encoded by an hgl gene of any strain of *E. histolytica;*

(c) residues 976–1000, or a corresponding peptide of a naturally occurring variant of the 170 kD subunit of *E. histolytica* Gal/GalNac adherence lectin encoded by an hgl gene of any strain of *E. histolytica;*

(d) residues 991–1015, or a corresponding peptide of a naturally occurring variant of the 170 kD subunit of *E. histolytica* Gal/GalNac adherence lectin encoded by an hgl gene of any strain of *E. histolytica;*

(e) residues 1006–1030, or a corresponding peptide of a naturally occurring variant of the 170 kD subunit of *E. histolytica* Gal/GalNac adherence lectin encoded by an hgl gene of any strain of *E. histolytica;* and (f) residues 1036–1060, or a corresponding peptide of a naturally occurring variant of the 170 kD subunit of *E.*

*histolytica* Gal/GalNac adherence lectin encoded by an hgl gene of any strain of *E. histolytica*.

8. A vaccine composition according to claim 7, wherein said peptide binds to Gal or GalNAc.

9. A vaccine composition according to claim 7, wherein said peptide has the amino acid sequence of residues 895–998 or a corresponding peptide of a naturally occurring variant of said 170 kD subunit encoded by an hgl gene of any strain of *E. histolytica*.

10. A vaccine composition for immunizing a subject against *E. histolytica* infection comprising one or more peptides according to claim 4 and a pharmaceutically acceptable vehicle or carrier.

11. A vaccine composition according to claim 5, 6, 7, 8, 9 or 10, further comprising an adjuvant or other immune stimulating agent.

12. A method for immunizing a subject against *Entamoeba histolytica* infection which method comprises administering to said subject an effective amount of a vaccine composition according to claim 5.

13. A method for immunizing a subject against *Entamoeba histolytica* infection which method comprises administering to said subject an effective amount of a vaccine composition according to claim 6.

14. A method for immunizing a subject against *Entamoeba histolytica* infection which method comprises administering to said subject an effective amount of a vaccine composition according to claim 7.

15. A method for immunizing a subject against *Entamoeba histolytica* infection which method comprises administering to said subject an effective amount of a vaccine composition according to claim 8.

16. A method for immunizing a subject against *Entamoeba histolytica* infection which method comprises administering to said subject an effective amount of a vaccine composition according to claim 9.

17. A method for immunizing a subject against *Entamoeba histolytica* infection which method comprises administering to said subject an effective amount of a vaccine composition according to claim 10.

18. A method for immunizing a subject against *Entamoeba histolytica* infection which method comprises administering to said subject an effective amount of a vaccine composition according to claim 11.

19. A peptide according to claim 1, which is useful in a diagnostic, a vaccine or a tolerogenic composition, which peptide has an amino acid sequence of SEQ ID NO:2 or SEQ ID NO:5 selected from the group consisting of:

(a) residues 596–1138, or a corresponding peptide of a naturally occurring variant of said 170 kD subunit encoded by an hgl gene of any strain of *E. histolytica;*

(b) residues 895–998 or a corresponding peptide of a naturally occurring variant of said 170 kD subunit encoded by an hgl gene of any strain of *E. histolytica*, and (c) residues 946–970, or a corresponding peptide of a naturally occurring variant of said 170 kD subunit encoded by an hgl gene of any strain of *E. histolytica;*

(d) residues 976–1000, or a corresponding peptide of a naturally occurring variant of said 170 kD subunit encoded by an hgl gene of any strain of *E. histolytica;*

(e) residues 991–1015, or a corresponding peptide of a naturally occurring variant of said 170 kD subunit encoded by an hgl gene of any strain of *E. histolytica;*

(f) residues 1006–1030, or a corresponding peptide of a naturally occurring variant of said 170 kD subunit encoded by an hgl gene of any strain of *E. histolytica;*

(g) residues 1036–1060, or a corresponding peptide of a naturally occurring variant of said 170 kD subunit encoded by an hgl gene of any strain of *E. histolytica;*

(b) residues 1033–1082, or a corresponding peptide of a naturally occurring variant of said 170 kD subunit encoded by an hgl gene of any strain of *E. histolytica;*

(i) residues 1082–1138, or a corresponding peptide of a naturally occurring variant of said 170 kD subunit encoded by an hgl gene of any strain of *E. histolytica*; and (j) residues 443–461 of hgl 1 (SEQ ID NO:2), or a corresponding peptide of a naturally occurring variant of said 170 kD subunit encoded by an hgl gene of any strain of *E. histolytica*.

20. A vaccine composition for immunizing a subject against *E. histolytica* infection comprising a fusion protein that includes the peptide of claim 1.

21. A vaccine composition for immunizing a subject against *E. histolytica* infection comprising a fusion protein that includes a peptide according to claim 19.

22. The peptide of claim 19 which comprises residues 895–998 of SEQ ID NO:2 or SEQ ID NO:5.

* * * * *